US011142768B2

United States Patent
Barros Rodrigues et al.

(10) Patent No.: US 11,142,768 B2
(45) Date of Patent: Oct. 12, 2021

(54) CONTROL OF INSECT INFESTATION

(71) Applicant: GreenLight Biosciences, Inc., Medford, MA (US)

(72) Inventors: Thais Barros Rodrigues, St. Louis, MO (US); Suresh Desai, Medford, MA (US); Krishnakumar Sridharan, Cary, NC (US)

(73) Assignee: GreenLight Biosciences, Inc., Medford, MA (US)

( * ) Notice: Subject to any disclaimer, the term of this patent is extended or adjusted under 35 U.S.C. 154(b) by 0 days.

(21) Appl. No.: 16/677,839

(22) Filed: Nov. 8, 2019

(65) Prior Publication Data

US 2020/0149044 A1 May 14, 2020

Related U.S. Application Data

(60) Provisional application No. 62/757,217, filed on Nov. 8, 2018.

(51) Int. Cl.

| | |
|---|---|
| ***C12N 15/113*** | (2010.01) |
| ***A01N 65/04*** | (2009.01) |
| ***A01N 63/10*** | (2020.01) |

(52) U.S. Cl.

CPC ............ *C12N 15/113* (2013.01); *A01N 63/10* (2020.01); *C12N 2310/14* (2013.01)

(58) Field of Classification Search

CPC .. C12N 15/82; C12N 15/113; C12N 15/1135; C12N 15/8218; C12N 15/8286; C12N 2310/14; C12N 2310/531; A01N 63/02; C07K 14/32; C07K 14/195

See application file for complete search history.

(56) References Cited

U.S. PATENT DOCUMENTS

| | | | |
|---|---|---|---|
| 7,655,785 | B1 | 2/2010 | Bentwich |
| 7,687,616 | B1 | 3/2010 | Bentwich et al. |
| 7,777,022 | B2 | 8/2010 | Bentwich et al. |
| 7,812,002 | B2 | 10/2010 | Feinstein |
| 7,888,497 | B2 | 2/2011 | Bentwich et al. |
| 7,943,754 | B2 | 5/2011 | Bentwich et al. |
| 8,178,503 | B2 | 5/2012 | Rigoutsos et al. |
| 8,278,287 | B2 | 10/2012 | Feinstein et al. |
| 8,410,069 | B2 | 4/2013 | Feinstein |

(Continued)

FOREIGN PATENT DOCUMENTS

| | | | |
|---|---|---|---|
| WO | WO 2006/126040 | A1 | 11/2006 |
| WO | WO 2015/100026 | A1 | 7/2015 |

(Continued)

OTHER PUBLICATIONS

GenBank Accession No. XM_023158308, submitted to GenBank on Dec. 1, 2017, Predicted: Leptinotarsa decemlineata proteasome subunit beta type-5 (LOC111503877), mRNA.*

(Continued)

*Primary Examiner* — Terra C Gibbs

(74) *Attorney, Agent, or Firm* — Wolf, Greenfield & Sacks, P.C.

(57) ABSTRACT

Provided herein are methods for using RNAi molecules targeting a proteasome beta 5 (PSMB5) gene for controlling Coleopteran insects, methods for producing RNAi molecules targeting PSMB5, and compositions comprising RNAi molecules targeting PSMB5.

23 Claims, 10 Drawing Sheets

Specification includes a Sequence Listing.

CPB MORTALITY (%)

100.00
80.00
60.00
40.00
20.00
0.00

D1 D2 D3 D4 D5 D6 D7 D8 D9

DAYS AFTER EXPOSURE

GS2 GS4

LEAF DISC CONSUMPTION (%)

100
80
60
40
20
0

D1 D2 D3 D4 D5 D6 D7 D8 D9

DAYS AFTER EXPOSURE

GS2 GS4

(56) References Cited

U.S. PATENT DOCUMENTS

| | | | |
|---|---|---|---|
| 9,777,288 | B2 | 10/2017 | Beattie et al. |
| 9,850,496 | B2 | 12/2017 | Beattie et al. |
| 9,856,495 | B2 | 1/2018 | Beattie et al. |
| 10,058,623 | B2 | 8/2018 | Krieg et al. |
| 10,059,941 | B2 | 8/2018 | Krieg et al. |
| 10,174,315 | B2 | 1/2019 | Krieg et al. |
| 10,174,323 | B2 | 1/2019 | Krieg et al. |
| 10,174,328 | B2 | 1/2019 | Krieg et al. |
| 10,240,161 | B2 | 3/2019 | Avniel et al. |
| 10,240,162 | B2 | 3/2019 | Avniel et al. |
| 10,378,012 | B2 | 8/2019 | Crawford et al. |
| 10,597,676 | B2 | 3/2020 | Beattie et al. |
| 10,655,136 | B2 | 5/2020 | Huang et al. |
| 10,683,505 | B2 | 6/2020 | Avniel et al. |
| 10,883,103 | B2 | 1/2021 | Bennett et al. |
| 10,968,449 | B2 | 4/2021 | Beattie et al. |
| 10,975,387 | B2 | 4/2021 | Beattie et al. |
| 2017/0166912 | A1 | 6/2017 | Brower-Toland et al. |
| 2017/0183683 | A1 | 6/2017 | Baum et al. |
| 2018/0223282 | A1 | 8/2018 | Krieg et al. |
| 2018/0298384 | A1 | 10/2018 | Krieg et al. |
| 2018/0305689 | A1 | 10/2018 | Sætrom et al. |
| 2018/0360030 | A1 | 12/2018 | Morgenstern et al. |
| 2019/0316130 | A1 | 10/2019 | Crawford et al. |

FOREIGN PATENT DOCUMENTS

| | | | |
|---|---|---|---|
| WO | WO 2016/018887 | A1 | 2/2016 |
| WO | WO 2017/106171 | A1 | 6/2017 |
| WO | WO 2017/176963 | A1 | 10/2017 |
| WO | WO 2019/075167 | A1 | 4/2019 |

OTHER PUBLICATIONS

GenBank Accession No. KY285055, submitted to GenBank on Nov. 25, 2016, Leptinotarsa decemlineata putative proteasome subunit beta type-5 mRNA, complete cds.*

Wikipedia (downloaded from Antisense RNA—Wikipedia on Mar. 4, 2021). https://en.wikipedia.org/wiki/Antisense_RNA#:~:text=Antisense%20RNA%20(asRNA),%20also%20referred%20to%20as%20antisense,nucleotides)%20and%20long%20(%3E200%20nucleotides)%20non-coding%20RNAs%20(ncRNAs).*

International Search Report and Written Opinion for PCT/US2019/060389 dated Feb. 21, 2020.

Arziman et al., E-RNAi: a web application to design optimized RNAi constructs. Nucleic Acids Research. 2005;33:W582-8.

Baum et al., Control of coleopteran insect pests through RNA interference. Nature Biotechnology. 2007;25(11):1322-6. Epub Nov. 4, 2007.

Bramsen et al., A large-scale chemical modification screen identifies design rules to generate siRNAs with high activity, high stability and low toxicity. Nucl Acids Res. Mar. 2009;37(9):2867-81.

Bramsen et al., Development of therapeutic-grade small interfering RNAs by chemical engineering. Frontiers in Genetics. Aug. 2012;3:22 pages.

Gasparis et al., Artificial MicroRNA-Based Specific Gene Silencing of Grain Hardness Genes in Polyploid Cereals Appeared to Be Not Stable Over Transgenic Plant Generations. Frontiers in Plant Science. Jan. 2017;7:13 pages.

Gu et al., Recent advances in RNA interference research in insects: Implications for future insect pest management strategies. Crop Protection. Mar. 2013;45:36-40.

Puglise et al., Expression Profiles and RNAi Silencing of Inhibitor of Apoptosis Transcripts in Aedes, Anopheles, and Culex Mosquitoes (Diptera: Culicidae). Journal of Medical Entomology. 2016;53(2):304-14. Epub Dec. 11, 2015.

Zhu et al., Ingested RNA interference for managing the populations of the Colorado potato beetle, *Leptinotarsa decemlineata*. Pest Manag. Sci. 2011;67(2):175-82. Epub Nov. 8, 2010.

Knorr et al., Gene silencing in Tribolium castaneum as a tool for the targeted identification of candidate RNAi targets in crop pests. Sci Rep. Feb. 1, 2018;8(1):2061. doi: 10.1038/s41598-018-20416-y. PMID: 29391456; PMCID: PMC5794766.

Rodrigues et al., Identification of highly effective target genes for RNAi-mediated control of emerald ash borer, *Agrilus planipennis*. Sci Rep. Mar. 22, 2018;8(1):5020. doi: 10.1038/s41598-018-23216-6. PMID: 29568083; PMCID: PMC5864839.

* cited by examiner

SEQUENCE LISTING

<160> NUMBER OF SEQ ID NOS: 53

<210> SEQ ID NO 1
<211> LENGTH: 1010
<212> TYPE: DNA
<213> ORGANISM: Leptinotarsa decemlineata

<400> SEQUENCE: 1

```
gtcatttgtc acttttgtca gttgtcggtc agtgaatttt caattttgct tgtaatcatc      60
agcgaattag aagttttgaa taattttta taatacagta caaaaatgag tttagcagag      120
atctgtggaa tgcaagattt agattcattt aggacgaact tctgtcccaa cgagttggat     180
agaatgtgca ccaatttcga aaataatctg aatctggaaa tgcctccttt tgcaaatcca     240
gcagcaaagg tatcacaatt aacgagagat gaaagcggtc gagaaataaa aatggctttt     300
gatcatggta ccacaactct gggtttcatg tataaaggtg gtgttgttct tgctgtagac     360
tccagagcta caggcggaca atttattggg tcgcaaacca tgaaaaaaat tgtggaaatc     420
aatgatttct tattgggaac attggctgga ggtgcggcag actgtgttta ttgggaccgt     480
gtactggcca aacaatgtag aatgtatgaa ttaaggaaca gggagcgtat ttctgtagca     540
gctgcttcca aattgatggc aaacatggta tacaattaca agggaatggg actgtcaatg     600
ggaatgatgt tagcaggatg ggataaaaga ggtccacacc tgtactatgt agactccgag     660
ggtaccagaa cacctggaaa agtctttagt gtgggttcag gttcaattta tgcatttggt     720
gtcttggatt ccggatacaa atgggatttg acggatgagg aggcttacga tttgggtcgc     780
agggcgattt accatgccac acacagagat gcctactctg gaggtatcgt gagggtttat     840
cacatgaagg agactggttg gatacatatt gataacaatg attgtaatga tttacattat     900
aagtaccagg ctgagaagga agatttggaa aatacaattg cttaactgac agtttcattt     960
caatcaagtt gaaggttcat tcgtatttct taataaaaat aagtttttaa               1010
```

<210> SEQ ID NO 2
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 2

```
aggtgcggca gactgtgttt attgggaccg tgtactggcc aaacaatgta gaatgtatga      60
attaaggaac agggagcgta tttctgtagc agctgcttcc aaattgatgg caaacatggt     120
atacaattac aagggaatgg gactgtcaat gggaatgatg ttagcaggat gggataaaag     180
agtaaactcc gagggtacca gaacacctgg aaaagtcttt agtgtgggtt caggttcaat     240
ttatgcattt ggtgtcttgg attccggata caaatgggat ttgacggatg aggaggctta     300
cgatttgggt cgcagggcga tttaccatgc cacacacaga gatgcctact ctggaggtat     360
cgtgagggtt tatcacatga aggagactgg ttggatacat attgataaca atgattgtaa     420
tgatttacat tataagtacc aggctgagaa ggaagatttg                          460
```

<210> SEQ ID NO 3
<211> LENGTH: 524
<212> TYPE: DNA
<213> ORGANISM: Artificial Sequence
<220> FEATURE:
<223> OTHER INFORMATION: Synthetic polynucleotide

<400> SEQUENCE: 3

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
```

```
ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acgg                     524


<210> SEQ ID NO 4
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 4

ggtcatttgt cacttttgtc agttgtcggt cagtgaattt tcaattttgc ttgtaatcat     60

cagcgaatta gaagttttga ataatttttt ataatacagt acaaaaatga gtttagcaga    120

gatctgtgga atgcaagatt tagattcatt taggacgaac ttctgtccca acgagttgga    180

tagaatgtgc accaatttcg aaaataatct gaatctggaa atgcctcctt ttgcaaatcc    240

agcagcaaag gtatcacaat taacgagaga tgaaagcggt cgagaaataa aaatggcttt    300

tgatcatggt accacaactc tggtttcat gtataaaggt ggtgttgttc ttgctgtaga     360

ctccagagct acaggcggac aatttattgg gtcgcaaacc atgaaaaaaa ttgtggaaat    420

caatgatttc ttattgggaa cattggctgg                                     450


<210> SEQ ID NO 5
<211> LENGTH: 478
<212> TYPE: DNA
<213> ORGANISM: Artificial Sequence
<220> FEATURE:
<223> OTHER INFORMATION: Synthetic polynucleotide

<400> SEQUENCE: 5

aggtgcggca gactgtgttt attgggaccg tgtactggcc aaacaatgta gaatgtatga     60

attaaggaac agggagcgta tttctgtagc agctgcttcc aaattgatgg caaacatggt    120

atacaattac aagggaatgg gactgtcaat gggaatgatg ttagcaggat gggataaaag    180

aggtccacac ctgtactatg tagactccga gggtaccaga acacctggaa aagtctttag    240

tgtgggttca ggttcaattt atgcatttgg tgtcttggat tccggataca aatgggattt    300

gacggatgag gaggcttacg atttgggtcg cagggcgatt taccatgcca cacacagaga    360

tgcctactct ggaggtatcg tgagggttta tcacatgaag gagactggtt ggatacatat    420

tgataacaat gattgtaatg atttacatta taagtaccag gctgagaagg aagatttg      478


<210> SEQ ID NO 6
<211> LENGTH: 561
<212> TYPE: DNA
<213> ORGANISM: Artificial Sequence
<220> FEATURE:
<223> OTHER INFORMATION: Synthetic polynucleotide

<400> SEQUENCE: 6

aggtgcggca gactgtgttt attgggaccg tgtactggcc aaacaatgta gaatgtatga     60

attaaggaac agggagcgta tttctgtagc agctgcttcc aaattgatgg caaacatggt    120

atacaattac aagggaatgg gactgtcaat gggaatgatg ttagcaggat gggataaaag    180
```

aggtccacac ctgtactatg tagactccga gggtaccaga acacctggaa aagtctttag 240
tgtgggttca ggttcaattt atgcatttgg tgtcttggat tccggataca aatgggattt 300
gacggatgag gaggcttacg atttgggtcg cagggcgatt taccatgcca cacacagaga 360
tgcctactct ggaggtatcg tgagggttta tcacatgaag gagactggtt ggatacatat 420
tgataacaat gattgtaatg atttacatta taagtaccag gctgagaagg aagatttgga 480
aaatacaatt gcttaactga cagtttcatt tcaatcaagt tgaaggttca ttcgtatttc 540
ttaataaaaa taagttttta a 561

<210> SEQ ID NO 7
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 7
acgtcccgct gactattatt atagggaccg taagctagac taacaatgca gaatgtatga 60
ggtgaggaac ggggattgta ctttaccagc agcggcttgc cagcggatgg taaccgtggg 120
ataccatgcc acgtaaatag gaatatcgag gggaatgagg ttagctggat aggcgaaaag 180
agtacacccc gaagctagca gaatccctga aaaacactgt attctggttt ccggttaaat 240
ctttgctttt ggtgtctggg atcccagata aatatggaat ttgtcaatct aagaagcgaa 300
ccaatacggc ctcggggcct tctaccgtga cggcgacgga gatgcctact cttgcggagt 360
ccttcgcgcg tatcacatca aggacacgga ttgtatccat attgataaca atttttgcat 420
tgctgaaact taaaagtatt agcctgggaa gtccgatttg 460

<210> SEQ ID NO 8
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 8
cggttcgaca aactgagttt gttgggagcc tggactggcc aagcaatgta gaatctttga 60
tttcaggatg ggggagcgta tttccgtagc aacggcttcc aaattcatgt cgtatatggt 120
tgaaacttac aaggaaataa gactgtctgt gggaatgatg ttaacaggac cagatgaaag 180
agttacatcg gacggtatca gaacaatttc ataaaacttg cgtataggtt taggtaaact 240
ctatccagtt gatgtcttgg agtcctgata caaagggtat ttgaaggaag cggacgctta 300
cgatttgctt cggagggcga tgttccatcc cacgcctgga gatgcctact ctcgaggtca 360
cgtgagggtt catcacatga aggggtggag ttcgattgat atgaatgata atttttgcaa 420
tcgtttacat tataaggtcc ctgctgagga agatgtcata 460

<210> SEQ ID NO 9
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 9
aggtgggtcc gactgtcttt attgggtacg tgtacttggg agaccatgta taattaagga 60

-continued

```
attaaggtcc atggtgcata tttcttgagc acctgcttca taagtgatgg gaatcatggt    120

ataccgttct aagggcacga gactgtcaaa gggaatgatg taagccggat gggataaaag    180

aataagctcc gaaggtaaca gaacacattg aaaaggcttt agtgtgggta gagcttcaac    240

ttatgaatta agagtcatgg attccggata caaatggggt ttgacggacg aagagcgtta    300

cgacttgggt ccctaggcgc tttacaaagc ctcatacaga gatacctact ccggagggat    360

aaaagtggtt tatcaaatga tagagacagg taggattcat gttgataaca atgattgtac    420

tgaattactt tataagtacc aggccgagga ctaatatttg                          460
```

```
<210> SEQ ID NO 10
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 10

aggtgcggga gactatgtgt cctgggaacg tgtactggcc aaacatcgta gaatttacga     60

agtatctagc agggagcgta gttctgtagc agctgcgtcc aaattgatgg caaacatggc    120

attcaatttc taaggaatgg gactgttcat ggaaatgatg tttgcatgat gggataaatg    180

agtagacgcc gaggctacaa gagcacctgc aaaagcattt tgtgcgggtt cagcttccag    240

atatccattt cgtgtctagg attccggaca caaatgggat ttgacggatt aggagactaa    300

cgatttgggt cgcagggcaa tttaccatgc cacacgcaga gatgcctact ctgtaggtat    360

cgtgaggatt tacgagatga agtggcctgg ttggatacat attgataaca atgattgtaa    420

taatttacgg tttaagtacg aggctgagaa gggggatata                          460
```

```
<210> SEQ ID NO 11
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 11

aggtacggca gtctgtgttt attgcgaccg tgtactggcc aaacgatgta ggaagtatga     60

gttaaggaac agggagcata gttgtgtagc agctgcttcc aacatgacgg caaacatggt    120

ataccattac aagggaatgg gactgtcaaa gggaataatg ttagcaggat ggcatgattg    180

agaaaactcc gagggtacca aaacacatgg aaaagtcttt agtgtgggtt caggttcaat    240

ttatgtattt ggtgtcttgg attccggata caaatgggat ttgacggatg aggaggctta    300

cgatttgagt cgttgggcgg tttaccatcc cacacacaga gatgcctact ctggaggtat    360

cgagggagtt aaccacatgc aggagcctgg gtggatacaa attgataaca atgattggaa    420

tgatctacat tatagggtcc aggctgaggg ggaagttttg                          460
```

```
<210> SEQ ID NO 12
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 12

atttgcggca ggctgtgttt attgggaccg tgtactggcc aaacaatgta gaatgtatga     60

attaaggaac agggagcgta gttctgtagc agctgcttcc aaattggtgg caaacatggt    120
```

atacaattac gagggaatgg gactgtcgat gggaatgatg taagcaggat gggatgaagg 180
agtaaactcc gagggtacca gaacacctgg aaaagtcttt agtgggggtt caggttcgac 240
ttatgcattt gatgtcttgg attccggata caaatgggat ttgaaggatg aggaggctta 300
cgattagggt cgcagggcga tttaccatgc cacacgcaga gatgcctact ctggaggaat 360
cttgagggtt tatcacttga aggaaactgg ttggatacat attgataaca atgattggaa 420
tgatttacat tataagtacc aggctgagaa ggaagatttg 460

<210> SEQ ID NO 13
<211> LENGTH: 200
<212> TYPE: DNA
<213> ORGANISM: Artificial Sequence
<220> FEATURE:
<223> OTHER INFORMATION: Synthetic polynucleotide

<400> SEQUENCE: 13
atttctgtag cagctgcttc caaattgatg gcaaacatgg tatacaatta caagggaatg 60
ggactgtcaa tgggaatgat gttagcagga tgggataaaa gagtaaactc cgagggtacc 120
agaacacctg gaaaagtctt tagtgtgggt tcaggttcaa tttatgcatt tggtgtcttg 180
gattccggat acaaatggga 200

<210> SEQ ID NO 14
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 14
tgatggcaaa catggtatac aattacaagg gaatgggact gtcaatggga atgatgttag 60
caggatggga taaaagagta aactccgagg gtaccagaac acctggaaaa gtctttagtg 120
tgggttcagg ttcaatttat gcatttggtg 150

<210> SEQ ID NO 15
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 15
caagggaatg ggactgtcaa tgggaatgat gttagcagga tgggataaaa gagtaaactc 60
cgagggtacc agaacacctg gaaaagtctt tagtgtgggt 100

<210> SEQ ID NO 16
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 16
atgatgttag caggatggga taaaagagta aactccgagg gtaccagaac 50

<210> SEQ ID NO 17
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 17
ggatgggata aaagagtaaa ctccg 25

<210> SEQ ID NO 18
<211> LENGTH: 1010
<212> TYPE: RNA
<213> ORGANISM: Artificial Sequence
<220> FEATURE:
<223> OTHER INFORMATION: Synthetic polynucleotide

<400> SEQUENCE: 18
gucauuuguc acuuuuguca guugucgguc agugaauuuu caauuuugcu uguaaucauc 60
agcgaauuag aaguuuugaa uaauuuuuua uaauacagua caaaaaugag uuuagcagag 120
aucuguggaa ugcaagauuu agauucauuu aggacgaacu ucugucccaa cgaguuggau 180
agaaugugca ccaauuucga aaauaaucug aaucuggaaa ugccuccuuu ugcaaaucca 240
gcagcaaagg uaucacaauu aacgagagau gaaagcgguc gagaaauaaa aauggcuuuu 300
gaucauggua ccacaacucu ggguuucaug uauaaaggug guguuguucu ugcuguagac 360
uccagagcua caggcggaca auuuauuggg ucgcaaacca ugaaaaaaau uguggaaauc 420
aaugauuucu uauugggaac auuggcugga ggugcggcag acuguguuua uugggaccgu 480
guacuggcca aacaauguag aauguaugaa uuaaggaaca gggagcguau uucuguagca 540
gcugcuucca aauugauggc aaacauggua uacaauuaca agggaauggg acugucaaug 600
ggaaugaugu uagcaggaug ggauaaaaga gguccacacc uguacuaugu agacuccgag 660
gguaccagaa caccuggaaa agucuuuagu gugggguucag guucaauuua ugcauuuggu 720
gucuuggauu ccggauacaa augggauuug acggaugagg aggcuuacga uuugggucgc 780
agggcgauuu accaugccac acacagagau gccuacucug gagguaucgu gaggguuuau 840
cacaugaagg agacugguug gauacauauu gauaacaaug auuguaauga uuuacauuau 900
aaguaccagg cugagaagga agauuuggaa aauacaauug cuuaacugac aguuucauuu 960
caaucaaguu gaagguucau ucguauuucu uaauaaaaau aaguuuuuaa 1010

<210> SEQ ID NO 19
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 19
aggugcggca gacuguguuu auugggaccg uguacuggcc aaacaaugua gaauguauga 60
auuaaggaac agggagcgua uuucuguagc agcugcuucc aaauugaugg caaacauggu 120
auacaauuac aagggaaugg gacugucaau gggaaugaug uuagcaggau gggauaaaag 180
aguaaacucc gaggguacca gaacaccugg aaaagucuuu agugugggguu cagguucaau 240 uuaugcauuu ggugucuugg auuccggaua caaaugggau uugacggaug aggaggcuua 300
cgauuugggu cgcagggcga uuuaccaugc cacacacaga gaugccuacu cuggagguau 360
cgugaggguu uaucacauga aggagacugg uuggauacau auugauaaca augauuguaa 420
ugauuuacau uauaaguacc aggcugagaa ggaagauuug 460

<210> SEQ ID NO 20
<211> LENGTH: 524

<212> TYPE: RNA
<213> ORGANISM: Artificial Sequence
<220> FEATURE:
<223> OTHER INFORMATION: Synthetic polynucleotide

<400> SEQUENCE: 20

```
auggugagca agggcgagga gcuguucacc ggggugguge ccauccuggu cgagcuggac     60

ggcgacguaa acggccacaa guucagcgug uccggcgagg gcgagggcga ugccaccuac    120

ggcaagcuga cccugaaguu caucugcacc accggcaagc ugcccgugcc cuggcccacc    180

cucgugacca cccugaccua cggcgugcag ugcuucagcc gcuaccccga ccacaugaag    240

cagcacgacu ucuucaaguc cgccaugccc gaaggcuacg uccaggagcg caccaucuuc    300

uucaaggacg acggcaacua caagacccgc gccgagguga aguucgaggg cgacacccug    360

gugaaccgca ucgagcugaa gggcaucgac uucaaggagg acggcaacau ccuggggcac    420

aagcuggagu acaacuacaa cagccacaac gucuauauca uggccgacaa gcagaagaac    480

ggcaucaagg ugaacuucaa gauccgccac aacaucgagg acgg                     524
```

<210> SEQ ID NO 21
<211> LENGTH: 450
<212> TYPE: RNA
<213> ORGANISM: Artificial Sequence
<220> FEATURE:
<223> OTHER INFORMATION: Synthetic polynucleotide

<400> SEQUENCE: 21

```
ggucauuugu cacuuuuguc aguugucggu cagugaauuu ucaauuuugc uuguaaucau     60

cagcgaauua gaaguuuuga auaauuuuuu auaauacagu acaaaaauga guuuagcaga    120

gaucugugga augcaagauu uagauucauu uaggacgaac uucuguccca acgaguugga    180

uagaaugugc accaauuucg aaaauaaucu gaaucuggaa augccuccuu uugcaaaucc    240

agcagcaaag guaucacaau uaacgagaga ugaaagcggu cgagaaauaa aaauggcuuu    300

ugaucauggu accacaacuc uggguuucau guauaaaggu gguguuguuc uugcuguaga    360

cuccagagcu acaggcggac aauuuauugg gucgcaaacc augaaaaaaa uuguggaaau    420

caaugauuuc uuauugggaa cauuggcugg                                     450
```

<210> SEQ ID NO 22
<211> LENGTH: 478
<212> TYPE: RNA
<213> ORGANISM: Artificial Sequence
<220> FEATURE:
<223> OTHER INFORMATION: Synthetic polynucleotide

<400> SEQUENCE: 22

```
aggugcggca gacuguguuu auugggaccg uguacuggcc aaacaaugua gaauguauga     60

auuaaggaac agggagcgua uuucuguagc agcugcuucc aaauugaugg caaacauggu    120

auacaauuac aagggaaugg gacugucaau gggaaugaug uuagcaggau gggauaaaag    180

agguccacac cuguacuaug uagacuccga ggguaccaga acaccuggaa aagucuuuag    240

ugugggguuca gguucaauuu augcauuugg ugucuuggau uccggauaca aaugggauuu    300

gacggaugag gaggcuuacg auuugggucg cagggcgauu uaccaugcca cacacagaga    360

ugccuacucu ggagguaucg ugaggguuua ucacaugaag gagacugguu ggauacauau    420

ugauaacaau gauuguaaug auuuacauua uaaguaccag gcugagaagg aagauuug      478
```

<210> SEQ ID NO 23

<211> LENGTH: 561
<212> TYPE: RNA
<213> ORGANISM: Artificial Sequence
<220> FEATURE:
<223> OTHER INFORMATION: Synthetic polynucleotide

<400> SEQUENCE: 23
aggugcggca gacuguguuu auugggaccg uguacuggcc aaacaaugua gaauguauga 60
auuaaggaac agggagcgua uuucuguagc agcugcuucc aaauugaugg caaacauggu 120
auacaauuac aagggaaugg gacugucaau gggaaugaug uuagcaggau gggauaaaag 180
agguccacac cuguacuaug uagacuccga ggguaccaga acaccuggaa aagucuuuag 240 ugugggguuca gguucaauuu augcauuugg ugucuuggau uccggauaca aaugggauuu 300
gacggaugag gaggcuuacg auuugggucg cagggcgauu uaccaugcca cacacagaga 360
ugccuacucu ggagguaucg ugaggguuua ucacaugaag gagacugguu ggauacauau 420
ugauaacaau gauuguaaug auuuacauua uaaguaccag gcugagaagg aagauuugga 480
aaauacaauu gcuuaacuga caguuucauu ucaaucaagu ugaagguuca uucguauuuc 540
uuaauaaaaa uaaguuuuua a 561

<210> SEQ ID NO 24
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 24
acgucccgcu gacuauuauu auagggaccg uaagcuagac uaacaaugca gaauguauga 60
ggugaggaac ggggauugua cuuuaccagc agcggcuugc cagcggaugg uaaccguggg 120
auaccaugcc acguaaauag gaauaucgag gggaaugagg uuagcuggau aggcgaaaag 180
aguacacccc gaagcuagca gaaucccuga aaaacacugu auucugguuu ccgguuaaau 240
cuuugcuuuu ggugucuggg aucccagaua aauauggaau uugucaaucu aagaagcgaa 300
ccaauacggc cucggggccu ucuaccguga cggcgacgga gaugccuacu cuugcggagu 360
ccuucgcgcg uaucacauca aggacacgga uuguauccau auugauaaca auuuuugcau 420
ugcugaaacu uaaaaguauu agccugggaa guccgauuug 460

<210> SEQ ID NO 25
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 25
cgguucgaca aacugaguuu guugggagcc uggacuggcc aagcaaugua gaaucuuuga 60
uuucaggaug ggggagcgua uuuccguagc aacggcuucc aaauucaugu cguauauggu 120
ugaaacuuac aaggaaauaa gacugucugu gggaaugaug uuaacaggac cagaugaaag 180
aguuacaucg gacgguauca gaacaauuuc auaaaacuug cguauagguu uagguaaacu 240
cuauccaguu gaugucuugg aguccugaua caaaggguau uugaaggaag cggacgcuua 300
cgauuugcuu cggagggcga uguuccaucc cacgccugga gaugccuacu cucgagguca 360
cgugaggguu caucacauga aggggguggag uucgauugau augaaugaua auuuuugcaa 420
ucguuuacau uauaaggucc cugcugagga agaugucaua 460

<210> SEQ ID NO 26
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 26

```
aggugggucc gacugucuuu auuggguacg uguacuuggg agaccaugua uaauuaagga     60
auuaaggucc auggugcaua uuucuugagc accugcuuca uaagugaugg gaaucauggu    120
auaccguucu aagggcacga gacugucaaa gggaaugaug uaagccggau gggauaaaag    180
aauaagcucc gaagguaaca gaacacauug aaaaggcuuu agugugggua gagcuucaac    240
uuaugaauua agagucaugg auuccggaua caaauggggu uugacggacg aagagcguua    300
cgacuugggu cccuaggcgc uuuacaaagc cucauacaga gauaccuacu ccggagggau    360
aaaagugguu uaucaaauga uagagacagg uaggauucau guugauaaca augauuguac    420
ugaauuacuu uauaaguacc aggccgagga cuaauauuug                         460
```

<210> SEQ ID NO 27
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 27

```
aggugcggga gacuaugugu ccugggaacg uguacuggcc aaacaucgua gaauuuacga     60
aguaucuagc agggagcgua guucuguagc agcugcgucc aaauugaugg caaacauggc    120
auucaauuuc uaaggaaugg gacuguucau ggaaaugaug uuugcaugau gggauaaaug    180
aguagacgcc gaggcuacaa gagcaccugc aaaagcauuu ugugcggguu cagcuuccag    240
auauccauuu cgugucuagg auuccggaca caaaugggau uugacggauu aggagacuaa    300
cgauuugggu cgcagggcaa uuuaccaugc cacacgcaga gaugccuacu cuguagguau    360
cgugaggauu uacgagauga aguggccugg uuggauacau auugauaaca augauuguaa    420
uaauuuacgg uuuaaguacg aggcugagaa gggggauaua                         460
```

<210> SEQ ID NO 28
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 28

```
agguacggca gucuguguuu auugcgaccg uguacuggcc aaacgaugua ggaaguauga     60
guuaaggaac agggagcaua guuguguagc agcugcuucc aacaugacgg caaacauggu    120
auaccauuac aagggaaugg gacugucaaa gggaauaaug uuagcaggau ggcaugauug    180
agaaaacucc gaggguacca aaacacaugg aaaagucuuu agugugggguu cagguucaau    240
uuauguauuu ggugucuugg auuccggaua caaaugggau uugacggaug aggaggcuua    300
cgauuugagu cguugggcgg uuuaccaucc cacacacaga gaugccuacu cuggagguau    360
cgagggaguu aaccacaugc aggagccugg guggauacaa auugauaaca augauuggaa    420
ugaucuacau uauagggucc aggcugaggg ggaaguuuug                         460
```

<210> SEQ ID NO 29
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 29
auuugcggca ggcuguguuu auugggaccg uguacuggcc aaacaaugua gaauguauga 60
auuaaggaac agggagcgua guucuguagc agcugcuucc aaauuggugg caaacauggu 120
auacaauuac gagggaaugg gacugucgau gggaaugaug uaagcaggau gggaugaagg 180
aguaaacucc gaggguacca gaacaccugg aaaagucuuu aguggggguu cagguucgac 240
uuaugcauuu gaugucuugg auuccggaua caaaugggau uugaaggaug aggaggcuua 300
cgauuagggu cgcagggcga uuuaccaugc cacacgcaga gaugccuacu cuggaggaau 360
cuugaggguu uaucacuuga aggaaacugg uuggauacau auugauaaca augauuggaa 420
ugauuuacau uauaaguacc aggcugagaa ggaagauuug 460

<210> SEQ ID NO 30
<211> LENGTH: 200
<212> TYPE: RNA
<213> ORGANISM: Artificial Sequence
<220> FEATURE:
<223> OTHER INFORMATION: Synthetic polynucleotide

<400> SEQUENCE: 30
auuucuguag cagcugcuuc caaauugaug gcaaacaugg uauacaauua caagggaaug 60
ggacugucaa ugggaaugau guuagcagga ugggauaaaa gaguaaacuc cgaggguacc 120
agaacaccug gaaaagucuu uagugugggu ucagguucaa uuuaugcauu uggugucuug 180
gauuccggau acaaauggga 200

<210> SEQ ID NO 31
<211> LENGTH: 150
<212> TYPE: RNA
<213> ORGANISM: Artificial Sequence
<220> FEATURE:
<223> OTHER INFORMATION: Synthetic polynucleotide

<400> SEQUENCE: 31
ugauggcaaa caugguauac aauuacaagg gaaugggacu gucaauggga augauguuag 60
caggauggga uaaaagagua aacuccgagg guaccagaac accuggaaaa gucuuuagug 120
uggguucagg uucaauuuau gcauuuggug 150

<210> SEQ ID NO 32
<211> LENGTH: 100
<212> TYPE: RNA
<213> ORGANISM: Artificial Sequence
<220> FEATURE:
<223> OTHER INFORMATION: Synthetic polynucleotide

<400> SEQUENCE: 32
caagggaaug ggacugucaa ugggaaugau guuagcagga ugggauaaaa gaguaaacuc 60
cgaggguacc agaacaccug gaaaagucuu uagugugggu 100

<210> SEQ ID NO 33
<211> LENGTH: 50
<212> TYPE: RNA
<213> ORGANISM: Artificial Sequence
<220> FEATURE:
<223> OTHER INFORMATION: Synthetic polynucleotide

<400> SEQUENCE: 33
augauguuag caggauggga uaaaagagua aacuccgagg guaccagaac 50

<210> SEQ ID NO 34
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 34
ggaugggaua aaagaguaaa cuccg 25

<210> SEQ ID NO 35
<211> LENGTH: 1010
<212> TYPE: RNA
<213> ORGANISM: Artificial Sequence
<220> FEATURE:
<223> OTHER INFORMATION: Synthetic polynucleotide

<400> SEQUENCE: 35
uuaaaaacuu auuuuuauua agaaauacga augaaccuuc aacuugauug aaaugaaacu 60
gucaguuaag caauuguauu uuccaaaucu uccuucucag ccugguacuu auaauguaaa 120
ucauuacaau cauuguuauc aauauguauc caaccagucu ccuucaugug auaaacccuc 180
acgauaccuc cagaguaggc aucucugugu guggcauggu aaaucgcccu gcgacccaaa 240
ucguaagccu ccucauccgu caaaucccau uuguauccgg aauccaagac accaaaugca 300
uaaauugaac cugaacccac acuaaagacu uuuccaggug uucugguacc cucggagucu 360
acauaguaca ggugugggacc ucuuuuaucc cauccugcua acaucauucc cauugacagu 420
cccauucccu uguaauugua uaccauguuu gccaucaauu uggaagcagc ugcuacagaa 480
auacgcuccc uguuccuuaa uucauacauu cuacauuguu uggccaguac acggucccaa 540
uaaacacagu cugccgcacc uccagccaau guucccaaua agaaaucauu gauuuccaca 600
auuuuuuuca ugguuugcga cccaauaaau uguccgccug uagcucugga gucuacagca 660
agaacaacac caccuuuaua caugaaaccc agaguugugg uaccaugauc aaaagccauu 720
uuuauuucuc gaccgcuuuc aucucucguu aauugugaua ccuuugcugc uggauuugca 780
aaaggaggca uuuccagauu cagauuauuu ucgaaauugg ugcacauucu auccaacucg 840
uugggacaga aguucguccu aaaugaaucu aaaucuugca uuccacagau cucugcuaaa 900
cucauuuuug uacuguauua uaaaaaauua uucaaaacuu cuaauucgcu gaugauuaca 960
agcaaaauug aaaauucacu gaccgacaac ugacaaaagu gacaaaugac 1010

<210> SEQ ID NO 36
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 36
caaaucuucc uucucagccu gguacuuaua auguaaauca uuacaaucau uguuaucaau 60
auguauccaa ccagucuccu ucaugugaua aacccucacg auaccuccag aguaggcauc 120
ucugugugug gcaugguaaa ucgcccugcg acccaaaucg uaagccuccu cauccgucaa 180

```
aucccauuug uauccggaau ccaagacacc aaaugcauaa auugaaccug aacccacacu    240

aaagacuuuu ccagguguuc ugguacccuc ggaguuuacu cuuuuauccc auccugcuaa    300

caucauuccc auugacaguc ccauucccuu guaauuguau accauguuug ccaucaauuu    360

ggaagcagcu gcuacagaaa uacgcucccu guuccuuaau ucauacauuc uacauuguuu    420

ggccaguaca cgguccaau aaacacaguc ugccgcaccu                          460
```

<210> SEQ ID NO 37
<211> LENGTH: 524
<212> TYPE: RNA
<213> ORGANISM: Artificial Sequence
<220> FEATURE:
<223> OTHER INFORMATION: Synthetic polynucleotide

<400> SEQUENCE: 37

```
ccguccucga uguuguggcg gaucuugaag uucaccuuga ugccguucuu cugcuugucg     60

gccaugauau agacguugug gcuguuguag uuguacucca gcuugugccc caggauguug    120

ccguccuccu ugaagucgau gcccuucagc ucgaugcggu ucaccagggu gucgcccucg    180

aacuucaccu cggcgcgggu cuuguaguug ccgucguccu ugaagaagau ggugcgcucc    240

uggacguagc cuucgggcau ggcggacuug aagaagucgu gcugcuucau guggucgggg    300

uagcggcuga agcacugcac gccguagguc agggugguca cgagggugg ccagggcacg     360

ggcagcuugc cgguggugca gaugaacuuc agggucagcu ugccguaggu ggcaucgccc    420

ucgcccucgc cggacacgcu gaacuugugg ccguuuacgu cgccguccag cucgaccagg    480

augggcacca ccccggugaa cagcuccucg cccuugcuca ccau                    524
```

<210> SEQ ID NO 38
<211> LENGTH: 450
<212> TYPE: RNA
<213> ORGANISM: Artificial Sequence
<220> FEATURE:
<223> OTHER INFORMATION: Synthetic polynucleotide

<400> SEQUENCE: 38

```
ccagccaaug uucccaauaa gaaaucauug auuuccacaa uuuuuuucau gguuugcgac     60

ccaauaaauu guccgccugu agcucuggag ucuacagcaa gaacaacacc accuuuauac    120

augaaaccca gaguuguggu accaugauca aaagccauuu uuauuucucg accgcuuuca    180

ucucucguua auugugauac cuuugcugcu ggauuugcaa aaggaggcau uuccagauuc    240

agauuauuuu cgaaauuggu gcacauucua uccaacucgu ugggacagaa guucguccua    300

aaugaaucua aaucuugcau uccacagauc ucugcuaaac ucauuuuugu acuguauuau    360

aaaaaauuau ucaaaacuuc uaauucgcug augauuacaa gcaaaauuga aaauucacug    420

accgacaacu gacaaaagug acaaaugacc                                    450
```

<210> SEQ ID NO 39
<211> LENGTH: 478
<212> TYPE: RNA
<213> ORGANISM: Artificial Sequence
<220> FEATURE:
<223> OTHER INFORMATION: Synthetic polynucleotide

<400> SEQUENCE: 39

```
caaaucuucc uucucagccu gguacuuaua auguaaauca uuacaaucau uguuaucaau     60

auguauccaa ccagucuccu ucaugugaua aacccucacg auaccuccag aguaggcauc    120

ucugugugug gcaugguaaa ucgcccugcg acccaaaucg uaagccuccu cauccgucaa    180
```

```
aucccauuug uauccggaau ccaagacacc aaaugcauaa auugaaccug aacccacacu    240

aaagacuuuu ccagguguuc ugguacccuc ggagucuaca uaguacaggu guggaccucu    300

uuuaucccau ccugcuaaca ucauucccau ugacaguccc auucccuugu aauuguauac    360

cauguuugcc aucaauuugg aagcagcugc uacagaaaua cgcucccugu uccuuaauuc    420

auacauucua cauuguuugg ccaguacacg gucccaauaa acacagucug ccgcaccu      478
```

<210> SEQ ID NO 40
<211> LENGTH: 561
<212> TYPE: RNA
<213> ORGANISM: Artificial Sequence
<220> FEATURE:
<223> OTHER INFORMATION: Synthetic polynucleotide

<400> SEQUENCE: 40

```
uuaaaaacuu auuuuuauua agaaauacga augaaccuuc aacuugauug aaaugaaacu     60

gucaguuaag caauuguauu uuccaaaucu uccuucucag ccugguacuu auaauguaaa    120

ucauuacaau cauuguuauc aauauguauc caaccagucu ccuucaugug auaaacccuc    180

acgauaccuc cagaguaggc aucucugugu guggcauggu aaaucgcccu gcgacccaaa    240

ucguaagccu ccucauccgu caaaucccau uuguauccgg aauccaagac accaaaugca    300

uaaauugaac cugaacccac acuaaagacu uuuccaggug uucugguacc cucggagucu    360

acauaguaca gguguggacc ucuuuuaucc cauccugcua acaucauucc cauugacagu    420

cccauucccu uguaauugua uaccauguuu gccaucaauu uggaagcagc ugcuacagaa    480

auacgcuccc uguuccuuaa uucauacauu cuacauuguu uggccaguac acggucccaa    540

uaaacacagu cugccgcacc u                                              561
```

<210> SEQ ID NO 41
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 41

```
caaaucggac uucccaggcu aauacuuuua aguuucagca augcaaaaau uguuaucaau     60

auggauacaa uccguguccu ugaugugaua cgcgcgaagg acuccgcaag aguaggcauc    120

uccgucgccg ucacgguaga aggccccgag gccguauugg uucgcuucuu agauugacaa    180

auuccauauu uaucugggau cccagacacc aaaagcaaag auuuaaccgg aaaccagaau    240

acaguguuuu ucagggauuc ugcuagcuuc ggggguguacu cuuuucgccu auccagcuaa    300

ccucauuccc cucgauauuc cuauuuacgu ggcaugguau cccacgguua ccauccgcug    360

gcaagccgcu gcugguaaag uacaaucccc guuccucacc ucauacauuc ugcauuguua    420

gucuagcuua cggucccuau aauaaauaguc agcgggacgu                          460
```

<210> SEQ ID NO 42
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 42

```
uaugacaucu uccucagcag ggaccuuaua auguaaacga uugcaaaaau uaucauucau     60
```

```
aucaaucgaa cuccaccccu ucaugugaug aacccucacg ugaccucgag aguaggcauc    120

uccaggcgug ggauggaaca ucgcccuccg aagcaaaucg uaagcguccg cuuccuucaa    180

auacccuuug uaucaggacu ccaagacauc aacuggauag aguuuaccua aaccuauacg    240

caaguuuuau gaaauuguuc ugauaccguc cgauguaacu cuuucaucug guccuguuaa    300

caucauuccc acagacaguc uuauuuccuu guaaguuuca accauauacg acaugaauuu    360

ggaagccguu gcuacggaaa uacgcucccc cauccugaaa ucaaagauuc uacauugcuu    420

ggccagucca ggcucccaac aaacucaguu ugucgaaccg                          460
```

<210> SEQ ID NO 43
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 43

```
caaauauuag uccucggccu gguacuuaua aaguaauuca guacaaucau uguuaucaac     60

augaauccua ccugucucua ucauuugaua aaccacuuuu aucccuccgg aguagguauc    120

ucuguaugag gcuuuguaaa gcgccuaggg acccaagucg uaacgcucuu cguccgucaa    180

accccauuug uauccggaau ccaugacucu uaauucauaa guugaagcuc uacccacacu    240

aaagccuuuu caauguguuc uguuaccuuc ggagcuuauu cuuuuauccc auccggcuua    300

caucauuccc uuugacaguc ucgugcccuu agaacgguau accaugauuc ccaucacuua    360

ugaagcaggu gcucaagaaa uaugcaccau ggaccuuaau uccuuaauua uacauggucu    420

cccaaguaca cguacccaau aaagacaguc ggacccaccu                          460
```

<210> SEQ ID NO 44
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 44

```
uauauccccc uucucagccu cguacuuaaa ccguaaauua uuacaaucau uguuaucaau     60

auguauccaa ccaggccacu ucaucucgua aauccucacg auaccuacag aguaggcauc    120

ucugcgugug gcaugguaaa uugcccugcg acccaaaucg uuagucuccu aauccgucaa    180

aucccauuug uguccggaau ccuagacacg aaauggauau cuggaagcug aacccgcaca    240

aaaugcuuuu gcaggugcuc uuguagccuc ggcgucuacu cauuuauccc aucaugcaaa    300

caucauuucc augaacaguc ccauuccuua gaaauugaau gccauguuug ccaucaauuu    360

ggacgcagcu gcuacagaac uacgcucccu gcuagauacu ucguaaauuc uacgauguuu    420

ggccaguaca cguucccagg acacauaguc ucccgcaccu                          460
```

<210> SEQ ID NO 45
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 45

```
caaaacuucc cccucagccu ggacccuaua auguagauca uuccaaucau uguuaucaau     60

uuguauccac ccaggcuccu gcaugugguu aacucccucg auaccuccag aguaggcauc    120
```

```
ucugugugug ggaugguaaa ccgcccaacg acucaaaucg uaagccuccu cauccgucaa    180

aucccauuug uauccggaau ccaagacacc aaauacauaa auugaaccug aacccacacu    240

aaagacuuuu ccauguguuu ugguacccuc ggaguuuucu caaucaugcc auccugcuaa    300

cauuauuccc uuugacaguc ccauucccuu guaaugguau accauguuug ccgucauguu    360

ggaagcagcu gcuacacaac uaugcucccu guuccuuaac ucauacuucc uacaucguuu    420

ggccaguaca cggucgcaau aaacacagac ugccguaccu                          460


<210> SEQ ID NO 46
<211> LENGTH: 460
<212> TYPE: RNA
<213> ORGANISM: Artificial Sequence
<220> FEATURE:
<223> OTHER INFORMATION: Synthetic polynucleotide

<400> SEQUENCE: 46

caaaucuucc uucucagccu gguacuuaua auguaaauca uuccaaucau uguuaucaau     60

auguauccaa ccaguuuccu ucaagugaua aacccucaag auuccuccag aguaggcauc    120

ucugcgugug gcaugguaaa ucgcccugcg acccuaaucg uaagccuccu cauccuucaa    180

aucccauuug uauccggaau ccaagacauc aaaugcauaa gucgaaccug aacccccacu    240

aaagacuuuu ccagguguuc ugguacccuc ggaguuuacu ccuucauccc auccugcuua    300

caucauuccc aucgacaguc ccauucccuc guaauuguau accauguuug ccaccaauuu    360

ggaagcagcu gcuacagaac uacgcucccu guuccuuaau ucauacauuc uacauuguuu    420

ggccaguaca cggucccaau aaacacagcc ugccgcaaau                          460


<210> SEQ ID NO 47
<211> LENGTH: 200
<212> TYPE: RNA
<213> ORGANISM: Artificial Sequence
<220> FEATURE:
<223> OTHER INFORMATION: Synthetic polynucleotide

<400> SEQUENCE: 47

ucccauuugu auccggaauc caagacacca aaugcauaaa uugaaccuga acccacacua     60

aagacuuuuc cagguguucu gguacccucg gaguuuacuc uuuuauccca uccugcuaac    120

aucauuccca uugacagucc cauucccuug uaauuguaua ccauguuugc caucaauuug    180

gaagcagcug cuacagaaau                                                200


<210> SEQ ID NO 48
<211> LENGTH: 150
<212> TYPE: RNA
<213> ORGANISM: Artificial Sequence
<220> FEATURE:
<223> OTHER INFORMATION: Synthetic polynucleotide

<400> SEQUENCE: 48

caccaaaugc auaaauugaa ccugaaccca cacuaaagac uuuuccaggu guucugguac     60

ccucggaguu uacucuuuua ucccauccug cuaacaucau ucccauugac agucccauuc    120

ccuuguaauu guauaccaug uuugccauca                                     150


<210> SEQ ID NO 49
<211> LENGTH: 100
<212> TYPE: RNA
<213> ORGANISM: Artificial Sequence
<220> FEATURE:
```

-continued

```
<223> OTHER INFORMATION: Synthetic polynucleotide

<400> SEQUENCE: 49

acccacacua aagacuuuuc cagguguucu gguacccucg gaguuuacuc uuuuauccca     60

uccugcuaac aucauuccca uugacagucc cauucccuug                          100


<210> SEQ ID NO 50
<211> LENGTH: 50
<212> TYPE: RNA
<213> ORGANISM: Artificial Sequence
<220> FEATURE:
<223> OTHER INFORMATION: Synthetic polynucleotide

<400> SEQUENCE: 50

guucugguac ccucggaguu uacucuuuua ucccauccug cuaacaucau                50


<210> SEQ ID NO 51
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 51

cggaguuuac ucuuuuaucc caucc                                           25


<210> SEQ ID NO 52
<211> LENGTH: 74
<212> TYPE: DNA
<213> ORGANISM: Artificial Sequence
<220> FEATURE:
<223> OTHER INFORMATION: Synthetic polynucleotide

<400> SEQUENCE: 52

gggagaagat ctatgatgtt agcaggatgg gataaaagag taaactccga gggtaccaga     60

acggtacctc tccc                                                       74


<210> SEQ ID NO 53
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 53

gggagaagat ctggatggga taaaagagta aactccgggt acctctccc                 49
```

CONTROL OF INSECT INFESTATION

RELATED APPLICATION

This application claims the benefit under 35 U.S.C. § 119(e) of U.S. provisional application Ser. No. 62/757,217 filed Nov. 8, 2018, which is incorporated by reference herein in its entirety.

BACKGROUND

Crops are often the target of insect attacks. Globally, farmers lose 30 to 40 percent of their crops due to pests and diseases, according to the UN Food and Agricultural Organization.

Crop maintenance and crop health are essential for yield and quality of produce, which ultimately require long-term strategies for the minimization of pest and disease occurrence. The annual costs of controlling crop pests (e.g., Lepidoptera, Diptera, Coleoptera, Hemiptera, and others) are estimated to be in the tens of millions of dollars, with projected annual costs of crop loss reaching billions of dollars if left uncontrolled.

While chemical pesticides have been one solution for eradicating pest infestations, alternative, more environmentally safe, solutions are needed. Chemical pesticides are harmful to the environment and may lack specificity or selectivity which ultimately results in non-target effects. Additionally, given the slow metabolism of chemical pesticides and the likelihood of chemical pesticides to accumulate, resistance is likely to occur. Thus, there has been a long-felt need for more environmentally friendly methods for controlling or eradicating insect infestations which are more selective, environmentally safe, and biodegradable.

SUMMARY

The present disclosure provides, in some aspects, compositions, genetic constructs, and methods for controlling infestation of pests (e.g., insects of the order of Coleoptera, Lepidoptera, Hemiptera and/or Diptera) that cause damage to crop plants. For example, aspects of the present disclosure provide compositions that include interfering RNA molecules (e.g., double-stranded RNA) for controlling crop infestation by these pests. Aspects of the present disclosure further provide methods for controlling a pest including, but not limited to, killing the pest, inhibiting the growth and development of the pest, altering fertility or growth of the pest such that the pest provides less damage to a crop plant, decreasing the number of offspring produced by a pest, producing less fit pests, reducing insect infestation populations, producing pests more susceptible to predator attack, or deterring the pests from eating a crop plant. To reduce dependence on broad-spectrum chemical insecticides and their related problems, reduced-risk pesticides are required. A new technology that offers the promise of a reduced risk approach to insect pest control is RNA interference (RNAi). In some embodiments, the present disclosure provides RNAi-based technologies that can mitigate insect (e.g., Colorado potato beetle damage by delivering ribonucleic acid (RNA) interference (RNAi) molecules that target (e.g., bind to) and interfere with the messenger RNA (mRNA) of an insect (e.g., Colorado potato beetle proteasome beta 5 (PSMB5) gene.

Proteasome beta 5, which is a subunit of the proteasome (a complex responsible for degradation of intracellular proteins), primarily affects endopeptidase activity through the catalysis of the hydrolysis of internal, alpha-peptide bonds in a polypeptide chain. Proteasome beta 5 has lethal and complex phenotypes involving disruption of multiple aspects of physiology including the chemical reactions and pathways resulting in the breakdown of a protein or peptide by hydrolysis of its peptide bonds, initiated by the covalent attachment of ubiquitin, and mediated by the proteasome.

Laboratory studies have confirmed that oral delivery of RNA molecules whose mode of action is through the RNAi process (e.g., double-stranded RNA (dsRNA)) are effective for many insect species and hence, topical dsRNA is considered a suitable form of delivery. However, spray-on dsRNA insect pest control technology does not exist today. The cost of production of dsRNA at a relatively low price is a major challenge for the Ag-Bio industry. For agricultural pests, transgenic plants that can express insecticidal dsRNA may protect the plants from insect herbivory. However, not all countries are receptive to genetically-modified crops, and spray-on application of dsRNA is being considered as an alternative delivery method of protection.

To identify targets for RNAi knockdown, whole genome information was used to identify the appropriate gene sequence for PSMB5 in the target species (e.g., *Leptinotarsa decemlineata*), which when silenced selectively, controls these key pests, without adversely affecting non-target species in the potato agriculture ecosystem. Given a DNA sequence of interest and a rule set of design criteria for the output sequences, a propriety computational algorithm was combined with publicly available RNAi design tools, to create output sequences that meet these criteria. The original/initial region selected to design the dsRNA was identified by searching comprehensive sequence databases for *Tribolium* and *Drosophila* genomes (e.g., Flybase, SnapDragon, Beetlebase, etc.). The publicly available E-RNAi tool, that can be used to design dsRNA using a predicted siRNA-based approach, was combined with proprietary algorithms to create the design workflow. This design workflow was then used to create specific long dsRNA sequences of a (a) desired length (b) desired percent identity to original sequence (by introducing random mutations), and (c) by sectioning the initial PSMB5 gene sequence into multiple fragments.

In some embodiments, the RNAi molecules comprise single-stranded RNA (ssRNA), and in some embodiments, the RNAi molecules comprise double-stranded RNA (dsRNA) or partially dsRNA. In still other embodiments, the RNAi molecules may be single-stranded RNA molecules with secondary structure containing significant double-stranded character, such as, but not limited to, hairpin RNA. The present disclosure provides RNA, for example single stranded RNA (ssRNA), small interfering RNA (siRNA), micro RNA (miRNA), messenger RNA (mRNA), short hairpin RNA (shRNA) or double stranded RNA (dsRNA) for targeting PSMB5 mRNA.

PSMB5 RNA, in some embodiments, is effective for reducing PSMB5 expression in an insect, stunting of larvae, inhibiting growth, reproduction (e.g., fertility and/or fecundity) and/or repair of the insect, killing of the larvae or the insect, and decreasing feeding of the insect. Accordingly, one aspect of the present disclosure provides a method for controlling an insect comprising delivering (e.g., contacting) an effective amount of a PSMB5-targeting RNA with a plant and/or an insect. PSMB5 RNA is particularly useful for controlling a Coleopteran insect (e.g., Colorado potato beetle), thereby reducing and/or preventing infestation of certain plants (e.g., a potato) that are a major food source for humans.

Some aspects of the present disclosure also provide cell-free methods of producing PSMB5-targeting RNA, the method comprising: (a) incubating in a reaction mixture cellular RNA, and a ribonuclease under conditions appropriate for the production of 5' nucleoside monophosphates (5' NMPs); (b) eliminating the ribonuclease; and (c) incubating the reaction mixture, or in a second reaction mixture, the 5' NMPs, a polyphophospate kinase, a polyphosphate, a polymerase, and a DNA (also referred to a DNA template) under conditions appropriate for the production of the PSMB5-targeting RNA from the DNA.

Also provided herein are compositions comprising a PSMB5-targeting RNA. In some embodiments, the composition comprising a PSMB5-targeting RNA further comprises an additive, for example, a chemical, a pesticide, a surfactant, a biological, or other non-pesticidal ingredient. In some embodiments, PSMB5-targeting RNA is provided in an expression vector. In some embodiments, a PSMB5-targeting RNA is provided in a plant or a plant cell.

It should be understood that an "RNAi molecule targeting PSMB5" encompasses "RNAi molecules targeting mRNA encoded by PSMB5." A RNAi molecule is considered to target a gene of interest if the RNAi molecule binds to (e.g., transiently binds to) and inhibits (reduces or blocks) translation of the mRNA, e.g., due to the mRNA being degraded. In some embodiments, if there are epigenetic changes, a RNAi molecule may inhibit expression of the mRNA encoded by the gene of interest. It should also be understood that in some embodiments, the polynucleotide is a double-stranded RNA (e.g., dsRNA) that inhibits expression of a coding region of the gene (e.g., PSMB5). In other embodiments, the polynucleotide is a DNA sequence that encodes a dsRNA. In yet other embodiments, the polynucleotide is an antisense RNA. It should be understood that the sequences disclosed herein as DNA sequences can be converted from a DNA sequence to an RNA sequence by replacing each thymidine with a uracil.

DETAILED DESCRIPTION

Figure 1A:
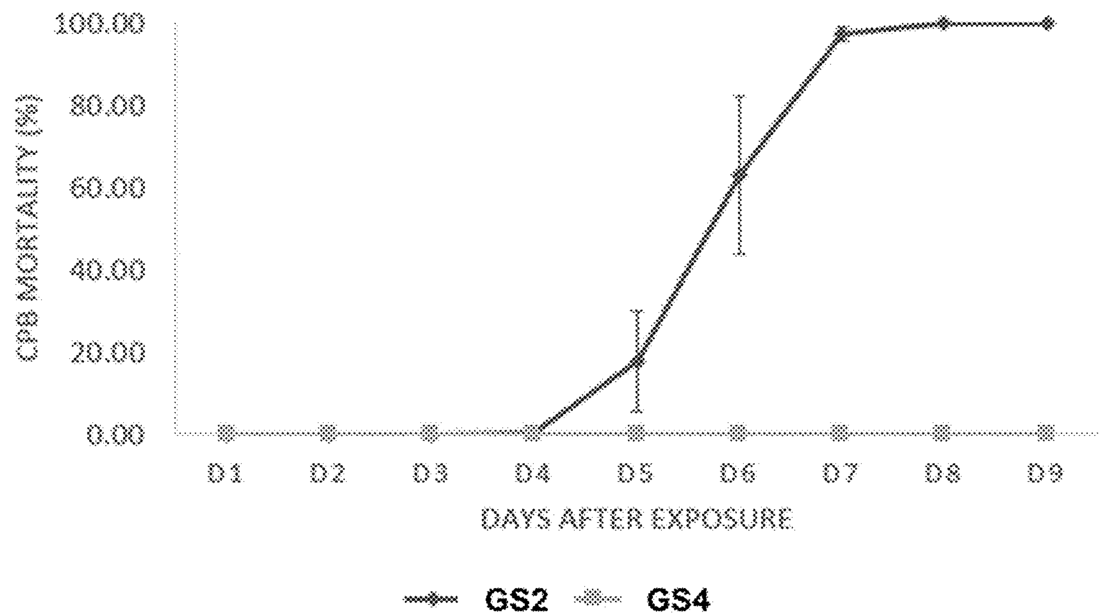
FIGS. 1A-1B include graphs showing the percent mortality of Colorado potato beetles (CPBs) (FIG. 1A) and percent leaf disc consumption by CPBs (FIG. 1B) following a nine-day exposure of the CPBs to either a PSMB5 RNAi (GS2) composition of the present disclosure or to a control RNAi (GS4) composition (10 μg/cm$^2$ concentration of RNAi).

According to some aspects of the present disclosure, RNAi molecules (e.g., dsRNAs) targeting PSMB5 are effective at interfering with the mRNA encoded by a PSMB5 gene in insect (e.g. Coleopteran) cells, thereby reducing or eliminating translation of the mRNA (e.g., into its corresponding protein). Accordingly, in some aspects, the present disclosure provides compositions and methods for controlling insect (e.g. Coleopteran) infestations by contacting any portion of a plant (e.g., roots, tubers, stem, branches, leaves, flower, etc.), ground (e.g., soil, dirt, grass, etc.), insect (e.g., Coleopteran) and/or diet (e.g., food and/or water ingested by) of the insect with an RNAi molecule as provided herein.

Also provided herein are cell-free methods of synthesizing RNAi molecules that target PSMB5 gene products (mRNA).

An insect, as used herein, refers to an insect in any stage of development. In some embodiments, the insect is an insect egg. In some embodiments, the insect is an insect larva. In some embodiments, the insect is an insect pupa. In some embodiments, the insect is an adult insect.

A Lepidopteran insect may be any Lepidopteran insect of order Lepidoptera. Examples of insects of the order Lepidoptera include, but are not limited to, Nymphalidae (brush-footed butterflies), Danaidae (milkweed butterflies), Pieridae (whites and sulfurs) Papilionidae (swallowtails), Lycaenidae (blues, coppers, and hairstreaks), Hesperiidae (skippers), Tineidae (clothes moths), Sesiidae (clearwing moths), Pyralidae (snout moths), Lasiocampidae (lappet moths), Saturniidae (giant silk moths), Sphingidae (hawk moths), Arctiidae (tiger moths), Lymantriidae (tussock moths), Noctuidae (loopers, owlet moths, and underwings).

A Dipteran insect may be any Dipteran insect of order Diptera. Examples of insects of the order Diptera include, but are not limited to, Culicidae (mosquitoes), Tabanidae (horse flies/deer flies), Simuliidae (black flies), Psychodidae (moth flies), Ceratopogonidae (punkies, no-see-ums), Muscidae (House flies), Cecidomyiidae (gall midges), Tephritidae (fruit flies), Agromyzidae (leaf miners), Anthomyiidae (maggots), Drosophilidae (pomace flies), Tipulidae (crane flies), Calliphoridae (blow flies), Chironomidae (midges), and Sarcophagidae (flesh flies)

A Hemipteran insect may be a Hemipteran insect of order Hemiptera. Examples of insects of the order of Hemiptera include, but are not limited to Miridae (Plant Bugs), Lygaeidae (Seed Bugs), Tingidae (lace bugs), Coreidae (squash bugs and leaf-footed bugs), Alydidae (broad-headed bugs), Rhopalidae (scentless plant bugs), Berytidae (stilt bugs), Reduviidae (assassin bugs), Phymatidae (ambush bugs), Nabidae (damsel bugs), Anthocoridae (minute pirate bugs), Corixidae (water boatmen), Gerridae (water striders), Nepidae (water scorpions), Belostomatidae (giant water bugs), Naucoridae (creeping water bugs), Notonectidae (backswimmers), Cicadidae (cicadas), Cicadellidae (leafhoppers), Membracidae (treehoppers), Cercopidae (spittlebugs or froghoppers), Fulgoridae (planthoppers), Psyllidae (psyllids or jumping plant lice), Aleyrodidae (whiteflies), Aphididae (aphids, plant lice), and Coccidae (soft scale insects).

A Coleopteran insect may be any Coleopteran insect of order Coleoptera. Examples of insects of the order Coleoptera include, but are not limited to, Chrysomelidae (leaf beetle, broad-shouldered leaf beetle, alligator weed flea beetle), Curculionidae (snout beetle), Meloidae (blister beetle), Tenebrionidae (darkling beetle), Scarabaeidae (scarab beetle), Cerambycidae (Japanese pine sawyer), Curculionidae (Chinese white pine beetle), Nitidulidae (small hive beetle), Cerambycidae (mulberry longhorn beetle), Phyllotreta (flea beetle), Diabrotica (corn rootworm) *Chrysomela* (cottonwood leaf beetle), *Hypothenemus* (coffee berry borer), *Sitophilus* (maize weevil), Epitrix (tobacco flea beetle), *E. cucumeris* (potato flea beetle), *P. pusilla* (western black flea beetle); *Anthonomus* (pepper weevil), Hemicrepidus (wireworms), *Melanotus* (wireworm), Ceutorhychus (cabbage seedpod weevil), *Aeolus* (wireworm), Horistonotus (sand wireworm), *Sphenophorus* (maize billbug), *S. zea* (timothy billbug), *S. parvulus* (bluegrass billbug), *S. callosus* (southern corn billbug); *Phyllophaga* (white grubs), *Chaetocnema* (corn flea beetle), Popillia (Japanese beetle), Epilachna (Mexican bean beetle), Cerotoma (bean leaf beetle), Epicauta (blister beetle), and any combination thereof.

Further, the Coleopteran insect may be any species of *Leptinotarsa*. *Leptinotarsa* species include, but are not limited to, *Leptinotarsa decemlineata* (Colorado potato beetle), *Leptinotarsa juncta* (False potato Beetle), *Leptinotarsa behrensi, Leptinotarsa collinsi, Leptinotarsa defecta, Leptinotarsa haldemani* (Haldeman's green potato beetle), *Leptinotarsa heydeni, Leptinotarsa juncta* (false potato beetle), *Leptinotarsa lineolata* (burrobrush leaf beetle), *Leptinotarsa peninsularis, Leptinotarsa rubiginosa, Leptinotarsa texana, Leptinotarsa tlascalana, Leptinotarsa tumamoca*, and *Leptinotarsa typographica.*

RNAi Molecule Targeting Proteasome Beta 5 (PSMB5)

RNAi molecules targeting PSMB5 have been identified through examination of PSMB5 mRNA, in vitro and in vivo (e.g., plant/field) testing. Such RNAi molecules targeting PSMB5 are useful for controlling Coleopteran insects (e.g., Colorado potato beetles), for example, by inhibiting or reducing expression of PSMB5, and consequently, by increasing insect mortality, as well as decreasing growth, reproduction (e.g., fertility and/or fecundity), and/or feeding (e.g., eating and/or drinking) of Coleopteran insects.

Expression of a gene in a cell (e.g., insect cell), for example, is considered to be inhibited or reduced through contact with an RNAi molecule if the level of mRNA and/or protein encoded by the gene is reduced in the cell by at least 10% relative to a control cell that has not been contacted with the RNAi molecule. For example, delivering to a cell (e.g., contacting a cell) with an RNAi molecule (e.g., dsRNA) targeting PSMB5 may result in a reduction (e.g., by at least 10%) in the amount of RNA transcript and/or protein (e.g., encoded by the PSMB5 gene) compared to a cell that is not contacted with RNAi molecular targeting PSMB5.

In some embodiments, RNAi molecules of the present disclosure specifically inhibit expression of a PSMB5 gene without biologically relevant or biologically significant off-target effects (no relevant or significant change in the expression of non-PSMB5 genes). In some embodiments, an RNAi molecule specifically inhibits (reduces or blocks) translation of a PSMB5 protein by specifically inhibiting expression of (e.g., degrading) a PSMB5 mRNA (e.g., PSMB5 mRNA of SEQ ID NO: 18) that encodes the PSMB5 protein. Specific inhibition of a PSMB5 gene includes a measurable reduction in PSMB5 gene expression (e.g., PSMB5 mRNA expression, and/or PSMB5 protein expression) or a complete lack of detectable gene expression (e.g., PSMB5 mRNA expression, and/or PSMB5 protein expression).

In some embodiments, RNAi molecules of the present disclosure specifically inhibit expression of a PSMB5 gene without biologically relevant or biologically significant off-target effects (no relevant or significant change in the expression of non-PSMB5 genes). In some embodiments, an RNAi molecule specifically inhibits the expression of a PSMB5 protein by specifically inhibiting an mRNA that encodes a PSMB5 protein (e.g., PSMB5 mRNA of SEQ ID NO: 18). Specific inhibition of a PSMB5 gene involves a measurable reduction in PSMB5 gene expression (e.g., PSMB5 mRNA expression, and/or PSMB5 protein expression) or a complete lack of detectable gene expression (e.g., PSMB5 mRNA expression, and/or PSMB5 protein expression).

RNAi molecules targeting PSMB5 provided herein, in some embodiments, are designed to have complementarity to PSMB5 mRNA of a Coleopteran insect, e.g., a Colorado potato beetle. An example of a DNA sequence encoding Colorado potato beetle PSMB5 is provided in the sequence of SEQ ID NO: 1. An example of an mRNA sequence encoding Colorado potato beetle PSMB5 is provided in the sequence of SEQ ID NO: 18. Examples of Colorado potato beetle PSMB5 mRNA sequences targeted by an RNAi molecule of the present disclosure encoding are provided in the sequences of SEQ ID NO: 18, 19, and 21-23. Examples of a RNA molecules targeting PSMB5 are provided in the sequences of SEQ ID NO: 35, 36, and 38-51.

In some embodiments, the RNAi molecule targeting PSMB5 provided herein is designed to have complementarity to PSMB5 mRNA of a Coleopteran insect, e.g., a Chrysomelidae (a leaf beetle), a Curculionidae (a snout beetle), a Meloidae (a blister beetle), Tenebrionidae (a darkling beetle), a Scarabaeidae (a scarab beetle), a Cerambycidae (a Japanese pine sawyer), a Curculionidae (a Chinese white pine beetle), a Nitidulidae (a small hive beetle), a Chrysomelidae (a broad-shouldered leaf beetle), a Cerambycidae (a mulberry longhorn beetle), *C. scripta* (cottonwood leaf beetle), *H. hampei* (coffee berry borer), *S. Zeamais* (maize weevil), *F. hirtipennis* (tobacco flea beetle), *F. cucumeris* (potato flea beetle), *P. cruciferae* (crucifer flea beetle) and *P. pusilla* (western black flea beetle), *A. eugenii* (pepper weevil), *H. memnonius* (wireworms), *M. communis* (wireworm), *C. assimilis* (cabbage seedpod weevil), *P. striolata* (striped flea beetle), *A. mellillus* (wireworm), *A. mancus* (wheat wireworm), *H. uhlerii* (sand wireworm), *S. maidis* (maize billbug), *S. zea* e (timothy billbug), *S. parvulus* (bluegrass billbug), and *S. callosus* (southern corn billbug), *Phyllophaga* spp. (White grubs), *C. pulicaria* (corn flea beetle), *P. japonica* (Japanese beetle), *F. varivestis* (Mexican bean beetle), *C. trifurcate* (Bean leaf beetle), *F. pestifera* and *F. lemniscata* (Blister beetles), *Oulema melanapus* (Cereal leaf beetle), *Hypera postica* (Alfalfa weevil), *Dendroctonus* (Mountain Pine beetle), *Agrilus* (Emerald Ash Borer), *Hylurgopinus* (native elm bark beetle), *Scolytus* (European elm bark beetle) and/or a Chrysomelidae (an alligator weed flea beetle).

In some embodiments, the RNAi molecule targeting PSMB5 provided herein is designed to have complementarity to PSMB5 mRNA of a *Leptinotarsa* insect, e.g., a *Leptinotarsa decemlineata* (a Colorado potato beetle), a *Leptinotarsa behrensi*, a *Leptinotarsa collinsi*, a *Leptinotarsa defecta*, a *Leptinotarsa haldemani* (a Haldeman's green potato beetle), a *Leptinotarsa heydeni*, a *Leptinotarsa juncta* (a false potato beetle), a *Leptinotarsa lineolata* (a burrobrush leaf beetle), a *Leptinotarsa peninsularis*, a *Leptinotarsa rubiginosa*, a *Leptinotarsa texana*, a *Leptinotarsa tlascalana*, a *Leptinotarsa tumamoca*, and/or a *Leptinotarsa typographica*.

A double-stranded RNA (dsRNA) of the present disclosure, in some embodiments, comprises a first strand that binds to (e.g., is at least partially complementary to or is wholly complementary to) a messenger RNA (mRNA) encoded by a Coleoptera PSMB5 gene, and a second strand that is complementary to the first strand.

dsRNA may comprise RNA strands that are the same length or different lengths. In some embodiments, a dsRNA comprises a first strand (e.g., an antisense strand) that is the same length as a second strand (e.g., a sense strand). In some embodiments, a dsRNA comprises a first strand (e.g., an antisense strand) that is a different length than a second strand (e.g., a sense strand). A first strand may be about 1%, 2%, 3%, 4%, 5%, 10%, 15%, 20%, or more than 20% longer than a second strand. A first strand may be 1-5, 2-5, 2-10, 5-10, 5-15, 10-20, 15-20, or more than 20 nucleotides longer than a second strand.

dsRNA molecules can also be assembled from a single oligonucleotide in a stem-loop structure, wherein self-complementary sense and antisense regions of the RNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active RNAi molecule capable of mediating RNAi. An RNAi molecule may comprise a 3' overhang at one end of the molecule; the other end may be blunt-ended or have also an overhang (5' or 3'). When the RNAi molecule comprises an overhang at both ends of the molecule, the length of the overhangs may be the same or different.

A single-stranded RNA of the present disclosure, in some embodiments, comprises a strand that binds to a mRNA encoded by a Coleoptera PSMB5 gene.

RNAi molecules targeting PSMB5 as provided herein may vary in length. It should be understood that, in some embodiments, while a long RNA (e.g., dsRNA or ssRNA) molecule is applied (e.g., to a plant) as the insecticide, after entering cells the dsRNA is cleaved by the Dicer enzyme into shorter double-stranded RNA fragments having a length of, for example, 15 to 25 nucleotides. Thus, RNAi molecules of the present disclosure may be delivered as 15 to 25 nucleotide fragments, for example, or they may be delivered as longer double-stranded nucleic acids (e.g., at least 100 nucleotides).

Thus, in some embodiments, RNAi molecules targeting PSMB5 comprise 15-1010 nucleotides (ssRNA) or nucleotide base pairs (dsRNA). For example, an RNAi molecule of the present disclosure may comprise 15-1000, 15-950, 15-900, 15-850, 15-800, 15-750, 15-700, 15-650, 15-600, 15-500, 15-450, 15-400, 15-350, 15-300, 15-250, 15-200, 15-150, 15-100, 15-50, 16-1000, 16-950, 16-900, 16-850, 16-800, 16-750, 16-700, 16-650, 16-600, 16-500, 16-450, 16-400, 16-350, 16-300, 16-250, 16-200, 16-150, 16-100, 16-50, 17-1000, 17-950, 17-900, 17-850, 17-800, 17-750, 17-700, 17-650, 17-600, 17-500, 17-450, 17-400, 17-350, 17-300, 17-250, 17-200, 17-150, 17-100, 17-50, 18-1000, 18-950, 18-900, 18-850, 18-800, 18-750, 18-700, 18-650, 18-600, 18-500, 18-450, 18-400, 18-350, 18-300, 18-250, 18-200, 18-180, 18-100, 18-50, 19-1000, 19-950, 19-900, 19-850, 19-800, 19-750, 19-700, 19-650, 19-600, 19-500, 19-450, 19-400, 19-350, 19-300, 19-250, 19-200, 19-190, 19-100, 19-50, 20-1000, 20-950, 20-900, 20-850, 20-800, 20-750, 20-700, 20-650, 20-600, 20-500, 20-450, 20-400, 20-350, 20-300, 20-250, 20-200, 20-200, 20-100, 20-50, 21-1000, 21-950, 21-900, 21-850, 21-800, 21-750, 21-700, 21-650, 21-600, 21-500, 21-450, 21-400, 21-350, 21-300, 21-250, 21-210, 21-210, 21-100, 21-50, 22-1000, 22-950, 22-900, 22-850, 22-800, 22-750, 22-700, 22-650, 22-600, 22-500, 22-450, 22-400, 22-350, 22-300, 22-250, 22-220, 22-220, 22-100, 22-50, 23-1000, 23-950, 23-900, 23-850, 23-800, 23-750, 23-700, 23-650, 23-600, 23-500, 23-450, 23-400, 23-350, 23-300, 23-250, 23-230, 23-230, 23-100, 23-50, 24-1000, 24-950, 24-900, 24-850, 24-800, 24-750, 24-700, 24-650, 24-600, 24-500, 24-450, 24-400, 24-350, 24-300, 24-250, 24-240, 24-240, 24-100, 24-50, 25-1000, 25-950, 25-900, 25-850, 25-800, 25-750, 25-700, 25-650, 25-600, 25-500, 25-450, 25-400, 25-350, 25-300, 25-250, 25-250, 25-250, 25-100, or 25-50 nucleotides or nucleotide base pairs. In some embodiments, RNAi molecules targeting PSMB5 comprise or consist of at least 15, at least 16, at least 17, at least 18, at least 19, at least 20, at least 25, at least 50, at least 200, at least 300, at least 400, at least 500, at least 600, at least 700, at least 800, at least 900, or at least 1000 nucleotides or nucleotide base pairs.

In some embodiments, an RNAi molecule targeting PSMB5 comprises or consists of a sequence that is complementary to an mRNA or a segment of an mRNA encoded by a Coleoptera PSMB5 gene. In some embodiments, an RNAi molecule targeting PSMB5 comprises or consists of a sequence that is complementary to an mRNA or a segment of an mRNA encoded by a DNA sequence of SEQ ID NO: 1. In some embodiments, an RNAi molecule targeting PSMB5 comprises or consists of a sequence that is complementary to an mRNA encoded by a DNA sequence of SEQ ID NO: 1.

In some embodiments, an RNAi molecule targeting PSMB5 comprises or consists of a sequence that is complementary to an mRNA encoded by a region or segment of a Coleoptera PSMB5 DNA. In some embodiments, an RNAi molecule targets an mRNA encoded by a region of a Coleoptera PSMB5 DNA that may comprise or consist of any sequence encompassed by nucleotides 1 to 500, nucleotides 10 to 500, nucleotides 25 to 500, nucleotides 50 to 500, nucleotides 100 to 500, nucleotides 150 to 500, nucleotides 200 to 500, nucleotides 250 to 500, nucleotides 300 to 500, nucleotides 350 to 500, nucleotides 400 to 500, or nucleotides 450 to 500 of the PSMB5 DNA (e.g., nucleotides 1-450 of SEQ ID NO: 1). In some embodiments, an RNAi molecule targets an mRNA encoded by a region of a Coleoptera PSMB5 DNA that may comprise or consist of any sequence encompassed by nucleotides 200 to 950, nucleotides 250 to 950, nucleotides 300 to 950, nucleotides 350 to 950, nucleotides 400 to 950, nucleotides 450 to 950, nucleotides 500 to 950, nucleotides 550 to 950, nucleotides 200 to 700, nucleotides 250 to 700, nucleotides 300 to 700, nucleotides 350 to 700, nucleotides 400 to 700, nucleotides 450 to 700, nucleotides 500 to 700, nucleotides 550 to 700, nucleotides 600 to 700, or nucleotides 650 to 700 of the PSMB5 DNA (e.g., nucleotides 450-927 of SEQ ID NO: 1). In some embodiments, an RNAi molecule targets an mRNA encoded by a region or segment of a Coleoptera PSMB5 DNA that may comprise or consist of any sequence encompassed by nucleotides 400 to 1010, nucleotides 4500 to 1010, nucleotides 500 to 1010, nucleotides 550 to 1010, nucleotides 600 to 1010, nucleotides 650 to 1010, nucleotides 700 to 1010, nucleotides 750 to 1010, nucleotides 800 to 1010, nucleotides 850 to 1010, nucleotides 900 to 1010, or nucleotides 950 to 1010 of the PSMB5 DNA (e.g., nucleotides 450-1010 of SEQ ID NO: 1).

It should be understood that the term gene encompasses coding and non-coding nucleic acid. Thus, in some embodiments, a PSMB5 gene encodes an mRNA that comprises a 5' untranslated region, an open reading frame, and a 3' untranslated region. Thus, an RNAi molecule herein, in some embodiments, binds to a 5' untranslated region, an open reading frame, and/or a 3' untranslated region of an mRNA.

In some embodiments, an RNAi molecule targeting PSMB5 comprises or consists of an RNA sequence of any one of SEQ ID NO: 18, 19, or 21-34. In some embodiments, an RNAi molecule targeting PSMB5 comprises or consists of an RNA sequence of SEQ ID NO: 19.

In some embodiments, an RNAi molecule targeting PSMB5 comprises or consists of a sequence that is complementary to a RNA sequence of any one of SEQ ID NO: 35, 36 and 38-51. In some embodiments, an RNAi molecule targeting PSMB5 comprises or consists of a sequence that is complementary to a RNA sequence of SEQ ID NO: 36.

In some embodiments, RNAi molecules targeting PSMB5 comprise or consist of a (at least one) contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence encoded by a Coleoptera PSMB5 gene. In some embodiments, the PSMB5 gene comprises a DNA sequence of SEQ ID NO: 1. In some embodiments, RNAi molecules targeting PSMB5 comprise or consist of a (at least one) contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence encoded by a DNA sequence of SEQ ID NO: 1.

In some embodiments, RNAi molecules targeting PSMB5 comprise or consist of a (at least one) contiguous sequence that is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence encoded by a Coleoptera PSMB5 gene. In some embodiments, the PSMB5 gene comprises a DNA sequence of SEQ ID NO: 1. In some embodiments, RNAi molecules targeting PSMB5 comprise or consist of a (at least one) contiguous sequence that is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence encoded by a DNA sequence of any one of SEQ ID NOS: 1, 2, and 4-17.

In some embodiments, RNAi molecules targeting PSMB5 comprise or consist of a (at least one) contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence of any one of SEQ ID NOS: 35, 36, and 38-51. In some embodiments, RNAi molecules targeting PSMB5 comprise or consist of a contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence of SEQ ID NO: 36.

In some embodiments, RNAi molecules targeting PSMB5 comprise or consist of a (at least one) contiguous sequence is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence of any one of SEQ ID NOS: 18, 19, and 21-23. In some embodiments, RNAi molecules targeting PSMB5 comprise or consist of a contiguous sequence is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence of SEQ ID NO: 19.

In some embodiments, RNAi molecules targeting PSMB5 comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of any one of SEQ ID NOS: 35, 36, and 38-51. In some embodiments, RNAi molecules targeting PSMB5 comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of SEQ ID NO: 36.

In some embodiments, RNAi molecules targeting PSMB5 comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of any one of SEQ ID NOS: 18, 19, and 21-23. In some embodiments, RNAi molecules targeting PSMB5 comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of SEQ ID NO: 19.

In some embodiments, RNAi molecules targeting PSMB5 comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of any one of SEQ ID NOS: 35, 36, and 38-51. In some embodiments, RNAi molecules targeting PSMB5 comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of SEQ ID NO: 36.

In some embodiments, RNAi molecules targeting PSMB5 comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of any one of SEQ ID NOS: 18, 19, and 21-23. In some embodiments, RNAi molecules targeting PSMB5 comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of SEQ ID NO: 36.

The "percent identity" of two nucleic acid sequences (e.g., RNAi molecules targeting PSMB5 provided herein and any one of, for example, SEQ ID NOS: 35, 36, and 38-51) may be determined by any method known in the art. The variants provided herein, in some embodiments, contain randomly placed mutations with the four nucleotides (A, U, G, C) selected at an approximately equal probability for a given mutation. In some embodiments, these mutations might be distributed either over a small region of the sequence, or widely distributed across the length of the sequence. In some embodiments, the percent identity of two nucleic acid sequences is determined using the algorithm of Karlin and Altschul, *Proc. Natl. Acad. Sci. USA* 87:2264-68, 1990, modified as in Karlin and Altschul, *Proc. Natl. Acad. Sci. USA* 90:5873-77, 1993. Such an algorithm is incorporated into the NBLAST and XBLAST programs (version 2.0) of Altschul et al. *J. Mol. Biol.* 215:403-10, 1990. BLAST nucleotide searches can be performed with the NBLAST program, score=100, wordlength-12 to obtain guide sequences homologous to a target nucleic acid. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NB LAST) can be used.

The polynucleotides provided herein, such as RNAi molecules targeting PSMB5, in some embodiments, are designed to have at least one silencing element complementary (e.g., wholly (100%) or partially (less than 100%, e.g., 90% to 99%) complementary) to a segment of a sequence of PSMB5 mRNA of a Coleopteran insect, e.g., a Colorado potato beetle. In some embodiments, polynucleotides comprise at least one silencing element that is essentially identical or essentially complementary to PSMB5 mRNA of a Coleopteran insect. In some embodiments, the polynucleotides comprise 2 to 5, to 10, 2 to 20, 2 to 20, 2 to 40, or 2 to 50 silencing elements. In some embodiments, the polynucleotides comprise at least 2, at least 3, at least 4, at least 5, at least 6, at least 7, at least 8, at least 9, at least 10, at least 15, at least 20, at least 25, at least 30, at least 35, at least 40, at least 45 or at least 50 silencing elements.

RNAi molecules targeting PSMB5 provided herein may be of any form of RNA, including single-stranded RNA (ssRNA) and double-stranded RNA (dsRNA). Non-limiting examples of single-stranded RNA include mRNA, micro RNA (miRNA) (e.g., artificial miRNA (amiRNA)), small interfering RNA (siRNA), piwi-interacting RNA (piRNA), and antisense RNA. Double-stranded RNA includes wholly double-stranded molecules that do not contain a single-stranded region (e.g., a loop or overhang), as well as partially double-stranded molecules that contain a double-stranded region and a single-stranded region (e.g., a loop or overhang). Further, the RNAi molecules may be single-stranded RNA molecules with secondary structure containing significant double-stranded character, such as, but not limited to, hairpin RNA. Thus, RNAi molecules targeting PSMB5, in some embodiments, may be short hairpin RNA (shRNA).

In some embodiments, RNAi molecules targeting PSMB5 comprise dsRNA, ssRNA, siRNA, miRNA (e.g., amirRNA), piRNA, mRNA, or shRNA. In some embodiments, RNAi molecules targeting PSMB5 comprise more than one form of RNA. For example, the RNAi molecules targeting PSMB5 may comprise ssRNA and dsRNA. In some embodiments, RNAi molecules targeting PSMB5 comprise a hybrid with RNA and DNA. In some embodiments, RNAi molecules targeting PSMB5 comprise amiRNAs processed from a long precursor transcript of nonprotein-coding RNA, that is partially self-complementary to mediate silencing of target mRNAs. amiRNAs are designed, in some embodiments, by replacing the mature 21 nucleotide miRNA sequences within pre-miRNA with 21 nucleotide long fragments derived from the target gene (*Frontiers in* Plant Science, Sebastian et al., 2017). An amiRNA may have a length of, for example, at least 18 to 500 nucleotides, at least 21 to 500 nucleotides, at least 50 to 500 nucleotides, at least 100 to 500 nucleotides, or at least 200 to 500 nucleotides.

RNAi molecules targeting PSMB5 may be provided as a mixture of RNAi molecules targeting PSMB5, for example, a mixture of RNAi molecules targeting PSMB5 having different sequences. Any number of distinct RNAi molecules targeting PSMB5 may be provided in a mixture of RNAi molecules targeting PSMB5. In some embodiments, the mixture of RNAi molecules targeting PSMB5 comprises at least 2, at least 3, at least 4, at least 5, at least 6, at least 7, at least 8, at least 9, or at least 10 distinct (having different sequences/nucleotide compositions) RNAi molecules targeting PSMB5.

In some embodiment, RNAi molecules targeting PSMB5 are provided as a mixture of RNAi molecules that are complementary (wholly or partially) to different segments of an mRNA encoded by a PSMB5 gene (e.g., comprising a sequence of SEQ ID NO: 1). In some embodiment, RNAi molecules targeting PSMB5 are provided as a mixture of RNAi molecules that are complementary (wholly or partially) to different segments of an RNA sequence of SEQ ID NO: 18. Any number of RNAi molecules targeting PSMB5 that are complementary to different segments of an mRNA (e.g., comprising a sequence of SEQ ID NO: 18) encoded by a PSMB5 gene (e.g., comprising a sequence of SEQ ID NO: 1) may be provided in a mixture of RNAi molecules targeting PSMB5. In some embodiments, the mixture of RNAi molecules targeting PSMB5 comprises at least 2, at least 3, at least 4, at least 5, at least 6, at least 7, at least 8, at least 9, or at least 10 RNAi molecules targeting PSMB5. In some embodiments, the mixture of RNAi molecules targeting PSMB5 comprises 2 to 5, or 2 to 10 RNAi molecules targeting PSMB5.

In some embodiments, RNAi molecules targeting PSMB5 provided herein may have one or more mismatches compared with the corresponding sequence of PSMB5 mRNA (e.g., SEQ ID NO: 18). A region of complementarity on RNAi molecule targeting PSMB5 may have up to 1, up to 2, up to 3, up to 4, etc. mismatches provided that it maintains the ability to form complementary base pairs with PSMB5 mRNA under appropriate hybridization conditions. Alternatively, a region of complementarity on RNAi molecules targeting PSMB5 may have no more than 1, no more than 2, no more than 3, or no more than 4 mismatches provided that it maintains the ability to form complementary base pairs with PSMB5 mRNA under appropriate hybridization conditions. In some embodiments, if there is more than one mismatch in a region of complementarity, they may be positioned consecutively (e.g., 2, 3, 4, or more in a row), or interspersed throughout the region of complementarity provided that the RNAi molecule targeting PSMB5 maintains the ability to form complementary base pairs with PSMB5 mRNA under appropriate hybridization conditions.

RNAi molecules targeting PSMB5 may be modified in various ways to improve or control specificity, stability, delivery, bioavailability, degradation, resistance to nuclease degradation, base-pairing properties, RNA distribution, and cellular uptake, and other features relevant to its use. See, e.g., Bramsen et al., *Nucleic Acids Res.,* 2009, 37, 2867-2881; Bramsen and Kjems, *Frontiers in Genetics,* 3 (2012): 1-22. Accordingly, in some embodiments, RNAi molecules targeting PSMB5 may include one or more (at least one) suitable modifications. In some embodiments, a modified RNAi molecule targeting PSMB5 has a modification in its base, sugar (e.g., ribose, deoxyribose), or phosphate group.

RNAi molecules targeting PSMB5 produced by the methods provided herein may be modified as described herein. In some embodiments, RNAi molecules targeting PSMB5 is produced according to a method described herein and subsequently modified. In some embodiments, RNAi molecules targeting PSMB5 are produced according to a method described herein using a modified starting material. In some embodiments, the modified starting material is a modified nucleobase. In some embodiments, the modified starting material is a modified nucleoside. In some embodiments, the modified starting material is a modified nucleotide.

In some embodiments, modified RNAi molecules targeting PSMB5 comprise a backbone modification. In some embodiments, backbone modification results in a longer half-life for the RNA due to reduced degradation (e.g., nuclease-mediated degradation). This in turn results in a longer half-life. Examples of suitable backbone modifications include, but are not limited to, phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, and locked nucleic acid (LNA) backbone modifications. These modifications may be used in combination with each other and/or in combination with phosphodiester backbone linkages.

Alternatively or additionally, RNAi molecules targeting PSMB5 may comprise other modifications, including modifications at the base or sugar moiety. Examples include RNA having sugars that are covalently attached to low molecular weight organic groups other than a hydroxyl group at the 3' position and other than a phosphate group at the 5' position (e.g., a 2'-O-alkylated ribose), or RNA having sugars such as arabinose instead of ribose. RNA also embraces substituted purines and pyrimidines such as C-5 propyne modified bases (Wagner et al., *Nature Biotechnology* 14:840-844, 1996). Other purines and pyrimidines include, but are not limited to, 5-methylcytosine, 2-aminopurine, 2-amino-6-chloropurine, 2,6-diaminopurine, and hypoxanthine. Other such modifications are well known to those of skill in the art.

RNAi molecules that comprise a nucleotide sequence complementary to all or a segment of the target sequence can be designed and prepared using any suitable methods. In some embodiments, an RNAi molecule may be designed with assistance from comprehensive sequence databases, such as those known for *Tribolium* and *Drosophila* genetics (e.g., Flybase, SnapDragon, Beetlebase, etc.). In some embodiments, a sequence database is utilized to determine off-target effects of a designed RNAi molecule (e.g., as in Arziman, Z., Horn, T., & Boutros, M. (2005). E-RNAi: a web application to design optimized RNAi constructs. *Nucleic Acids Research,* 33 (Web Server issue), W582-W588. doi:10.1093/nar/gki468.)

Methods of Use

Aspects of the present disclosure, in some embodiments, provide methods for controlling an insect infestation comprising delivering to a plant or insect (e.g., a Coleopteran insect, e.g., a Colorado potato beetle) an effective amount of an RNAi molecule targeting PSMB5 (or a composition comprising an RNAi molecule targeting PSMB5). In some embodiments, the method of delivery comprises applying to a surface of a plant or insect, a composition comprising the RNAi molecule. In some embodiments, a composition comprising an RNAi molecule targeting PSMB5 is a solid or liquid (e.g., solution, suspension, or emulsions). Non limiting examples include emulsifiable concentrates, concentrate solutions, low concentrate solutions, ultra-low volume concentrate solutions, water-soluble concentrate solutions, water-soluble liquid solutions, baits (paste, gel, liquid, solid or injectable), smoke, fog, invert emulsions, flowables, aerosols, homogenous and non-homogenous mixtures, suspensions (water and oil-based), dust, powders (wettable or soluble), granules (water-dispersible or dry flowables), pellets, capsules, fumigants, encapsulated or micro-encapsulation formulations, or any combinations thereof.

In some embodiments, a composition comprising an RNAi molecule targeting PSMB5 may be applied as a concentrate, spray (after dilution or concentrate), fog, in furrow, seed treatment, seed coating, drench, drip, insect diet, bait, or any other forms suited for applying to a furrow. The RNAi molecule targeting PSMB5 described herein may be delivered to any portion of a plant, including, but are not limited to, leaf, stem, flower, fruit, shoot, root, seed, tuber, anther, stamen, and/or pollen. In some embodiments, RNAi is delivered mechanically, through high pressure spray or sandblasting. In some embodiments, a composition comprises an RNAi molecules and at least one additive selected from adjuvants, attractants, sterilizing agents, growth-regulating substances, carriers or diluents, stabilizers, and/or pesticidal agent(s) (e.g., insecticides, fungicides, and/or herbicides). Pesticidal agents include, for example, other dsRNA targeting genes distinct from PSMB5, insecticidal proteins (patatins, plant lectins, phytoecdysteroids, cry proteins, vegetative insecticidal proteins (vip), cytolytic proteins (cyt)), biotin-binding proteins, protease inhibitors, chitinases, organic compounds, or any combination thereof. Non-pesticidal agents may also be used (e.g. adjuvants, such as antifoaming agents, buffers, compatibility agents, drift control additives, emulsifiers, extenders, invert emulsifiers, plant penetrants, safeners, spreaders, stickers, surfactants, thickeners, and wetting agents).

A composition, in some embodiments, include a mixture of an RNAi molecule targeting PSMB5 and at least one of a variety of agricultural chemicals, insecticides, miticides, fungicides, pesticidal agents and/or biopesticidal (e.g., microbial, plant-incorporated-protectant (PIP), and/or biochemical) agents, such as Spiromesifen, Spirodiclofen, Spirotetramat, Pyridaben, Tebufenpyrad, Tolfenpyrad, Fenpyroximate, Flufenerim, Pyrimidifen, Fenazaquin, Rotenone, Cyenopyrafen, Hydramethylnon, Acequinocyl, Fluacrypyrim, Aluminium phosphide, Calcium phosphide, Phosphine, Zinc phosphide, Cyanide, Diafenthiuron, Azocyclotin, Cyhexatin, Fenbutatin oxide, Propargite, Tetradifon, Bensultap, Thiocyclam, Thiosultap-sodium, Flonicamid, Etoxazole, Clofentezine, Diflovidazin, Hexythiazox, Chlorfluazuron, Bistrifluron, Diflubenzuron, Flucycloxuron, Flufenoxuron, Hexaflumuron, Lufenuron, Novaluron, Noviflumuron, Teflubenzuron, Triflumuron, Buprofezin, Cyromazine, Hydroprene, Kinoprene, Methoprene, Fenoxycarb, Pyriproxyfen, Pymetrozine, Pyrifluquinazon, Chlorfenapyr, Tralopyril, methyl bromide and/or other alkyl halides, Chloropicrin, Sulfuryl fluoride, Benclothiaz, Chinomethionat, Cryolite, Methylneodecanamide, Benzoximate, Cymiazole, Fluensulfone, Azadirachtin, Bifenazate, Amidoflumet, Dicofol, Plifenate, Cyflumetofen, Pyridalyl, Beauveria bassiana GHA, Sulfoxaflor, Spinetoram, Spinosad, Spinosad, Emamectin benzoate, Lepimectin, Milbemectin, Abamectin, Methoxyfenozide, Chromafenozide, Halofenozide, Tebufenozide, Amitraz, Chlorantraniliprole, Cyantraniliprole, Flubendiamide, alpha-endosulfan, Chlordane, Endosulfan, Fipronil, Acetoprole, Ethiprole, Pyrafluprole, Pyriprole, Indoxacarb, Metaflumizone, Acrinathrin, Allethrin, Allethrin-cis-trans, Allethrin-trans, beta-Cyfluthrin, beta-Cypermethrin, Bifenthrin, Bioallethrin, Bioallethrin S-cyclopentenyl, Bioresmethrin, Cycloprothrin, Cyfluthrin, Cyhalothrin, Cypermethrin, Cyphenothrin [(1R)-trans-isomers], Dimefluthrin, Empenthrin [(EZ)-(1R)-isomers], Esfenvalerate, Etofenprox, Fenpropathrin, Fenvalerate, Flucythrinate, Flumethrin, Gamma-cyhalothrin, lambda-Cyhalothrin, Meperfluthrin, Metofluthrin, Permethrin, Phenothrin [(1R)-trans-isomer], Prallethrin, Profluthrin, Protrifenbute, Resmethrin, Silafluofen, tau-Fluvalinate, Tefluthrin, Tetramethrin, Tetramethrin [(1R)-isomers], Tetramethylfluthrin, theta-Cypermethrin, Tralomethrin, Transfluthrin, zeta-Cypermethrin, alpha-Cypermethrin, Deltamethrin, DDT, Methoxychlor, Thiodicarb, Alanycarb, Aldicarb, Bendiocarb, Benfuracarb, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiofanox, Triazamate, Trimethacarb, XMC, Xylylcarb, Chlorpyrifos, Malathion, Acephate, Azamethiphos, Azinphos-ethyl, Azinphos-methyl, Cadusafos, Chlorethoxyfos, Chlorfenvinphos, Chlormephos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fonofos, Fosthiazate, Imicyafos, Isofenphos-methyl, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-ethyl, Profenofos, Propaphos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, Vamidothion Imidacloprid, Thiamethoxam, Acetamiprid, Clothianidin, Dinotefuran, Nitenpyram, Nithiozine, Nicotine, Thiacloprid, cyantraniliprole, carbamates, organophosphates, cyclodiene organochlorines, phenylpyrazoles (fiproles), pyrethroids, pyrethins, DDT Methoxychlor, Neonicotinoids, Nicotine, Sulfoximines, Butenolides, Mesoionics, Spinosyns, Avermectins, Milbernycins, Juvenile hormone analogues, Fenoxycarb, Pyriproxyfen, Alkyl halides, Chloropicrin, Fluorides, Borates, Tarter emetic, Methyl isothiocyanate generators, Pyridine azomethine derivatives, Pyropenes, Clofentezine, Diflovidazin, Hexythiazox, Etoxazole, Diafenthiuron, Organotin miticides, Propargite, Tetradifon, Pyrroles, Dinitrophenols, Sulfuramid, Nereistoxin analogues, Benzoylureas, Buprofezin, Cyromazine, Diacylhydrazines, Amitraz, Hydramethylnon, Acequinocyl, Fluacrypyrim, Bifenazate, METI acaricides and insecticides, Rotenone, Oxadiazines, Semicarbazones, Tetronic and Tetramic acid derivatives, Phosphides, Cyanides, Beta-ketonitrile derivatives, Carboxanilides, Diamides, Flonicamid, Meta-diamides Isoxazolines, Granuloviruses (GVs), Nucleopolyhedroviruses (NPVs), GS-omega/kappa HXTX-Hvla peptide, Azadirachtin, Benzoximate, Bromopropylate, Chinomethionat, Dicofol, Lime sulfur, Mancozeb, Pyridalyl, Sulfur, Benzimidazoles, Dicarboximides, Pyridines, Pyrimidines, Triazoles, Acylalanines, Pyridine carboxamides, Anilino-pyrimidines, Quinone outside Inhibitors (Qol-fungicides), Phenylpyrroles, Quinolines, Hydroxyanilides, Toluamides, Cyanoacetamide-oximes, Dinitrophenyl crotonates, Phosphonates, Carboxylic Acid Amides (CAA-fungicides), M1 inorganic, M2 inorganic, M3 dithiocarbamates, M4 phthalimides, paraffinic oil, petroleum-based horticultural oils, palmitic oil, steric oil, linoleic oil, oleic oils, canola oil, soybean oil, oregano oil, tagetes oil, balsam fir oil, thyme oil, black pepper oil, mint oil, cedarwood oil, fish oil, jojoba oil, lavadin oil, castor oil, eucalyptus oil, ocimum oil, patchouli oil, citrus oil, artemisia oil, camphor oil, wintergreen oil, methyl eugenol oil, thymol oil, geranium oil, sesame oil, linseed oil, cottonseed oil, lemongrass oil, bergamot oil, mustard oil, orange oil, citronella oil, tea tree oil, neem oil, garlic oil, *Bacillus sphaericus, Bacillus thuringiensis* (e.g., *Bacillus thuringiensis* var. *aizawai, Bacillus thuringiensis* var. *israelensis, Bacillus thuringiensis* var. *kurstaki, Bacillus thuringiensis* var. *sphaericus, Bacillus thuringiensis* var. *tenebrionensis*) and the insecticidal proteins they produce (e.g., Cry1Ab, Cry1Ac, Cry1Fa, Cry1A.105, Cry2Ab, Vip3A, mCry3A, Cry3Ab, Cry3Bb, Cry34Ab1/Cr35Ab1, and as further exemplified in Crickmore, N., Baum, J., Bravo, A., Lereclus, D., Narva, K., Sampson, K., Schnepf, E., Sun, M. and Zeigler, D. R. "*Bacillus thuringiensis* toxin nomenclature" (2018)). *Paenibacillus popilliae, Serratia entomophila*, nuclear polyhedrosis viruses, granulosis viruses, non-occluded baculoviruses, *Beauveria* spp, *Metarhizium, Entomophaga, Zoopthora, Paecilomyces fumosoroseus, Normuraea, Lecanicillium lecanii, Nosema, Thelohania, Vairimorpha*, Steinernema spp, *Heterorhabditis* spp or any combination thereof, which may further comprise an active ingredient selected from the group consisting of azinphos-methyl, acephate, isoxathion, isofenphos, ethion, etrimfos, oxydemeton-methyl, oxydeprofos, quinalphos, chlorpyrifos, chlorpyrifos-methyl, chlorfenvin phos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafen thion, pirimiphos-methyl, fenitrothion, fenthion, phenthoate, flupyrazophos, prothiofos, propaphos, profenofos, phoxime, phosalone, phosmet, formothion, phorate, malathion, mecarbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofen carb, carbaryl, carbosulfan, xylylcarb, thiodicarb, pirimicarb, fenobucarb, furathiocarb, propoxur, ben diocarb, benfuracarb, methomyl, metolcarb, XMC, carbofuran, aldoxycarb, oxamyl, acrin athrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cyper-methrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, ben sultap, acetamiprid, imidacloprid, clothianidin, dinotefuran, thiacloprid, thiamethoxam, nitenpyram, chlorfluazuron, difluben zuron, teflubenzuron, triflumuron, novaluron, noviflumuron, bistrifluoron, fluazuron, flucy-cloxuron, flufenoxuron, hexaflumuron, lufenuron, chromafen ozide, tebufenozide, halofen ozide, methoxyfen ozide, diofen olan, cyromazine, pyriproxyfen, buprofezin, methop-rene, hydroprene, kinoprene, triazamate, endosulfan, chlorfenson, chlorobenzilate, dicofol, bromopropylate, acetoprole, flpronil, ethiprole, pyrethrin, rotenone, nicotinesulphate, spinosad, finpronil, spirotetramat abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, flu-azinam, flufenzin, hexythiazox, propargite, polynactin complex, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, triadimefon, hexaconazole, propiconazole, ipconazole, prochloraz, triflumizole, tebuconazole, epoxiconazole, difenoconazole, flu silazole, triadimenol, cyproconazole, metconazole, fluquinconazole, bitertanol, tetraconazole, triti-conazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuari-mol, bupirimate, mepanipyrim, cyprodinil, pyrimethanil, metalaxyl, mefenoxam, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoxim-methyl, metominostrobin, orysastrobin, fluoxastrobin, trifloxystrobin, dimoxystrobin, pyraclostrobin, picoxystrobin, iprodione, procymidone, vinclozolin, chlozolinate, flusulfamide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolar-S-methyl, tia-dinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanide, triforine, isoprothiolane, ferimzone, diclomezine, tecloftalam, pencycuron, chinomethionat, iminoctadine acetate, iminoctadine albesilate, ambam, polycarbamate, thiadiazine, chloroneb, nickel dimethyldithiocarbamate, guazatine, dodecylguanidine acetate, quintozene, tolylfluanid, anilazine, nitrothalisopropyl, fenitropan, dimethirimol, benthiazole, flumetover, mandipropamide, and penthiopyrad, or any combinations thereof.

In some embodiments, an RNAi molecule targeting PSMB5 is supplied in the diet of a Coleopteran insect. For example, an RNAi molecule targeting PSMB5 may be applied topically to a plant, or seeds (e.g. via soaking, coating, dusting or spraying), or cells of a plant may be engineered to express the RNAi molecule. RNAi molecules may also be supplied in another food or water source.

The plant may be any plant that is subject to infestation by a Coleopteran insect. In some embodiments, the plant is a Solanaceous plant (e.g., family Solanaceae). Examples of Solanaceous plants include, but are not limited to, potato plants (Solanum tuberosum), buffalo bur plants (Solanum rostratum), eggplant plants (Solanum melongena), tomato plants (Solanum lycopersicum), tobacco plants (Nicotiana tabacum), pepper plants (Capsicum annum) and woody nightshade plants (Solanum dulcamara).

Thus, in some embodiments, the methods comprise delivering to a plant (e.g., a potato plant) with an RNAi molecule targeting PSMB5, for example, in an effective amount to suppress infestation of the plant by a Coleopteran insect (e.g., Colorado potato beetle). In other embodiments, the methods comprise delivering to a buffalo bur plant with an RNAi molecule targeting PSMB5, for example, in an effective amount to suppress infestation of the plant by a Coleopteran insect (e.g., Colorado potato beetle). In yet other embodiments, the methods comprise delivering to an eggplant plant with an RNAi molecule targeting PSMB5, for example, in an effective amount to suppress infestation of the plant by a Coleopteran insect (e.g., Colorado potato beetle). In still other embodiments, the methods comprise delivering to a tomato plant with an RNAi molecule targeting PSMB5, for example, in an effective amount to suppress infestation of the plant by a Coleopteran insect (e.g., Colorado potato beetle). In further embodiments, the methods comprise delivering to a tobacco plant with an RNAi molecule targeting PSMB5, for example, in an effective amount to suppress infestation of the plant by a Coleopteran insect (e.g., Colorado potato beetle). In additional embodiments, the methods comprise delivering to a pepper plant with an RNAi molecule targeting PSMB5, for example, in an effective amount to suppress infestation of the plant by a Coleopteran insect (e.g., Colorado potato beetle).

Delivering to a plant (e.g., a part of a plant) and/or Coleopteran insect an RNAi molecule targeting PSMB5 may include, for example, applying (e.g., soaking, coating, or dusting) the RNAi molecule or a composition comprising the RNAi molecule topically to any portion of a plant (e.g., roots, tubers, stem, branches, leaves, flower, etc), ground (e.g., soil, dirt, grass, etc.), insect and/or diet of the insect. A delivering step may also include genetically engineering cells of a plant to express the RNAi molecule. A delivering step may also include exposing a plant or Coleopteran insect to an organism (e.g., virus, bacteria, fungus, etc.) that has been genetically engineered to express and/or deliver the RNAi molecule to the plant or Coleopteran insect.

An effective amount is the amount of an RNAi molecule targeting PSMB5 required to confer a beneficial effect on infestation (e.g. death, cessation of feeding, inhibition of growth, development or reproduction) by a Coleopteran insect, either alone or in combination with one or more other additives. Beneficial effects include a reduction in infestation, for example, by at least 10%, at least 20%, at least 30%, at least 40%, at least 50%, at least 60%, at least 70%, at least 80%, or at least 90%, relative to a control. In some embodiments, the control is the absence of an insecticide and/or pesticide. In some embodiments, an effective amount of an RNAi molecule targeting PSMB5 completely eliminates Coleopteran insect (e.g., Colorado potato beetle) infestation of a plant.

Effective amounts vary, as recognized by those skilled in the art, depending on the particular plant, the severity of the infestation, the duration of the infestation, previous exposure to insecticides and like factors within the knowledge and expertise of a practitioner. These factors are well known to those of ordinary skill in that art and can be addressed with no more than routine experimentation. It is generally preferred that lower effective concentrations be used, that is, the lowest concentration that provides control of an insect, to increase efficiency and decrease cost.

An effective amount of an RNAi molecule targeting PSMB5 may also vary depending on the method of delivery.

In some embodiments, an effective amount of an RNAi molecule targeting PSMB5 is expressed as micrograms (μg) of RNAi molecule targeting PSMB5 per centimeter squared ($cm^2$) of a surface of a plant or ground (e.g., soil, dirt, grass, etc.), i.e., $\mu g/cm^2$. Thus, in some embodiments, an effective amount of an RNAi molecule targeting PSMB5 comprises 0.001 μg/cm$^2$ to 10 μg/cm$^2$. In some embodiments, an effective amount of an RNAi molecule targeting PSMB5 comprises 0.001 μg/cm$^2$ to 9 μg/cm$^2$, 0.001 μg/cm$^2$ to 8 μg/cm$^2$, 0.001 μg/cm$^2$ to 7 μg/cm$^2$, 0.001 μg/cm$^2$ to 6 μg/cm$^2$, 0.001 μg/cm$^2$ to 5 μg/cm$^2$, 0.001 μg/cm$^2$ to 4 μg/cm$^2$, 0.001 μg/cm$^2$ to 3 μg/cm$^2$, 0.001 μg/cm$^2$ to 2 μg/cm$^2$, 0.001 μg/cm$^2$ to 1 μg/cm$^2$, 0.001 μg/cm$^2$ to 0.1 μg/cm$^2$, or 0.001 μg/cm$^2$ to 0.01 μg/cm$^2$. In some embodiments, an effective amount of an RNAi molecule targeting PSMB5 comprises 0.01 μg/cm$^2$ to 10 μg/cm$^2$, 0.1 μg/cm$^2$ to 10 μg/cm$^2$, 1 μg/cm$^2$ to 10 μg/cm$^2$, 2 μg/cm$^2$ to 10 μg/cm$^2$, 3 μg/cm$^2$ to 10 μg/cm$^2$, 4 μg/cm$^2$ to 10 μg/cm$^2$, 5 μg/cm$^2$ to 10 μg/cm$^2$, 6 μg/cm$^2$ to 10 μg/cm$^2$, 7 μg/cm$^2$ to 10 μg/cm$^2$, 8 μg/cm$^2$ to 10 μg/cm$^2$, or 9 μg/cm$^2$ to 10 μg/cm$^2$.

In some embodiments, an effective amount of an RNAi molecule targeting PSMB5 is expressed as grams (g) of RNAi molecule targeting PSMB5 per acre (ac.) of a surface of a plant or ground (e.g., soil, dirt, grass, etc.), i.e., g/ac. Thus, in some embodiments, an effective amount of an RNAi molecule targeting PSMB5 comprises 0.01 g/ac. to 100 g/ac. In some embodiments, an effective amount of an RNAi molecule targeting PSMB5 comprises 0.01 g/ac. to 90 g/ac., 0.01 g/ac. to 80 g/ac., 0.01 g/ac. to 70 g/ac., 0.01 g/ac. to 60 g/ac., 0.01 g/ac. to 50 g/ac., 0.01 g/ac. to 40 g/ac., 0.01 g/ac. to 30 g/ac., 0.01 g/ac. to 20 g/ac., 0.01 g/ac. to 10 g/ac., 0.01 g/ac. to 1 g/ac., or 0.01 g/ac. to 0.1 g/ac. In some embodiments, an effective amount of an RNAi molecule targeting PSMB5 comprises 0.1 g/ac. to 100 g/ac., 1 g/ac. to 100 g/ac., 10 g/ac. to 100 g/ac., 20 g/ac. to 100 g/ac., 30 g/ac. to 100 g/ac., 40 g/ac. to 100 g/ac., 50 g/ac. to 100 g/ac., 60 g/ac. to 100 g/ac., 70 g/ac. to 100 g/ac., 80 g/ac. to 100 g/ac., or 90 g/ac. to 100 g/ac.

In some embodiments, the effectiveness of an RNAi molecule to control Coleopteran insects can be determined using the ability of the RNAi molecule to kill or cause death of an insect or population of insects. The rate of death in a population of insects may be determined by percent mortality (e.g., percent mortality over time). Generally, percent mortality of a population of insects reflects the percentage of insects in said population that have died as a result of the RNAi molecule (e.g., 75% mortality indicates that an RNAi molecule has killed 75% of the total insect population). In some embodiments, percent mortality is measured over time (e.g., over the course of a multi-day exposure of insects to an RNAi molecule). In some embodiments, percent mortality is measured after at least 3, 4, 5, 6, 7, 8, 9, 10, 15, or 20 days of exposure. In some embodiments, an RNAi molecule causes a percent mortality of at least 30%, 40%, 50%, 60%, 70%, 80%, 90%, 95%, 98%, or 100% of a Coleopteran insect population. In some embodiments, at least 30%, 40%, 50%, 60%, 70%, 80%, 90%, 95%, 98%, or 100% of a Coleopteran insect population are killed by an RNAi molecule that targets PSMB5. In some embodiments, percent mortality of an RNAi molecule is compared to a control (e.g., a control molecule or untreated conditions). In some embodiments, percent mortality of an RNAi molecule is at least 30%, 40%, 50%, 60%, 70%, 80%, 90%, 100%, 120%, 150%, or 200% higher than a control (e.g., a control molecule or untreated conditions).

In some embodiments, the effectiveness of an RNAi molecule to control Coleopteran insects can be determined using the ability of the RNAi molecule to limit the leaf disc consumption of a Coleopteran insect or an insect population. Leaf disc consumption refers to the amount (e.g., percentage) of plant material (e.g., an eggplant leaf) that is consumed or eaten by an insect or population of insects. In some embodiments, an RNAi molecule causes at least a 10%, 20%, 30%, 40%, 50%, 60%, 70%, 80%, 90%, 95%, 98%, or 100% decrease in the leaf disc consumption by an insect or population of insects. In some embodiments, the ability of an RNAi molecule to decrease leaf disc consumption is compared relative to a control (e.g., a control molecule or untreated conditions). In some embodiments, leaf disc consumption is measured over time (e.g., over the course of a multi-day exposure of insects to an RNAi molecule). In some embodiments, leaf disc consumption is measured after 3, 4, 5, 6, 7, 8, 9, 10, or more days of exposure.

In some embodiments, the effectiveness of an RNAi molecule to control Coleopteran insects can be determined using the ability of the RNAi molecule to decrease percent plant defoliation by a Coleopteran insect or an insect population. Percent plant defoliation refers to the percentage of plant material (e.g., an eggplant leaf) that is destroyed (e.g., consumed) by an insect or population of insects. In some embodiments, an RNAi molecule causes at least a 10%, 20%, 30%, 40%, 50%, 60%, 70%, 80%, 90%, 95%, 98%, or 100% decrease in the percent plant defoliation by an insect or population of insects. In some embodiments, an RNAi molecule causes percent plant defoliation to decrease below 40%, 30, 25%, 20%, 15%, 10%, 5%, 3%, or 1%. In some embodiments, percent plant defoliation remains below 40%, 30, 25%, 20%, 15%, 10%, 5%, 3%, or 1% for at least 5, 6, 7, 8, 9, 10, 15, or 20 days following exposure of insects to an RNAi molecule. In some embodiments, the ability of an RNAi molecule to decrease percent plant defoliation is compared relative to a control (e.g., a control molecule or untreated conditions). In some embodiments, percent plant defoliation is measured over time (e.g., over the course of a multi-day exposure of insects to an RNAi molecule). In some embodiments, percent plant defoliation is measured after 3, 4, 5, 6, 7, 8, 9, 10, or more days of exposure.

In some embodiments, an RNAi molecule targeting PSMB5 may be formulated in a solution (e.g., that is applied to a surface of the Coleopteran insect and/or diet (e.g., food and/or water ingested), a plant or ground (e.g., soil, dirt, grass, etc.)). In some embodiments, the effective amount of the RNAi molecule targeting PSMB5 in the solution is expressed as nanograms (ng) or micrograms (μg) of RNAi molecule targeting PSMB5 per milliliter (ml) of the solution, i.e., ng/ml. Thus, in some embodiments, a solution comprises an RNAi molecule targeting PSMB5 at a concentration of 10 ng/ml to 100 μg/ml. In some embodiments, a solution comprises an RNAi molecule targeting PSMB5 at a concentration of 10 ng/ml to 100 μg/ml, 100 ng/ml to 100 μg/ml, 250 ng/ml to 100 μg/ml, 750 ng/ml to 100 μg/ml, 1000 ng/ml to 100 μg/ml, 10 μg/ml to 100 μg/ml, 25 μg/ml to 100 μg/ml, 50 μg/ml to 100 μg/ml, or 75 μg/ml to 100 μg/ml. In some embodiments, a solution comprises an RNAi molecule targeting PSMB5 at a concentration of 10 ng/ml to 100 μg/ml, 10 ng/ml to 75 μg/ml, 10 ng/ml to 50 μg/ml, 10 ng/ml to 25 μg/ml, 10 ng/ml to 10 μg/ml, 10 ng/ml to 1000 ng/ml, 10 ng/ml to 1000 ng/ml, 10 ng/ml to 750 ng/ml, 10 ng/ml to 500 ng/ml, 10 ng/ml to 250 ng/ml, 10 ng/ml to 100 ng/ml, 10 ng/ml to 75 ng/ml, 10 ng/ml to 50 ng/ml, or 10 ng/ml to 25 ng/ml.

A solution, in some embodiments, comprises an RNAi molecule targeting PSMB5 and at least one additional additive (e.g., a pesticide, surfactant or other non-pesticidal agent). In some embodiments, such a mixture comprises an RNAi molecule targeting PSMB5 at a concentration of 0.0001 μg/ml to 10 μg/ml (e.g., that is applied to a surface of a plant and/or ground (e.g., soil, dirt, grass, etc.)). In some embodiments, such a mixture comprises an RNAi molecule targeting PSMB5 at a concentration of 0.001 μg/ml to 10

µg/ml, 0.01 µg/ml to 10 µg/ml, 0.1 µg/ml to 10 µg/ml, 1 µg/ml to 10 µg/ml, 2 µg/ml to 10 µg/ml, 3 µg/ml to 10 µg/ml, 4 µg/ml to 10 µg/ml, 5 µg/ml to 10 µg/ml, 6 µg/ml to 10 µg/ml, 7 µg/ml to 10 µg/ml, 8 µg/ml to 10 µg/ml, or 9 µg/ml to 10 µg/ml. In some embodiments, such a mixture comprises an RNAi molecule targeting PSMB5 at a concentration of 0.0001 µg/ml to 9 µg/ml, 0.0001 µg/ml to 8 µg/ml, 0.0001 µg/ml to 7 µg/ml, 0.0001 µg/ml to 6 µg/ml, 0.0001 µg/ml to 5 µg/ml, 0.0001 µg/ml to 4 µg/ml, 0.0001 µg/ml to 3 µg/ml, 0.0001 µg/ml to 2 µg/ml, 0.0001 µg/ml to 1 µg/ml, 0.0001 µg/ml to 0.1 µg/ml, 0.0001 µg/ml to 0.01 µg/ml, or 0.0001 µg/ml to 0.001 µg/ml.

In some embodiments, an RNAi molecule targeting PSMB5 is provided in a diet of an insect. Thus, in some embodiments, an effective amount of an RNAi molecule targeting PSMB5 is expressed as micrograms (µg) of RNAi molecule targeting PSMB5 per milliliter (ml) of the diet of the insect, i.e., µg/ml. In some embodiments, the diet of an insect comprises an RNAi molecule targeting PSMB5 at a concentration of 0.001 µg/ml to 10 µg/ml. In some embodiments, the diet of an insect comprises an RNAi molecule targeting PSMB5 at a concentration of 0.001 µg/ml to 9 µg/ml, 0.001 µg/ml to 8 µg/ml, 0.001 µg/ml to 7 µg/ml, 0.001 µg/ml to 6 µg/ml, 0.001 µg/ml to 5 µg/ml, 0.001 µg/ml to 4 µg/ml, 0.001 µg/ml to 3 µg/ml, 0.001 µg/ml to 2 µg/ml, 0.001 µg/ml to 1 µg/ml, 0.001 µg/ml to 0.1 µg/ml, or 0.001 µg/ml to 0.01 µg/ml. In some embodiments, the diet of an insect comprises an RNAi molecule targeting PSMB5 at a concentration of 0.01 µg/ml to 10 µg/ml, 0.1 µg/ml to 10 µg/ml, 1 µg/ml to 10 µg/ml, 2 µg/ml to 10 µg/ml, 3 µg/ml to 10 µg/ml, 4 µg/ml to 10 µg/ml, 5 µg/ml to 10 µg/ml, 6 µg/ml to 10 µg/ml, 7 µg/ml to 10 µg/ml, 8 µg/ml to 10 µg/ml, or 9 µg/ml to 10 µg/ml.

The step of delivering to any portion of a plant (e.g., roots, tubers, stem, branches, leaves, flower, etc), ground (e.g., soil, dirt, grass, etc.), insect and/or diet of the insect with an RNAi molecule targeting PSMB5 may include a single application (single contact) or multiple applications (multiple contacts) of the RNAi molecule targeting PSMB5 to the plant, ground (e.g., soil, dirt, grass, etc.), insect and/or diet of the insect. Delivery to a portion of a plant, insect and/or diet of the insect may be in the form of a spray (e.g., pressurized/aerosolized spray, pump) solid, (e.g. powder, pellet, bait), or liquid (e.g., homogeneous mixtures such as solutions and non-homogeneous mixtures such as suspensions (water and oil based), colloids, micelles, and emulsions). The period of time of contact may vary. In some embodiments, delivering comprises an exposure of an RNAi molecule targeting PSMB5 with a portion of a plant and/or Coleopteran insect for a suitable period sufficient for reduction of growth, reproduction (e.g., fertility and/or fecundity), and/or feeding of the Coleopteran insect and/or death of the Coleopteran insect, if any.

In some embodiments, delivery of an RNAi molecule targeting PSMB5 with a plant and/or Coleopteran insect is followed by ingestion and/or absorption of the RNAi molecule targeting PSMB5 by the plant and/or Coleopteran insect. In some embodiments, ingestion of the RNAi molecule targeting PSMB5 by the Coleopteran insect alters a biological function of the Coleopteran insect, thereby controlling infestation by the Coleopteran insect. Examples of altered biological function of the Coleopteran insect include, but are not limited to, reduced growth, reduced reproduction (e.g., fertility and/or fecundity), reduced feeding, decreased movement, decreased development, decreased cellular repair, and/or increased mortality.

In some embodiments, delivering comprises applying an RNAi molecule targeting PSMB5 to a portion of the surface of a plant, a surface contacted by a Coleopteran insect (e.g., ground (e.g., soil, dirt, grass, etc.)), and/or the Coleopeteran insect. In some embodiments, applying an RNAi molecule targeting PSMB5 to a portion of a surface comprises spraying, coating, and/or dusting the surface or portion thereof. In some embodiments, applying an RNAi molecule targeting PSMB5 RNA to a portion of a surface comprises ground drenching or applying the RNAi molecule as a granulated or powdered formulation to the soil adjacent to the roots of the plant.

In some embodiments delivering comprises contacting a seed with an RNAi molecule targeting PSMB5. In some embodiments, contacting a seed with an RNAi molecule targeting PSMB5 can be accomplished using any method known in the art which allows a suppressive amount of dsRNA to enter the seed. These examples include, but are not limited to, soaking, spraying or coating the seed with powder, emulsion, suspension, or solution. In some embodiments, a seed coating or a seed treatment composition comprises an RNAi molecule targeting PSMB5 and at least one plant-enhancing agent, including but not limited to active substances intended to positively influence seed germination, plant emergence, plant growth, plant defense, plant development, and/or plant yield.

A RNAi molecule targeting PSMB5 may be applied to any portion of a plant (e.g., roots, tubers, stem, branches, leaves, flower, etc). In some embodiments, the RNAi molecule targeting PSMB5 is contacted with an above-ground portion of a plant (e.g., a leaf) and/or with a below-ground portion of a plant (e.g., a root), which may include at least one in furrow formulation selected from the group consisting of a powder, granule, pellet, capsule, soluble liquid concentrate, spray (after dilution or concentrate), fog, in furrow, seed treatment, seed coating, insect diet, bait, drench, drip irrigation, or any other forms suited for applying to a furrow. Portions of a plant that may be contacted with the RNAi molecule targeting PSMB5 described herein include, but are not limited to, leaf, stem, flower, fruit, shoot, root, seed, tuber, anther, stamen, or pollen. In some embodiments, RNAi is delivered mechanically, through high pressure spray or sandblasting.

In some embodiments, delivering comprises providing an RNAi molecule targeting PSMB5 for dietary uptake by the Coleopteran insect. In some embodiments, contacting comprises providing an RNAi molecule targeting PSMB5 that can be ingested or otherwise absorbed internally by the Coleopteran insect. In some embodiments, the RNAi molecule targeting PSMB5 is provided in a diet for dietary uptake by the Coleopteran insect. In some embodiments, the RNAi molecule targeting PSMB5 is provided in/on a plant or plant part, or topically applied to a plant or plant part (e.g., soaking, coating, dusting). In some embodiments, the RNAi molecule targeting PSMB5 is expressed in a plant or plant part.

In some embodiments, delivering an RNAi molecule targeting PSMB5 to a Coleopteran insect inhibits expression of (reduces or inhibits expression of) an endogenous complementary nucleotide sequence (e.g., RNA sequence) in the Coleopteran insect. In some embodiments, the endogenous complementary nucleotide sequence is an endogenous PSMB5 sequence.

Consequences of inhibition can be confirmed by any appropriate assay to evaluate one or more properties of an insect, or by biochemical techniques that evaluate molecules indicative of PSMB5 expression (e.g., RNA, protein). In some embodiments, the extent to which an RNAi molecule targeting PSMB5 provided herein reduces levels of expression of PSMB5 is evaluated by comparing expression levels (e.g., mRNA or protein levels of PSMB5 to an appropriate control (e.g., a level of PSMB5 expression in a cell or population of cells to which an RNAi molecule targeting PSMB5 has not been delivered or to which a negative control has been delivered). In some embodiments, an appropriate control level of PSMB5 expression may be a predetermined level or value, such that a control level need not be measured every time. The predetermined level or value can take a variety of forms. In some embodiments, a predetermined level or value can be single cut-off value, such as a median or mean.

In some embodiments, delivering an RNAi molecule targeting PSMB5 as described herein results in a reduction in the level of PSMB5 expression in a cell of an insect. In some embodiments, the reduction in levels of PSMB5 expression may be a reduction by at least 10%, at least 20%, at least 30%, at least 40%, at least 50%, at least 60%, at least 70%, at least 80%, at least 90%, at least 95%, at least 98%, at least 99%, or 100% relative to a control level. In some embodiments, the control level is a level of PSMB5 expression in a similar insect cell (or average level among a population of cells) not contacted with the RNAi molecule. In some embodiments, the control level is a level of PSMB5 expression in a similar insect cell (or average level among a population of cells) contacted with an RNAi molecule targeting a gene not expressed by the insect cell, e.g., green fluorescent protein (GFP).

In some embodiments, the effect of delivering to a cell or insect an RNAi molecule targeting PSMB5 is assessed after a finite period of time. For example, levels of PSMB5 may be determined in a cell or insect at least 4 hours, 8 hours, 12 hours, 18 hours, 24 hours; or at least one, two, three, four, five, six, seven, or fourteen days after delivering to the cell or insect the RNAi molecule targeting PSMB5.

In some embodiments, delivery of an RNAi molecule targeting PSMB5 as described herein results in a reduction in the level of growth, reproduction (e.g., fertility and/or fecundity), and/or feeding of an insect. In some embodiments, the reduction in levels of growth, reproduction (e.g., fertility and/or fecundity), and/or feeding may be a reduction by at least 10%, at least 20%, at least 30%, at least 40%, at least 50%, at least 60%, at least 70%, at least 80%, at least 90%, at least 95%, at least 98%, at least 99%, or 100% relative to a control level. In some embodiments, the control level is a level of growth, reproduction (e.g., fertility and/or fecundity), and/or feeding of a similar insect not contacted with the RNAi molecule. In some embodiments, the control level is a level of growth, reproduction (e.g., fertility and/or fecundity), and/or feeding of a similar insect contacted with an RNAi molecule targeting a gene not expressed by the insect cell, e.g., green fluorescent protein (GFP).

In some embodiments, delivery of an RNAi molecule targeting PSMB5 as described herein results in an increase in mortality among a population of insects. In some embodiments, the increase in level of mortality may be an increase by at least 10%, at least 20%, at least 30%, at least 40%, at least 50%, at least 60%, at least 70%, at least 80%, at least 90%, at least 95%, at least 98%, at least 99%, or 100% relative to a control. In some embodiments, the control is mortality among a population of insects not contacted with the RNAi molecule. In some embodiments, the control is among a population of insects contacted with an RNAi molecule targeting a gene not expressed by the insect cell, e.g., green fluorescent protein (GFP).

Aspects of the present disclosure provide plants that expresses an RNAi molecule targeting PSMB5 as described herein. In some embodiments, DNA encoding an RNAi molecule targeting PSMB5 provided herein is provided to a plant (seed or cells of a plant) such that the plant expresses the RNAi molecule targeting PSMB5. In some embodiments, DNA encoding an RNAi molecule targeting PSMB5 is expressed in a plant by transgenic expression, e.g., by stably integrating DNA encoding an RNAi molecule targeting PSMB5 into a genome of a plant such that the plant expresses the RNAi molecule targeting PSMB5.

Methods of Producing RNAi Molecules Targeting PSMB5

RNAi molecules targeting PSMB5 as provided herein may be produced by any suitable method known in the art. Examples of methods for producing an RNAi molecule targeting PSMB5 include, but are not limited to, in vitro transcription (IVT), chemical synthesis, expression in an organism (e.g., a plant), or expression in cell culture (e.g., a plant cell culture), and microbial fermentation.

RNAi molecules targeting PSMB5 may be produced, in some embodiments, according to cell-free production methods described in International Application Publication WO 2017/176963 A1, published Oct. 12, 2017, entitled "Cell-Free Production of Ribonucleic Acid"; U.S. Provisional Application U.S. Ser. No. 62/571,071 filed Oct. 11, 2017, entitled "Methods and Compositions for Nucleoside Triphosphate and Ribonucleic Acid Production"; and International Application Publication WO 2019/075167 A1, published Apr. 18, 2019, entitled "Methods and Compositions for Nucleoside Triphosphate and Ribonucleic Acid Production"; each of which is incorporated herein by reference.

Any suitable DNA encoding RNAi molecules targeting PSMB5 described herein may be used in the methods described herein. A DNA may be a single-stranded DNA (ssDNA) or a double-stranded DNA (dsDNA). In some embodiments, a DNA comprises one or more DNA expression cassette(s) that when transcribed produces a single-stranded RNA (ssRNA) molecule (e.g., that remains single-stranded or folds into an RNA hairpin) or complementary ssRNA molecules that anneal to produce the double-stranded RNA (dsRNA) molecule.

In some embodiments, a DNA comprises a promoter (e.g., an inducible promoter) operably linked to a nucleotide sequence encoding RNA that is complementary to a segment of PSMB5, and optionally a terminator. In other embodiments, a DNA comprises a first promoter (e.g., an inducible promoter) operably linked to a nucleotide sequence encoding RNA that is complementary to a segment of PSMB5, and optionally a terminator, and a second promoter (e.g., an inducible promoter) operably linked to a nucleotide sequence encoding a second RNA that is complementary to the first RNA, and optionally a terminator. In yet other embodiments, a DNA comprises a promoter (e.g., an inducible promoter) operably linked to a nucleotide sequence encoding a first region of an RNA, followed by one or more nucleotides of a loop region, followed by a second region of the RNA, and optionally followed by a terminator, wherein the first region of the RNA is complementary to a segment of PSMB5 and the second region is complementary to the first region. In still other embodiments, a DNA comprises a first strand comprising a first promoter (e.g., an inducible promoter) operably linked to a nucleotide sequence encoding a first RNA that is complementary to a segment of PSMB5, and optionally a terminator, and a second strand comprising a second promoter (e.g., an inducible promoter) operably linked to a nucleotide sequence encoding a second RNA that is complementary to the first RNA, and optionally a terminator wherein the first and second promoters are operably linked to the nucleotide sequence encoding a desired PSMB5-targeting RNA and wherein the bidirectional transcription of the nucleotide sequence encoding the desired PSMB5-targeting RNA results in complementary RNA molecules which anneal to form the dsRNA molecule.

A DNA is typically provided on a vector, such as a plasmid, although other template formats may be used (e.g., linear DNA generated by polymerase chain reaction (PCR), chemical synthesis, or other means known in the art). In some embodiments, more than one DNA is used in a reaction mixture. In some embodiments, 2, 3, 4, 5, or more different DNAs are used in a reaction mixture.

A promoter or terminator may be a naturally-occurring sequence or an engineered (e.g., synthetic) sequence. In some embodiments, an engineered sequence is modified to enhance transcriptional activity. In some embodiments, the promoter is a naturally-occurring sequence. In other embodiments, the promoter is an engineered sequence. In some embodiments, the terminator is a naturally-occurring sequence. In other embodiments, the terminator is an engineered sequence.

EXAMPLES

In order that the invention described herein may be more fully understood, the following examples are set forth. The Examples described in this Application are offered to illustrate the methods, compositions, and systems provided herein and are not to be construed in any way as limiting their scope.

The double-stranded RNA (dsRNA) molecules used in the Examples below are as follows, the sequences of which are presented in Table 5.

GS2: one RNA strand consisting of the sequence of SEQ ID NO: 19 bound to another RNA strand consisting of the sequence of SEQ ID NO: 36. GS2 targets mRNA encoded by nucleotides 450-927 of the DNA sequence of SEQ ID NO: 1.

GS4: one RNA strand consisting of the sequence of SEQ ID NO: 20 bound to another RNA strand consisting of the sequence of SEQ ID NO: 37. GS4 targets mRNA encoded by GFP.

GS47: one RNA strand consisting of the sequence of SEQ ID NO: 21 bound to another RNA strand consisting of the sequence of SEQ ID NO: 38. GS47 targets mRNA encoded by nucleotides 1-449 of the DNA sequence of SEQ ID NO: 1.

GS180: one RNA strand consisting of the sequence of SEQ ID NO: 22 bound to another RNA strand consisting of the sequence of SEQ ID NO: 39. GS180 targets mRNA encoded by nucleotides 450-927 of the DNA sequence of SEQ ID NO: 1.

GS181: one RNA strand consisting of the sequence of SEQ ID NO: 23 bound to another RNA strand consisting of the sequence of SEQ ID NO: 40. GS181 targets mRNA encoded by nucleotides 450-1010 of the DNA sequence of SEQ ID NO: 1.

GS182: one RNA strand consisting of the sequence of SEQ ID NO: 24 bound to another RNA strand consisting of the sequence of SEQ ID NO: 41. GS182 has 70% sequence identity to GS2.

GS183: one RNA strand consisting of the sequence of SEQ ID NO: 25 bound to another RNA strand consisting of the sequence of SEQ ID NO: 42. GS183 has 75% sequence identity to GS2.

GS184: one RNA strand consisting of the sequence of SEQ ID NO: 26 bound to another RNA strand consisting of the sequence of SEQ ID NO: 43. GS184 has 80% sequence identity to GS2.

GS185: one RNA strand consisting of the sequence of SEQ ID NO: 27 bound to another RNA strand consisting of the sequence of SEQ ID NO: 44. GS185 has 85% sequence identity to GS2.

GS186: one RNA strand consisting of the sequence of SEQ ID NO: 28 bound to another RNA strand consisting of the sequence of SEQ ID NO: 45. GS186 has 90% sequence identity to GS2.

GS187: one RNA strand consisting of the sequence of SEQ ID NO: 29 bound to another RNA strand consisting of the sequence of SEQ ID NO: 46. GS187 has 95% sequence identity to GS2.

GS188: one RNA strand consisting of the sequence of SEQ ID NO: 30 bound to another RNA strand consisting of the sequence of SEQ ID NO: 47. GS 188 targets mRNA encoded by nucleotides 80-280 of SEQ ID NO: 2.

GS189: one RNA strand consisting of the sequence of SEQ ID NO: 31 bound to another RNA strand consisting of the sequence of SEQ ID NO: 48. GS189 targets mRNA encoded by nucleotides 105-255 of SEQ ID NO: 2.

GS190: one RNA strand consisting of the sequence of SEQ ID NO: 32 bound to another RNA strand consisting of the sequence of SEQ ID NO: 49. GS190 targets mRNA encoded by nucleotides 130-230 of SEQ ID NO: 2.

GS191: one RNA strand consisting of the sequence of SEQ ID NO: 33 bound to another RNA strand consisting of the sequence of SEQ ID NO: 50. GS191 targets mRNA encoded by nucleotides 155-205 of SEQ ID NO: 2.

GS192: one RNA strand consisting of the sequence of SEQ ID NO: 34 bound to another RNA strand consisting of the sequence of SEQ ID NO: 51. GS180 targets mRNA encoded by nucleotides 167-192 of SEQ ID NO: 2.

Example 1

A PSMB5 RNAi Composition (GS2) Kills Colorado Potato Beetles

Figure 1B:
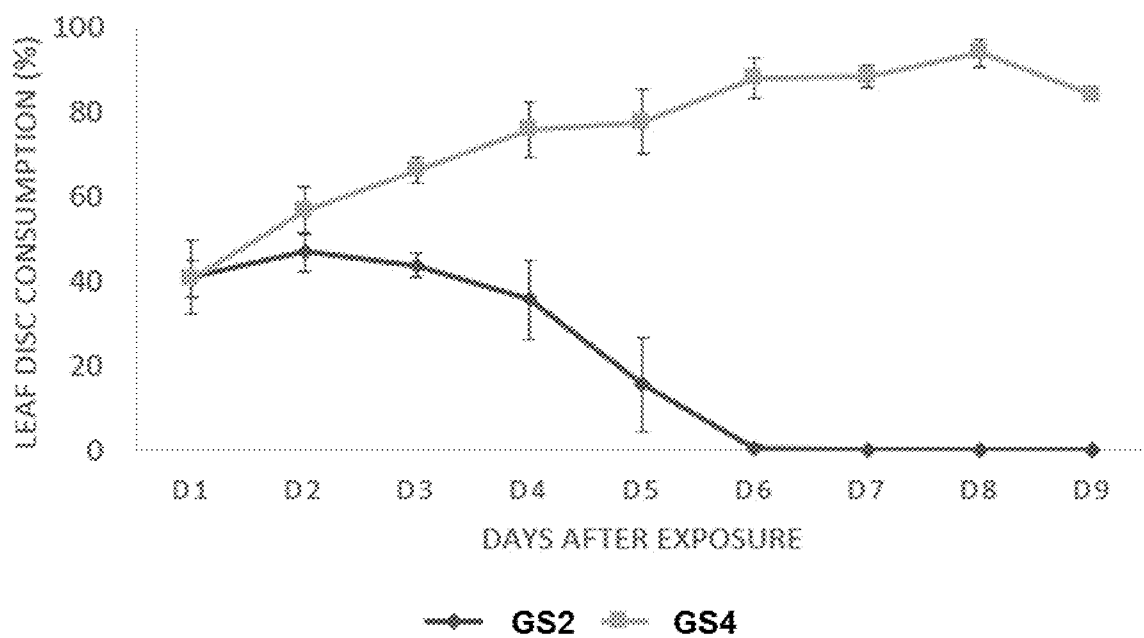

To evaluate the effect of the PSMB5 RNAi polynucleotides (SEQ ID NOS: 19 and 36) on Colorado potato beetles (CPBs), a composition (e.g., comprising water) comprising the PSMB5 RNAi polynucleotide (hereafter, "G52") was applied (at a concentration of 10 $m/cm^2$) onto the leaves of potato plants and allowed to dry. Up to 90% of CPBs died following a 9-day exposure to the GS2-covered potato plant leaves compared with less than 10% of CPBs that die following exposure to the GS4 control (GS4) leaves (FIG. 1A). This increased mortality in response to exposure to GS2 also results in a decrease of potato leaf consumption below 10% compared to CPBs exposed to the GS4 control (FIG. 1B). Percent potato leaf consumption refers to the percentage of potato leaf discs (punched out of potato leaves) following treatment of the discs with the RNAi composition and subsequent exposure of the discs to Colorado potato beetle, for example.

Figure 2A:
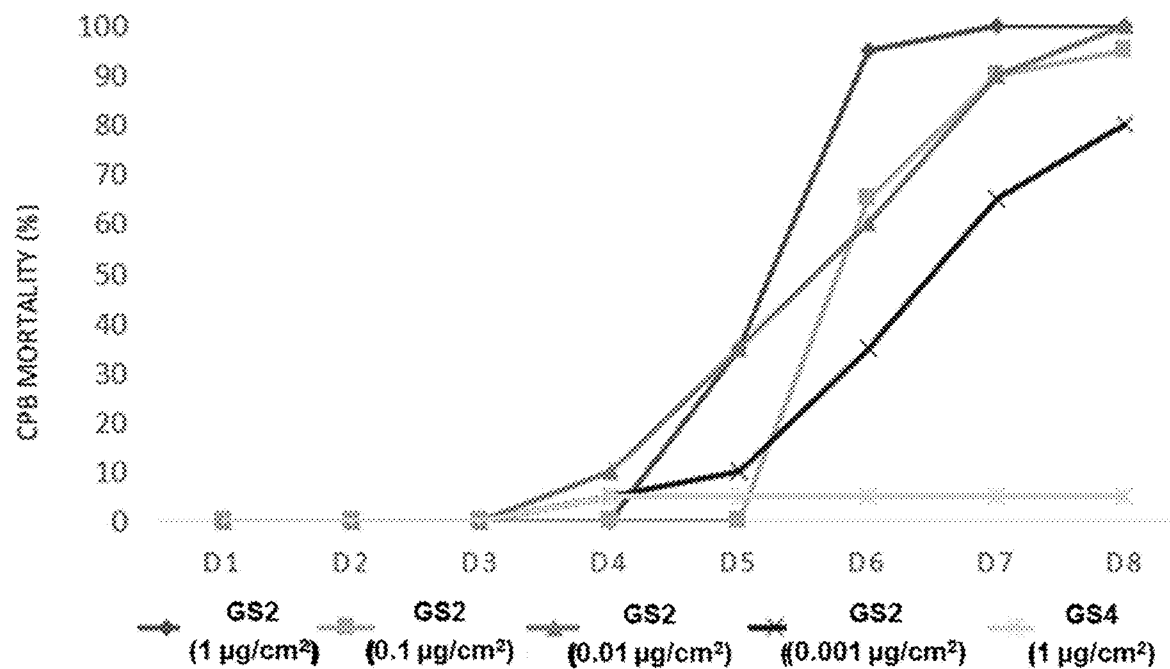
FIGS. 2A-2B include graphs showing the percent mortality of Colorado potato beetles (CPBs) (FIG. 2A) and percent leaf disc consumption by CPBs (FIG. 2B) following a three-day dose-trial time course in CPBs exposed to either a PSMB5 RNAi composition of the present disclosure (GS2 at 1.0 μg/cm$^2$, 0.1 μg/cm$^2$, 0.01 μg/cm$^2$, or 0.001 μg/cm$^2$) or a control RNAi composition (GS4 at 1.0 μg/cm$^2$).
Figure 2B:
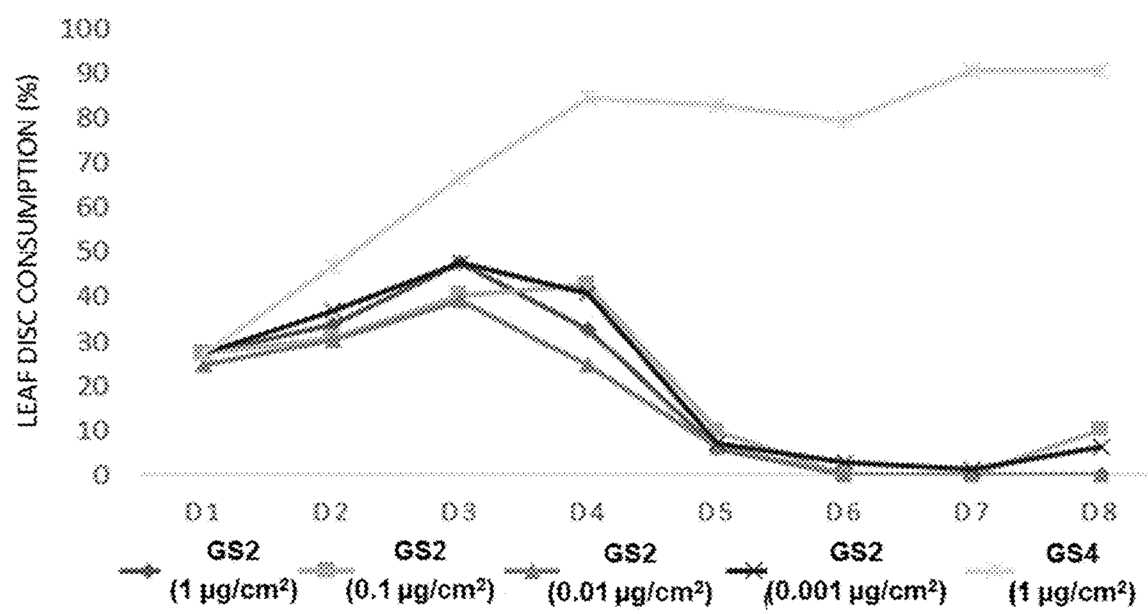

A dose-titration of the GS2 composition was also performed to determine if a lower concentration of the GS2 PSMB5 RNAi polynucleotide is equally effective in controlling CPBs. Up to 90% of CPBs died following exposure to GS2 at 1.0 $m/cm^2$, 0.1 $m/cm^2$, and 0.01 $m/cm^2$, about 80% of CPBs died following exposure to GS2 at 0.001 $m/cm^2$ compared to a control (GS4) composition at 1.0$m/cm^2$ (FIG. 2A). Potato leaf consumption also decreased to nearly 0% when CPBs were exposed to GS2 at 1.0 m/cm$^2$, 0.1 m/cm$^2$, 0.01 m/cm$^2$, and 0.001 m/cm$^2$ compared to a control (GS4) composition at 1.0 m/cm$^2$ (FIG. 2B).

Exposure of CPBs to the PSMB5 RNAi polynucleotide GS2 composition administered to potato leaves at a concentration of as low as 0.0001 m/cm$^2$ results in a 90% mortality and a 95% decreased potato leaf consumption compared to CPBs exposed to a control.

Example 2

Figure 3A:
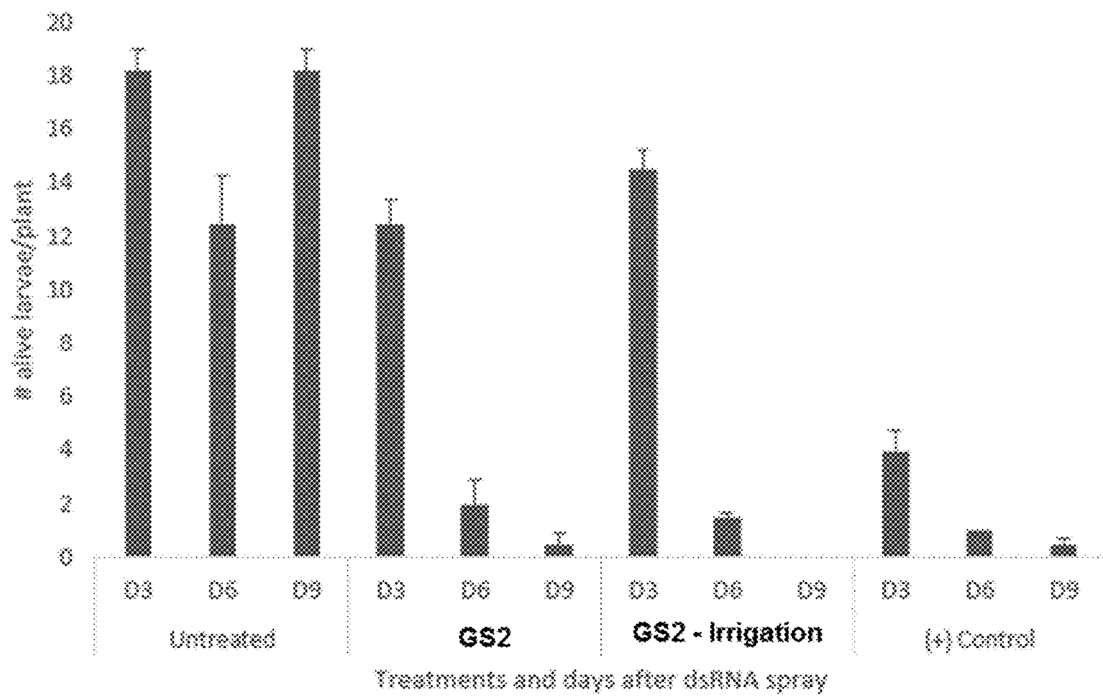
FIGS. 3A-3B include graphs showing the of live CPB larvae per plant (FIG. 3A) and percent plant defoliation (FIG. 3B) following leaf treatment with either a PSMB5 RNAi composition of the present disclosure (GS2), a PSMB5 RNAi composition followed by irrigation (approximately 500 ml of water per plant, simulating ½ inch of rain), a control composition (+control), or no treatment (untreated).
Figure 3B:
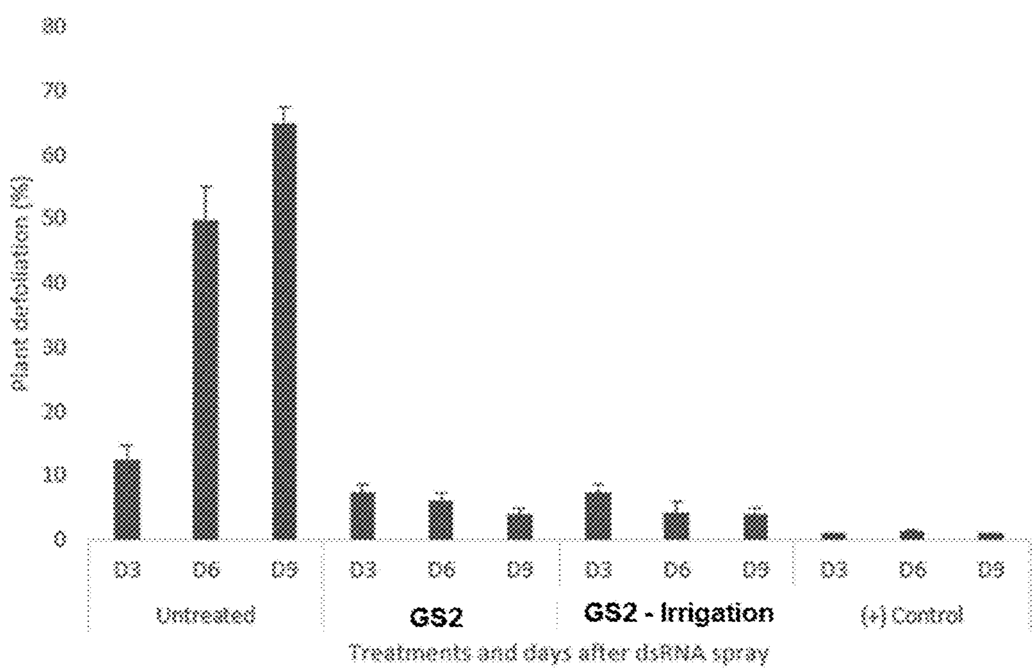

Application of a PSMB5 RNAi Composition (GS2) to Plants Controls Colorado Potato Beetles The composition comprising PSMB5 RNAi polynucleotide (GS2) of Example 1 was tested for its effectiveness in controlling the numbers of Colorado potato beetles (CPBs) on a potato plant. Briefly, the GS2 composition, a composition comprising CORAGEN® (+control; an agent known to kill CPBs), or no treatment was applied to the leaves of potato plants and allowed to dry. The effect of irrigation on GS2 composition efficacy was also tested. The number of CPB larvae per plant was decreased by about 90% in potato plants treated with GS2, regardless of irrigation, relative to untreated potato plants (FIG. 3A). The percent of potato plant defoliation was also decreased by about 60% when the plants were treated with GS2, regardless of irrigation, relative to untreated potato plants (FIG. 3B).

Exposure of CPBs to the PSMB5 RNAi polynucleotide in the GS2 composition administered to potato plants decreased the numbers of live larvae per plant by about 90% and the plant defoliation by about 60% compared to CPBs exposed to potato plants that were untreated.

Example 3

A PSMB5 RNAi Composition (GS2) Kills Colorado Potato Beetles

Figure 4A:
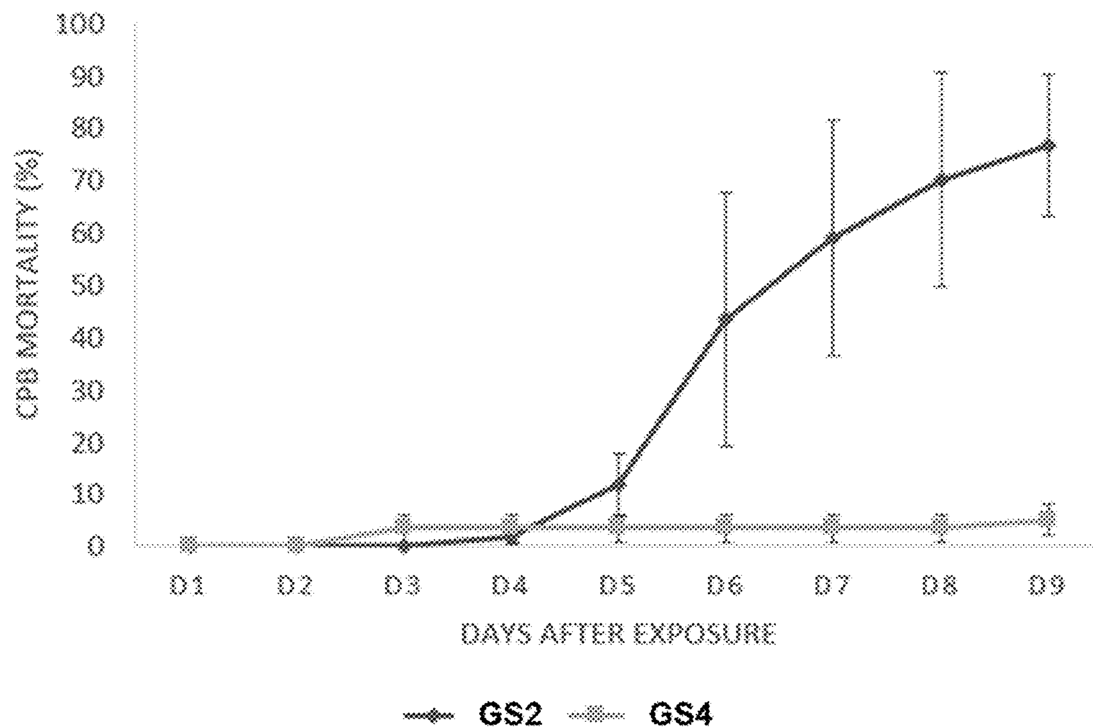
FIGS. 4A-4B include graphs showing the percent mortality of Colorado potato beetles (CPBs) (FIG. 4A) and percent leaf disc consumption by CPBs (FIG. 4B) following a nine-day exposure of the CPBs to either a PSMB5 RNAi (GS2) composition of the present disclosure or to a control RNAi (GS4) composition (10 μg/cm$^2$ concentration of RNAi).
Figure 4B:
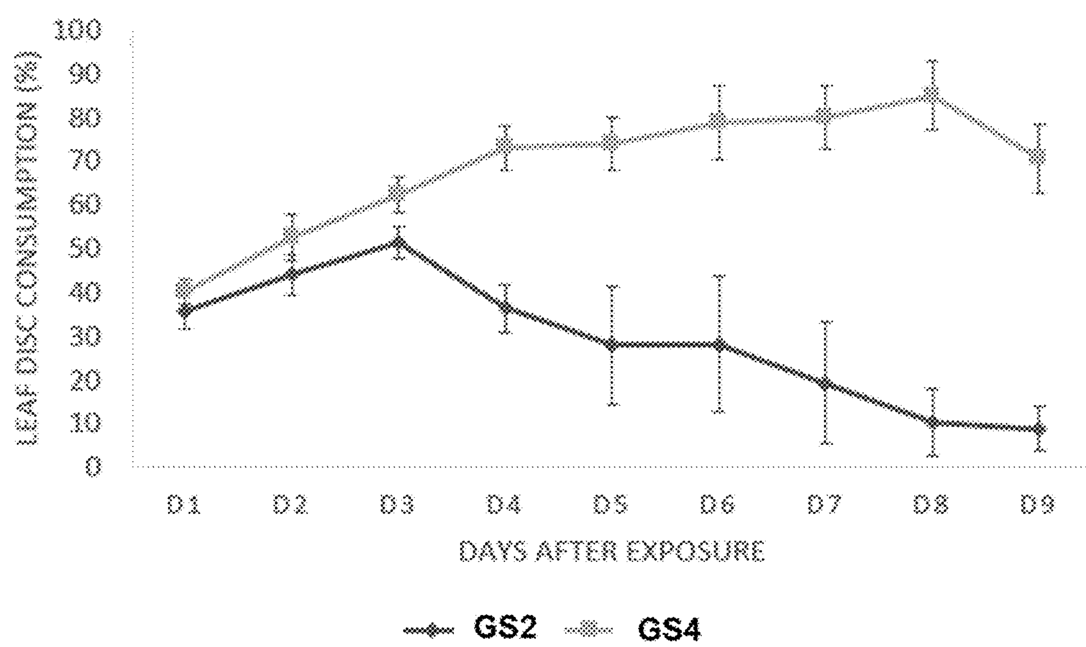

The composition comprising PSMB5 RNAi polynucleotide (GS2) of Example 1 was sprayed (at a concentration of 10 μg/cm$^2$) onto the leaves of potato plants and allowed to dry. Up to 75% of CPBs died following a 9-day exposure to the GS2-covered potato plant leaves compared with less than 10% of CPBs that die following exposure to the GS4 control (GS4) leaves (FIG. 4A). This increased mortality in response to exposure to GS2 also results in a decrease of potato leaf consumption below 15% compared to CPBs exposed to the GS4 control (FIG. 4B).

A dose-titration of the GS2 composition was also performed to determine if a lower concentration of the GS2 PSMB5 RNAi polynucleotide is equally effective in controlling CPBs.

Figure 5A:
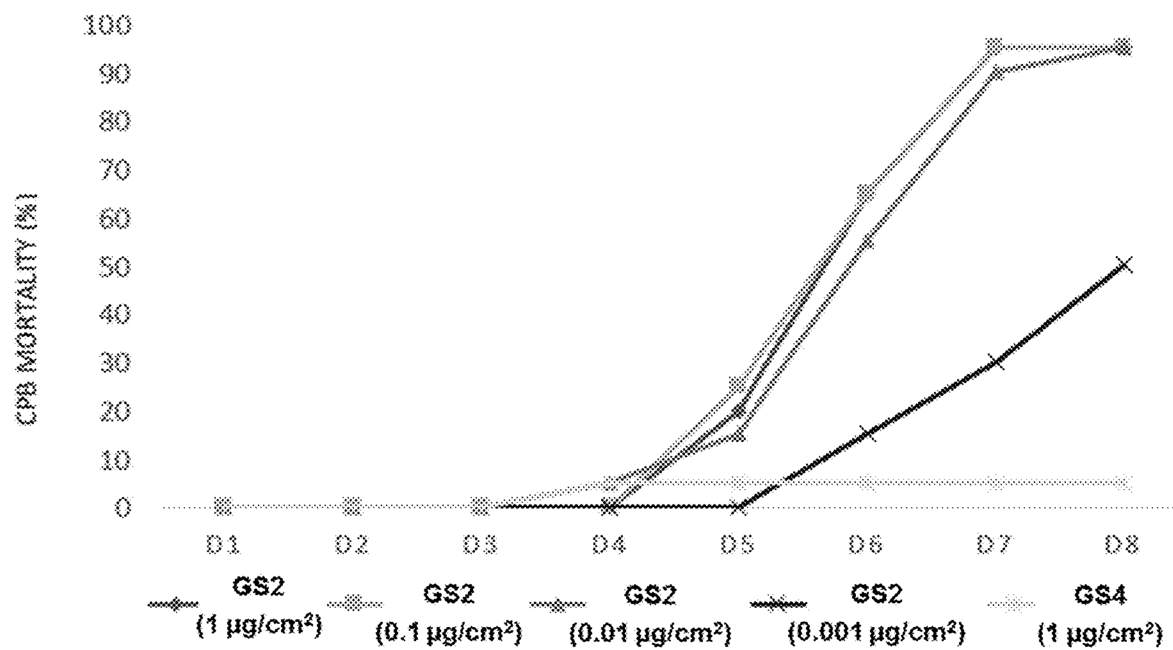
FIGS. 5A-5B include graphs showing the percent mortality of Colorado potato beetles (CPBs) (FIG. 5A) and percent leaf disc consumption by CPBs (FIG. 5B) following a three-day dose-trial course in CPBs exposed to either a PSMB5 RNAi composition of the present disclosure (GS2 at 1.0 μg/cm$^2$, 0.1 μg/cm$^2$, 0.01 μg/cm$^2$, or 0.001 μg/cm$^2$) or a control RNAi composition (GS4 at 1.0 μg/cm$^2$).
Figure 5B:
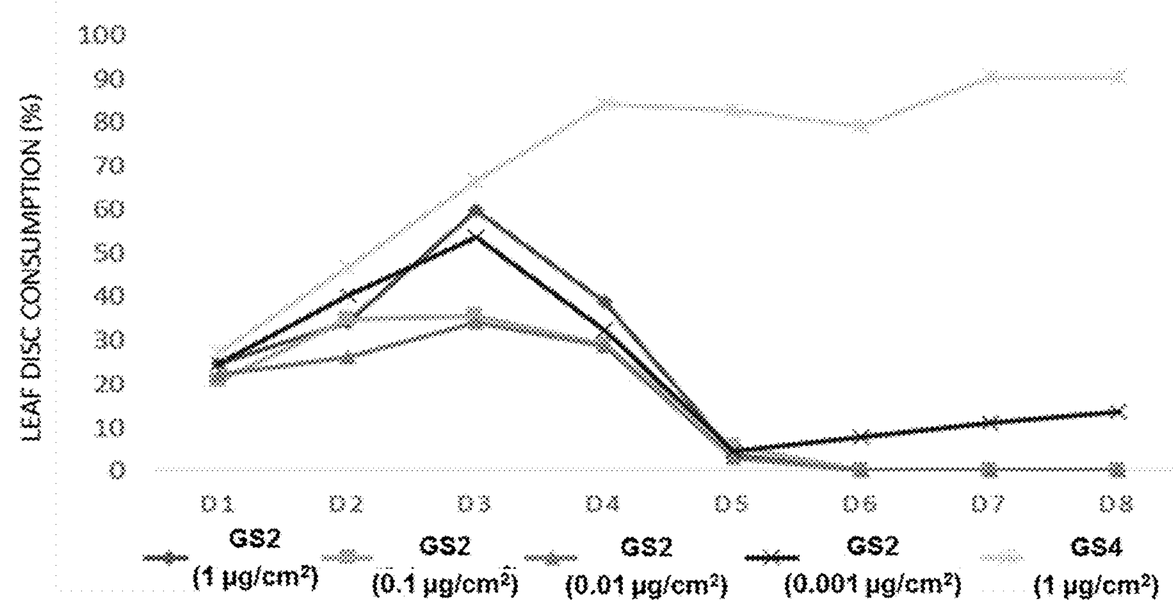

Up to 90% of CPBs died following exposure to GS2 at 1.0 μg/cm$^2$, 0.1 μg/cm$^2$, and 0.01 μg/cm$^2$, about 50% of CPBs died following exposure to GS2 at 0.001 μg/cm$^2$ compared to a control (GS4) composition at 1.0 μg/cm$^2$ (FIG. 5A). Potato leaf consumption also decreased to nearly 0% when CPBs were exposed to GS2 at 1.0 μg/cm$^2$, 0.1 μg/cm$^2$, and 0.01 μg/cm$^2$, and to below 15% when CPBs were exposed to GS2 at 0.001 μg/cm$^2$ compared to a control (GS4) composition at 1.0 μg/cm$^2$ (FIG. 5B).

Exposure of CPBs to the PSMB5 RNAi polynucleotide GS2 composition administered to potato leaves at a concentration of as low as 0.0001 μg/cm$^2$ results in a 90% mortality and a 95% decreased potato leaf consumption compared to CPBs exposed to a control.

Example 4

PSMB5 RNAi Compositions Spanning the Length of the PSMB5 Gene are Effective at Controlling Colorado Potato Beetle (CPB) Infestation Four dsRNA molecules that collectively bind to the entire length of messenger RNA (mRNA) (SEQ ID NO: 18) encoded by a Coleoptera PSMB5 gene (SEQ ID NO: 1) were evaluated for their effectiveness to control Colorado potato beetle (CPB) infestation. The dsRNA molecules used in this Example were: GS2, GS47, GS180, GS181, and the negative control molecule (GS4).

For each dsRNA, five leaves (−20 days old) were cut from an eggplant plant, coated with 0.5 of dsRNA, and dried for about 30 min. Each of the four leaves was placed into four different Petri dishes (100 mm×15 mm) on a moisture filter paper. For each petri dish, five 'second instar' CPB larvae were placed on top of each leaf and the dishes kept at room temperature. On Day 3 (after 72 hours) and Day 6 (after 144 hours), new dsRNA-treated leaves were placed into the Petri dishes. The total number of CPB insects was counted in each experiment on Days 3, 6, 7, 8, and 9. For purposes of determining mortality caused by each dsRNA, the initial count of living CPB insects was established on Day 2. Any CPB insects that were already dead on Day 2 were assumed to be dead because of handling conditions or initial insect health conditions. Each dsRNA experiment was duplicated using different batches of insects on different weeks, each comprising four different leaf Petri dishes).

Figure 6:
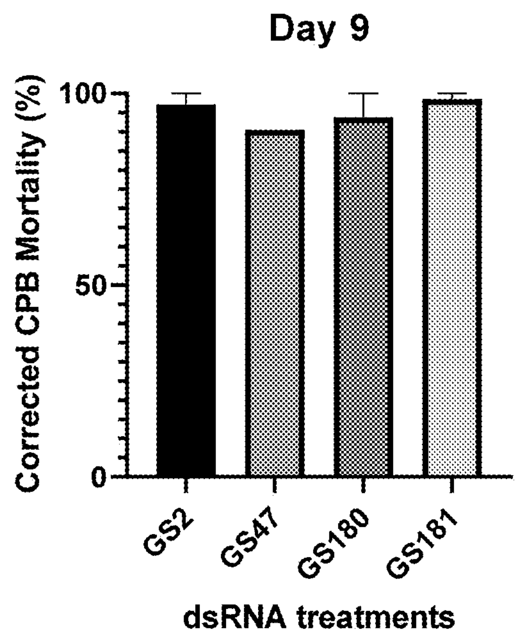
FIG. 6 includes a graph showing the percent mortality of Colorado potato beetles (CPBs) nine days after oral exposure to an RNAi composition that includes a double-stranded RNA (dsRNA) that targets a PSMB5 mRNA encoded by a 5' terminal region of PSMB5 DNA (GS47), an RNAi composition that includes a dsRNA that targets a PSMB5 mRNA encoded by a central region of PSMB5 DNA (GS180), an RNAi composition that includes a dsRNA that targets a PSMB5 mRNA encoded by a 3' terminal region of PSMB5 DNA (GS181), or a negative control RNAi composition (GS4).

All of tested dsRNA molecules (GS2, GS47, GS180, and GS181) that bind to an mRNA encoded by a Coleoptera PSMB5 gene caused significant time-dependent mortality in CPB insects (Table 1). After nine days of exposure, GS2 caused an average 97% mortality in CPB insects; GS47 caused an average 95% mortality in CPB insects; GS180 caused an average 94% mortality in CPB insects; and GS181 caused an average 99% mortality in CPB insects (FIG.6; mortality corrected using Sun-Shepard's formula (Püntener 1981)). Conversely, the negative control (GS4) only caused an average 34% mortality (Table 1).

TABLE 1

Average mortality caused by dsRNA molecules that target length of PSMB5 gene (combined replicates)

| | # of Insects on Day 2 | Day 3 Mortality | Day 6 Mortality | Day 7 Mortality | Day 8 Mortality | Day 9 Mortality |
|---|---|---|---|---|---|---|
| GS4 | #1: 22, #2: 24, #3: 19 | 5% | 21% | 26% | 31% | 34% |
| GS2 | #1: 24, #2: 24, #3: 20 | 5% | 51% | 84% | 93% | 97% |
| GS47 | #1: 19 | 5% | 85% | 95% | 95% | 95% |
| GS180 | #1: 20, #2: 24, #3: 21 | 8% | 55% | 88% | 91% | 94% |
| GS181 | #1: 21, #2: 23, #3: 21 | 5% | 53% | 86% | 97% | 99% |

Example 5

PSMB5 RNAi Compositions of Minimal Length (49-200 nucleotides) are Effective at Controlling Colorado Potato Beetles Five dsRNA molecules comprising sequences of minimal length (49-200 nucleotides) that bind to a messenger RNA (mRNA) (e.g., SEQ ID NO: 18) encoded by a Coleoptera PSMB5 gene (e.g., SEQ ID NO: 1) were evaluated for their effectiveness to control Colorado potato beetles (CPBs). The evaluated dsRNA molecules were: GS188, GS189, GS190, GS191, GS192, GS2, and the negative control (GS4).

GS188, and GS189 were tested with GS4 and GS2 according to the procedure described in Example 4.

GS190, GS191, and GS192 were tested with GS4 and GS2 at a concentration of 0.0189 using fifteen eggplant leaves, each with a single 'second instar' CPB larvae. GS191 and GS192 comprised sequences of complementarity to PSMB5 mRNA flanked by a T7 promoter and a restriction site.

Figure 7A:
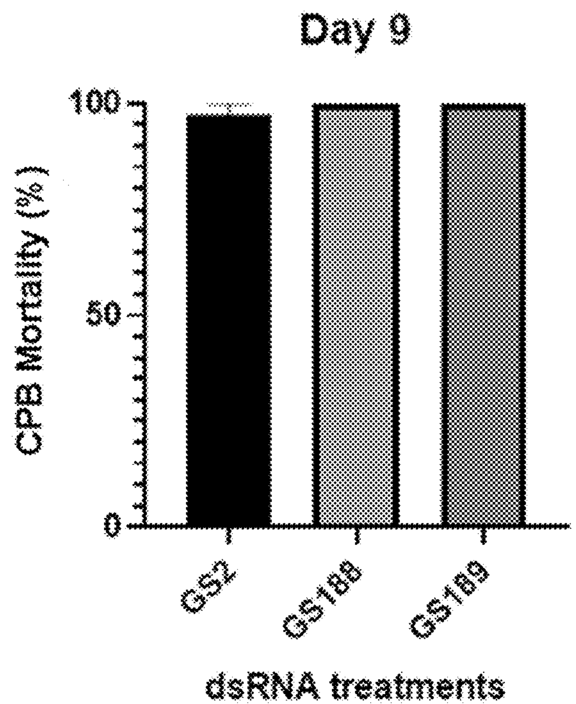
FIGS. 7A-7B include graphs showing the percent mortality of CPBs nine days after oral exposure to an RNAi composition that includes a dsRNA that targets PSMB5 mRNA. The dsRNA varied in size, with GS2 having a length of 460-nucleotides, GS188 having a length of 200-nucleotides, GS189 having a length of 150-nucleotides (FIG. 6A), G190 having a length of 100-nucleotides, GS191 having a length of 74 nucleotides, with 50 complementary nucleotides, and GS192 having a length of 49 nucleotides with 25 complementary nucleotides (FIG. 6B). A negative control RNAi composition (GS4) was further evaluated.

All of tested dsRNA molecules comprising 100-200 nucleotides that bind to an mRNA encoded by a Coleoptera PSMB5 gene (GS188, GS189, GS190) caused significant time-dependent mortality in CPB insects (Table 2). After nine days of exposure, the 200-nucleotide length dsRNA molecule (GS188) caused an average 100% mortality in CPB insects; and the 150-nucleotide length dsRNA molecule (GS189) caused an average 100% mortality in CPB insects. Each of these dsRNA molecules functioned to control/kill CPB insects at similar levels as the 460-nucleotide length dsRNA molecule (GS2). Conversely, the negative control (GS4) only caused an average 34% mortality (FIG. 7A).

Figure 7B:
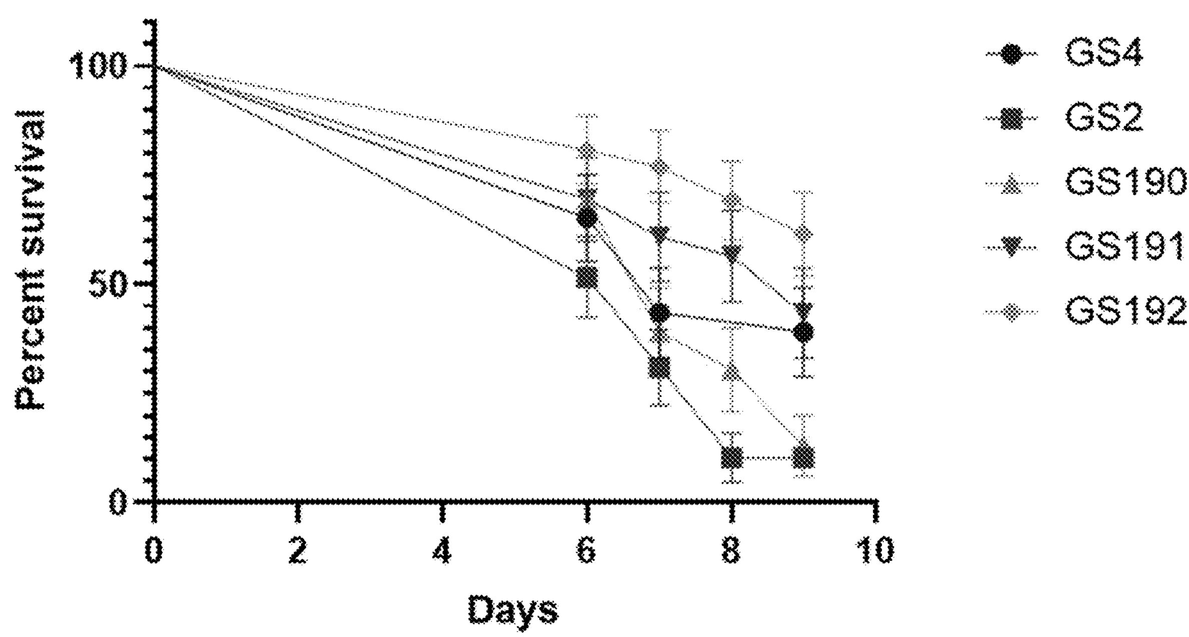

The dsRNA molecules comprising 49-nucleotides (GS192), 74-nucleotides (GS191), and 100-nucleotides (GS190), respectively, caused time-dependent mortality in CPB insects (Table 3). After nine days of exposure, the 49-nucleotide length dsRNA molecule (GS192) caused an average 38% mortality in CPB insects; the 74-nucleotide length dsRNA molecule (GS191) caused an average 56% mortality in CPB insects (statistically similar to mortality in controls, which was around 62%); and the 100-nucleotide length dsRNA molecule (GS190) caused an average 88% mortality in CPB insects (statistically similar to mortality caused by GS2, which was 90%) (FIG. 7B).

TABLE 2

Average mortality of two biological replicates caused by dsRNA molecules comprising 150-200 nucleotides that target PSMB5 gene (combined replicates)

| | dsRNA length (nucleotides) | # of Insects on Day 2 | Day 3 | Day 6 | Day 7 | Day 8 | Day 9 |
|---|---|---|---|---|---|---|---|
| GS4 | 524 | #1: 22, #2: 24, #3: 19 | 5% | 21% | 26% | 31% | 34% |
| GS2 | 460 | #1: 24, #2: 24, #3: 20 | 5% | 51% | 84% | 93% | 97% |
| GS188 | 200 | #1: 24, #2: 23, #3: 19 | 4% | 73% | 97% | 99% | 100% |
| GS189 | 150 | #1: 25, #2: 23, #3: 20 | 7% | 67% | 87% | 92% | 100% |

TABLE 3

Mortality caused by dsRNA molecules comprising 25-100 nucleotides that complementary bind to the target P5MB5 mRNA gene

| | dsRNA length (nucleotides) | # of Insects on Day 2 | Day 6 | Day 7 | Day 8 | Day 9 |
|---|---|---|---|---|---|---|
| GS4 | 524 | #1: 11, #2: 12 | 40% | 57% | 57% | 62% |
| GS2 | 460 | #1: 15, #2: 14 | 48% | 69% | 90% | 90% |
| GS190 | 100 | #1: 12, #2: 11 | 30% | 61% | 70% | 88% |
| GS191 | 50 | #1: 11, #2: 12 | 34% | 43% | 43% | 56% |
| GS192 | 25 | #1: 13, #2: 13 | 19% | 23% | 31% | 38% |

Example 6

PSMB5 RNAi Compositions Comprising a Sequence That Have 70-95% Complementarity to a PSMB5 mRNA are Effective at Controlling Colorado Potato Beetles The 460-nucleotide dsRNA (GS2) that binds to a messenger RNA (mRNA) encoded by a Coleoptera PSMB5 gene was mutated to evaluate the ability of dsRNA molecules comprising mismatches to control/kill CPB insects. The evaluated dsRNA molecules were dsRNA: (1) having 70% sequence identity to GS2 (GS182); (2) having 75% sequence identity to GS2 (GS183); (3) having 80% sequence identity to GS2 (GS184); (4) having 85% sequence identity to GS2 (GS185); (5) having 90% sequence identity to GS2 (GS186); and having 95% sequence identity to GS2 (GS187). The sequence of GS182 is 70% complementary to an mRNA encoded by a PSMB5 gene; GS183 is 75% complementary to an mRNA encoded by a PSMB5 gene; GS184 is 80% complementary to an mRNA encoded by a PSMB5 gene; GS185 is 85% complementary to an mRNA encoded by a PSMB5 gene; GS186 is 90% complementary to an mRNA encoded by a PSMB5 gene; and GS187 is 95% complementary to an mRNA encoded by a PSMB5 gene.

All dsRNA molecules were tested with GS4 and GS2 according to the procedure described in Example 4.

Figure 8:
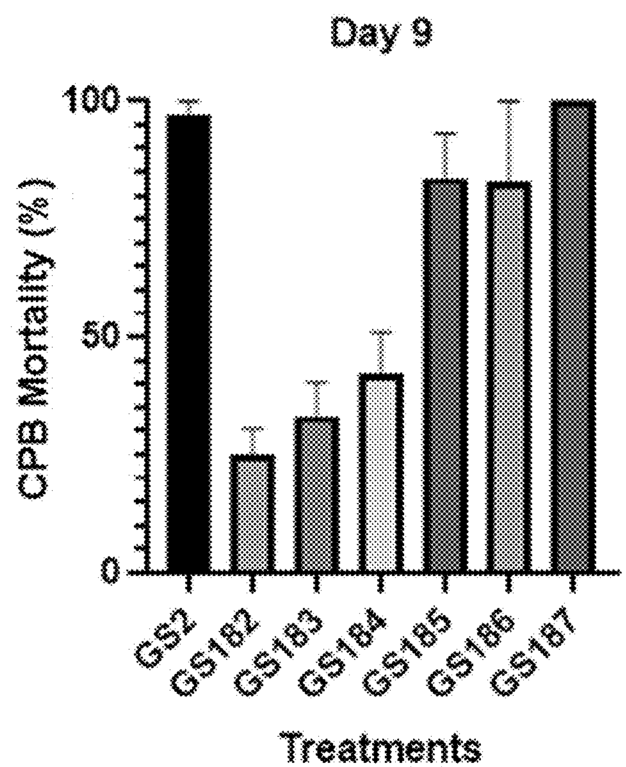
FIG. 8 includes a graph showing the percent mortality of CPBs nine days after oral exposure to an RNAi composition that includes a dsRNA that is 70% (GS182), 75% (GS183), 80% (GS184), 85% (GS185), 90% (GS186), or 95% (GS187) complementary to a PSMB5 mRNA across a region having a length of 460-nucleotides (GS2). A negative control RNAi composition (GS4) was further evaluated.
Figure 9:
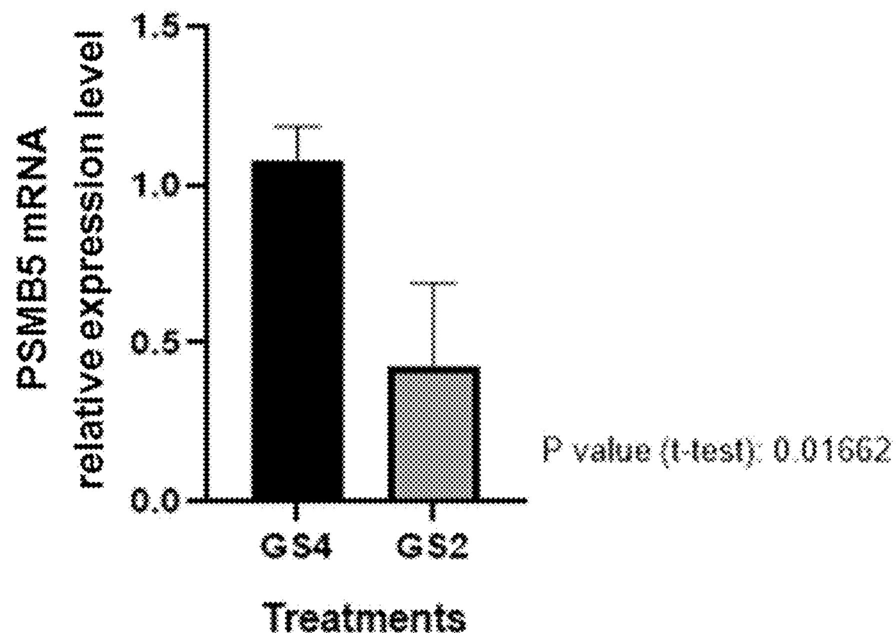
FIG. 9 includes a graph showing the PSMB5 mRNA relative expression level of second instar CPB larvae fed on leaves coated with GS2 and GS4 (2 μL of RNAi composition at 0.026 μg/μL) for two days and collected after two days. Relative expression levels were normalized using the endogenous control RP4 gene and calculated using $2^{-ddCt}$ method. (n=3)

All tested dsRNA caused time-dependent mortality in CPB insects (Table 4). In particular, after nine days of exposure, GS183 (75% complementary to a PSMB5 mRNA) caused an average 56% mortality in CPB insects; GS184 (80% complementary to a PSMB5 mRNA) caused an average 60% mortality in CPB insects; GS185 (85% complementary to a PSMB5 mRNA) caused an average 87% mortality in CPB insects; GS186 (85% complementary to a PSMB5 mRNA) caused an average 84% mortality in CPB insects; and GS187 (85% complementary to a PSMB5 mRNA) caused an average 100% mortality in CPB insects. dsRNA molecules that were 85% complementary to an mRNA encoded by a PSMB5 gene functioned to control/kill CPB insects at similar levels as the dsRNA molecule that was 100% complementary to an mRNA encoded by a PSMB5 gene (GS2) (FIG. 8; mortality corrected using Sun-Shepard's formula).

TABLE 4

Average Mortality of two biological replicates caused by dsRNA molecules comprising sequences with variable complementarity to an mRNA encoded by a PSMB5 gene (combined replicates)

| | Complementarity to PSMB5 mRNA | # of Insects on Day 2 | Day 3 Mortality | Day 6 Mortal-ty | Day 7 Mortality | Day 8 Mortality | Day 9 Mortality |
|---|---|---|---|---|---|---|---|
| GS4 | | #1: 22, #2: 24, #3: 19 | 5% | 21% | 26% | 31% | 34% |
| GS2 | 100% | #1: 24, #2: 24, #3: 20 | 5% | 51% | 84% | 93% | 97% |
| GS182 | 70% | #1: 23, #2: 25, #3: 21 | 11% | 27% | 43% | 46% | 50% |
| GS183 | 75% | #1: 21, #2: 22, #3: 22 | 6% | 36% | 46% | 49% | 56% |
| GS184 | 80% | #1: 23, #2: 24, #3: 23 | 9% | 23% | 47% | 52% | 60% |
| GS185 | 85% | #1: 22, #2: 23, #3: 25 | 6% | 51% | 68% | 81% | 87% |
| GS186 | 90% | #1: 22, #2: 21, #3: 22 | 11% | 53% | 73% | 72% | 84% |
| GS187 | 95% | #1: 19, #2: 23, #3: 22 | 15% | 69% | 84% | 96% | 100% |

Example 7

A PSMB5 RNAi Composition (GS2) Controls Colorado Potato Beetles in Field Trials

A 460-nucleotide PSMB5 RNAi composition (GS2) that binds to a messenger RNA (mRNA) encoded by a Coleopteran PSMB gene was evaluated for its ability to control CPB insects in five open-air field trials. Briefly, in each field trial, a composition comprising GS2 (2-200 grams/acre); one or more positive control compositions (standards) comprising CORAGEN® (73 grams/acre) and/or ENTRUST® (88 grams/acre); or no treatment (negative control) was applied to the leaves of potato or eggplant plants in an open field. The PSMB5 RNAi composition (GS2) and the standards were applied to leaves in three or four applications on seven-day intervals (Days 0, 7, 14, and 21). Percent defoliation of the potato leaves was assessed at Days 6, 13, 20 and 27; or Days 13 and 20 after the first application; percent remaining foliage of the potato leaves was assessed at Days 13, 16, 20, and 23 after the first application; and percent defoliation of the eggplant leaves was assessed at Days 5, 14, and 21 or Days 4, 14, and 30 after the first application.

Figure 10A:
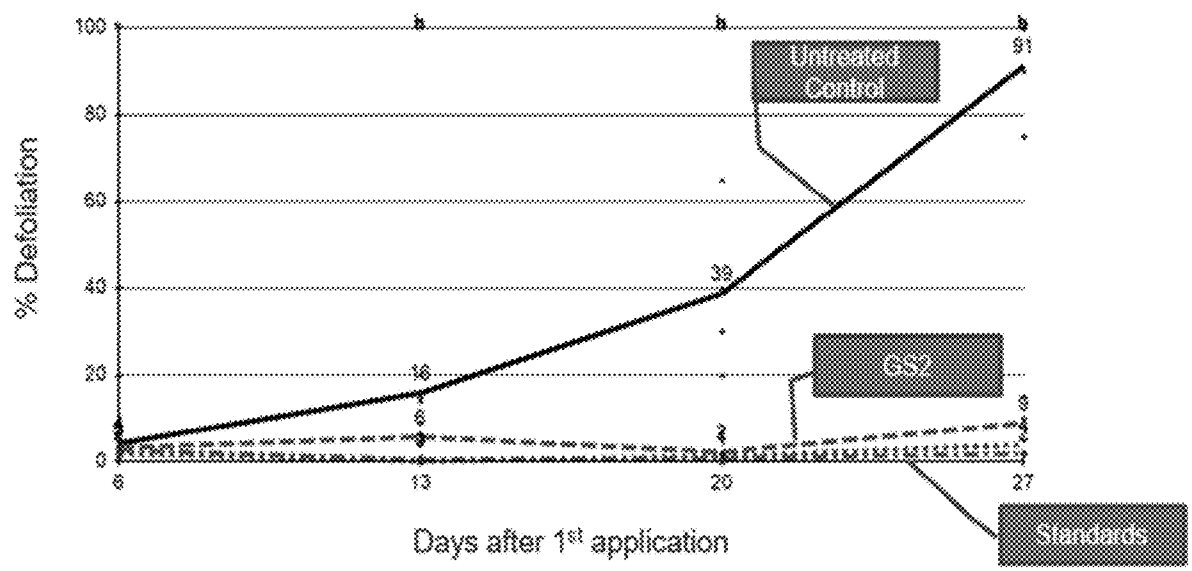
FIGS. 10A-10E include graphs showing the percent plant defoliation and the percent remaining plant foliage following leaf treatment in field trials with a PSMB5 RNAi composition (GS2), positive control compositions (standards, e.g., CORAGEN®, ENTRUST®) and no treatment (untreated control) over a 20-30 day period.

In field trial #1 (FIG. 10A), untreated potato plants were 39% defoliated at Day 20. Conversely, potato plants treated with GS2 were 2% defoliated at Day 20; and plants treated with standards (e.g. CORAGEN® and ENTRUST®) were less than 2% defoliated at Day 20.

Figure 10B:
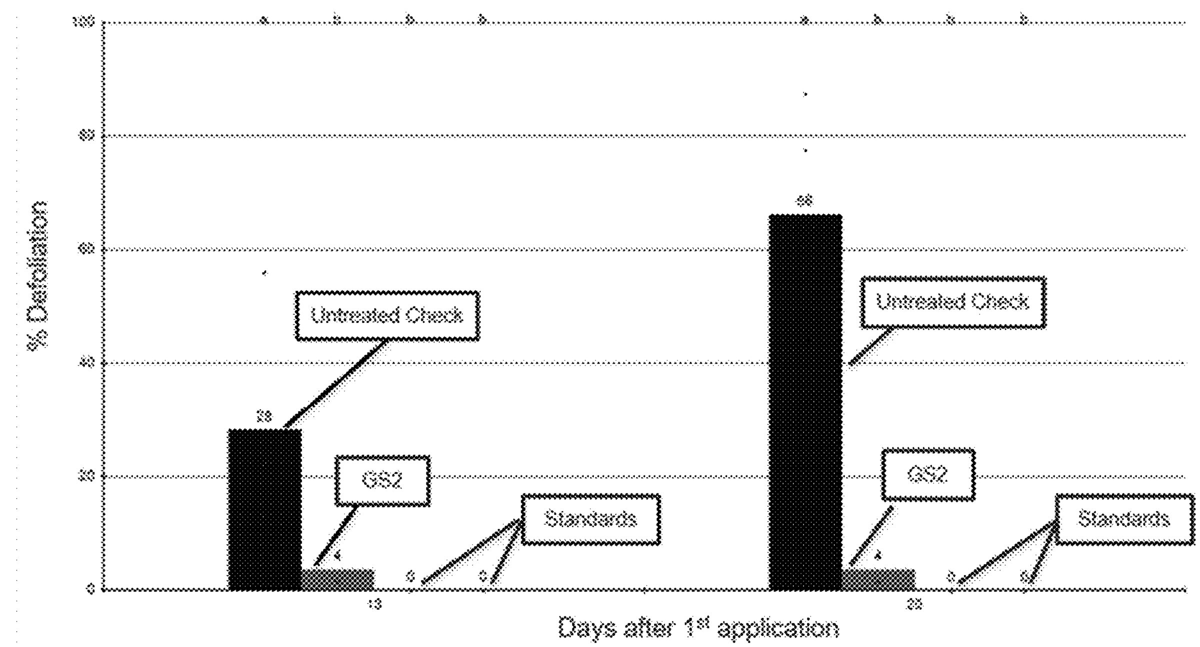

In field trial #2 (FIG. 10B), untreated potato plants were 66% defoliated at Day 20. Conversely, potato plants treated with GS2 were approximately 4% defoliated at Day 20; and plants treated with standards (e.g. CORAGEN®, ENTRUST®) were 0% defoliated at Day 20.

Figure 10C:
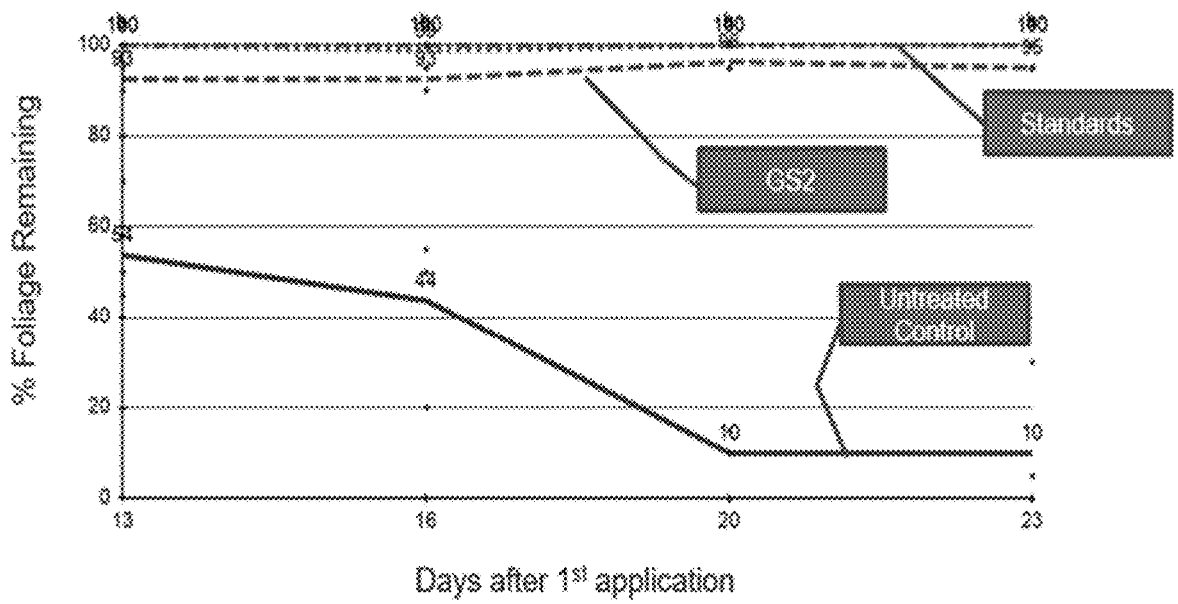

In field trial #3 (FIG. 10C), untreated potato plants had less than 10% foliage at Day 23. Conversely, potato plants treated with GS2 had approximately 93% foliage at Day 23; and plants treated with standards (e.g. CORAGEN® and ENTRUST®) had approximately 95% foliage at Day 23.

Figure 10D:
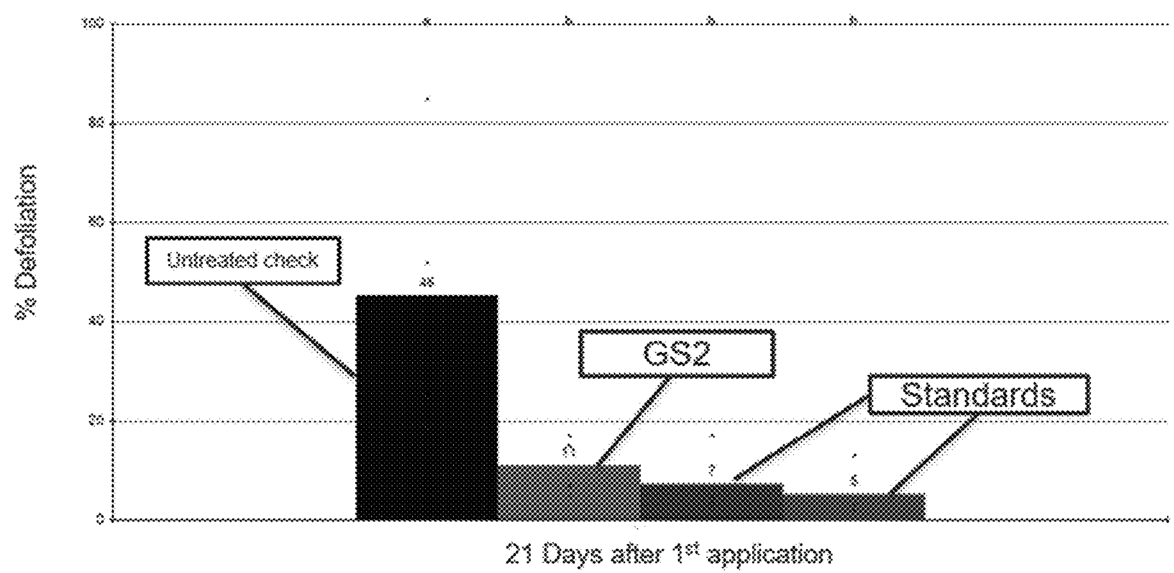

In field trial #4 (FIG. 10D), untreated eggplant plants were approximately 45% defoliated at Day 21. Conversely, eggplant plants treated with GS2 were approximately 11% defoliated at Day 21; and plants treated with standards (e.g. CORAGEN® and ENTRUST®) were less than 10% defoliated at Day 21.

Figure 10E:
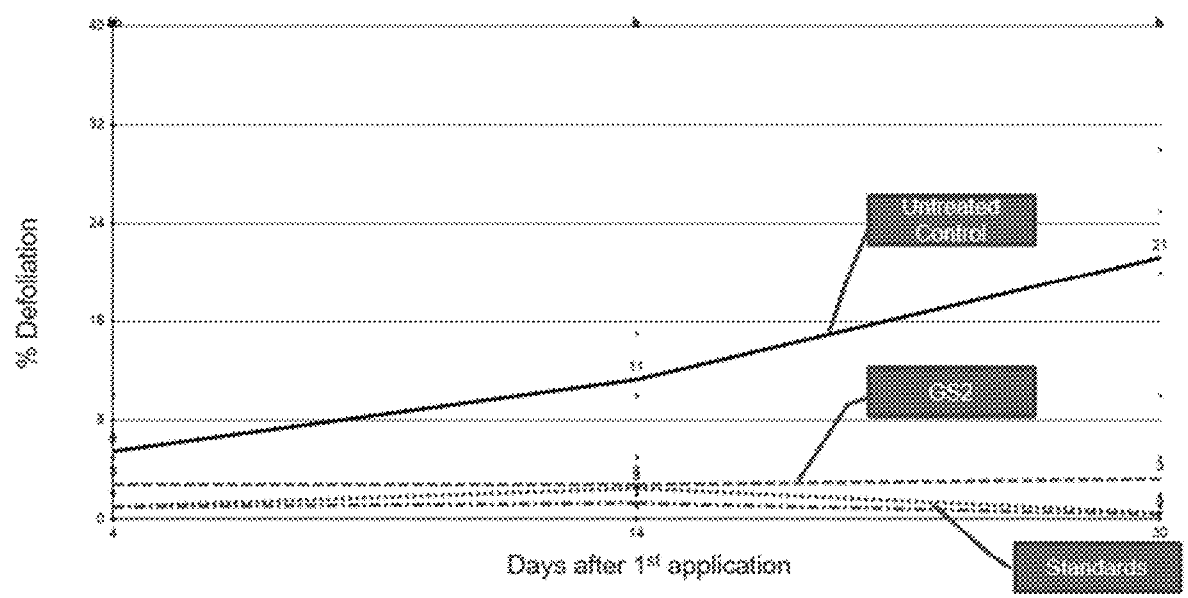

In field trial #5 (FIG. 10E), untreated eggplant plants were approximately 21% defoliated at Day 30. Conversely, eggplant plants treated with GS2 were less than 3% defoliated at Day 30; and plants treated with standards (e.g. CORAGEN® and ENTRUST®) were 0% defoliated at Day 30.

These data demonstrate that application of PSMB5 RNAi compositions of the disclosure prevent defoliation of plants (e.g., potato or eggplant plants) when applied to the leaves of plants in open fields (e.g., fields of crops).

Additional Embodiments

Additional embodiments of the present disclosure are encompassed by the following numbered paragraphs.

1. A polynucleotide molecule targeting a Coleopteran Proteasome Beta 5 (PSMB5) gene, wherein the polynucleotide molecule is selected from the group consisting of:

a polynucleotide molecule that binds to and inhibits expression of a messenger RNA (mRNA) encoded by a deoxynucleic acid (DNA) comprising a sequence of SEQ ID NO: 1;

a polynucleotide molecule that binds to and inhibits expression of a mRNA comprising a sequence of any one of SEQ ID NOS: 18 or 19;

a polynucleotide molecule that comprises a sequence having at least 80% identity to a sequence of any one of SEQ ID NOS: 18, 19, 35, or 36; and a polynucleotide molecule that comprises a segment that comprises at least 18 contiguous nucleotides, wherein the segment has at least 90% identity to a segment of a sequence of any one of SEQ ID NOS: 18, 19, 35, or 36.

2. The polynucleotide molecule of paragraph 1, wherein the polynucleotide molecule binds to a sequence of SEQ ID NO: 18.

3. The polynucleotide molecule of paragraph 1 or 2, wherein the polynucleotide molecule comprises a sequence that has at least 85%, at least 90%, at least 95%, or at least 98% identity to a sequence of any one of SEQ ID NOS: 19 or 36.

4. The polynucleotide molecule of paragraph 1 or 2, wherein the polynucleotide molecule comprises a segment that comprises at least 18 contiguous nucleotides, wherein the segment shares at least 95% or at least 98% identity with a sequence of any one of SEQ ID NOS: 19 or 36.

5. The polynucleotide molecule of paragraph 3 or 4, wherein the polynucleotide molecule comprises the sequence of any one of SEQ ID NOS: 19 or 36.

6. The polynucleotide molecule of any one of paragraphs 1-5, wherein the polynucleotide molecule is a single-stranded RNA (ssRNA) molecule, optionally comprising the sequence of SEQ ID NO: 36 or a segment of SEQ ID NO: 36.

7. The polynucleotide molecule of paragraph 6, wherein the ssRNA molecule is selected from the group consisting of small interfering RNAs (siRNAs), short hairpin RNAs (shRNAs), microRNAs (miRNAs), and antisense RNAs.

8. The polynucleotide molecule of any one of paragraphs 1-5, wherein the polynucleotide molecule is a double-stranded RNA (dsRNA) molecule, optionally comprising the sequence of SEQ ID NO: 19 or 36 or a segment of SEQ ID NO: 19 or 36.

9. A polynucleotide that specifically inhibits expression of a Coleopteran proteasome beta 5 (PSMB5) gene, wherein the polynucleotide comprises a first strand comprising the sequence of any one of SEQ ID NO: 19 or 21-34.

10. A polynucleotide that specifically inhibits expression of a Coleopteran proteasome beta 5 (PSMB5) gene, wherein the polynucleotide comprises a strand comprising the sequence of any one of SEQ ID NO: 36 or 38-51.

11. The polynucleotide of paragraph 9, wherein the polynucleotide comprises a first strand consisting of the sequence of SEQ ID NO: 19, optionally further comprising a second strand consisting of the sequence of SEQ ID NO: 36.

12. The polynucleotide of paragraph 9, wherein the polynucleotide comprises a first strand consisting of the sequence of SEQ ID NO: 21, optionally further comprising a second strand consisting of the sequence of SEQ ID NO: 38.

13. The polynucleotide of paragraph 9, wherein the polynucleotide comprises a first strand consisting of the sequence of SEQ ID NO: 22, optionally further comprising a second strand consisting of the sequence of SEQ ID NO: 39.

14. The polynucleotide of paragraph 9, wherein the polynucleotide comprises a first strand consisting of the sequence of SEQ ID NO: 23, optionally further comprising a second strand consisting of the sequence of SEQ ID NO: 40.

15. The polynucleotide of paragraph 9, wherein the polynucleotide comprises a first strand consisting of the sequence of SEQ ID NO: 24, optionally further comprising a second strand consisting of the sequence of SEQ ID NO: 41.

16. The polynucleotide of paragraph 9, wherein the polynucleotide comprises a first strand consisting of the sequence of SEQ ID NO: 25, optionally further comprising a second strand consisting of the sequence of SEQ ID NO: 42.

17. The polynucleotide of paragraph 9, wherein the polynucleotide comprises a first strand consisting of the sequence of SEQ ID NO: 26, optionally further comprising a second strand consisting of the sequence of SEQ ID NO: 43.

18. The polynucleotide of paragraph 9, wherein the polynucleotide comprises a first strand consisting of the sequence of SEQ ID NO: 27, optionally further comprising a second strand consisting of the sequence of SEQ ID NO: 44.

19. The polynucleotide of paragraph 9, wherein the polynucleotide comprises a first strand consisting of the sequence of SEQ ID NO: 28, optionally further comprising a second strand consisting of the sequence of SEQ ID NO: 45.

20. The polynucleotide of paragraph 9, wherein the polynucleotide comprises a first strand consisting of the sequence of SEQ ID NO: 29, optionally further comprising a second strand consisting of the sequence of SEQ ID NO: 46.

21. The polynucleotide of paragraph 9, wherein the polynucleotide comprises a first strand consisting of the sequence of SEQ ID NO: 30, optionally further comprising a second strand consisting of the sequence of SEQ ID NO: 47.

22. The polynucleotide of paragraph 9, wherein the polynucleotide comprises a first strand consisting of the sequence of SEQ ID NO: 31, optionally further comprising a second strand consisting of the sequence of SEQ ID NO: 48.

23. The polynucleotide of paragraph 9, wherein the polynucleotide comprises a first strand consisting of the sequence of SEQ ID NO: 32, optionally further comprising a second strand consisting of the sequence of SEQ ID NO: 49.

24. The polynucleotide of paragraph 9, wherein the polynucleotide comprises a first strand consisting of the sequence of SEQ ID NO: 33, optionally further comprising a second strand consisting of the sequence of SEQ ID NO: 50.

25. The polynucleotide of paragraph 9, wherein the polynucleotide comprises a first strand consisting of the sequence of SEQ ID NO: 34, optionally further comprising a second strand consisting of the sequence of SEQ ID NO: 51.

26. A composition comprising the polynucleotide molecule of any one of paragraphs 1-25.

27. The composition of paragraph 26, wherein the composition further comprises an additive selected from the group consisting of insect feed, insect attractants, pheromones, proteins, carbohydrates, polymers, and pesticides.

28. A method for controlling Coleopteran infestation, the method comprising contacting a plant, ground, a Coleopteran insect, or a diet of a Coleopteran insect with the polynucleotide molecule of any one of paragraph 1-25, or the composition of paragraphs 26 or 27.

29. The method of paragraph 28, wherein the Coleopteran insect is of a species selected from the group consisting of: *Leptinotarsa* spp., *Phyllotreta* spp., *Cerotoma* spp., *Diabrotica* spp., *Tribolium* spp., *Anthonomus* spp. and *Alticini* spp.

30. The method of paragraph 28 or 29, wherein the Coleopteran insect is a *Leptinotarsa* spp. insect.

31. The method of paragraph 30, wherein the *Leptinotarsa* spp. insect is a Colorado potato beetle.

32. The method of any one of paragraph 28-31, wherein the plant is selected from the group consisting of Solanaceae plants, Brassicaceae plants, Poaceae plants, Cucurbitaceae plants, Fobaceae plants, Apiaceae plants, Amaranthaceae plants, and Malvaceae plants.

33. The method of any one of paragraph 28-32, wherein the method impairs growth, reproduction, and/or feeding of the Coleopteran insect.

34. The method of any one of paragraphs 28-32, wherein the method results in death of the Coleopteran insect.

35. A method for producing a polynucleotide for use in insect control, the method comprising:

(a) incubating in a reaction mixture cellular ribonucleic acid (RNA) and a ribonuclease and producing 5' nucleoside monophosphates (5' NMPs);

(b) eliminating the ribonuclease; and (c) incubating in the reaction mixture, or in a second reaction mixture, the 5' NMPs, a polyphosphate kinase, a polyphosphate, a polymerase, and a deoxyribonucleic acid (DNA) template having at least 80% identity to SEQ ID NO: 1, or encoding an RNA sequence that comprises a segment that comprises at least 18 contiguous nucleotides, wherein the segment has at least 90% identity to a segment of a sequence of SEQ ID NO: 18, and producing the RNA of interest, optionally wherein the reaction mixture of step (c) further comprises a nucleoside kinase, a NMP kinase, and/or a NDP kinase.

36. The method of paragraph 35, wherein the cellular RNA comprises ribosomal RNA, messenger RNA, and/or transfer RNA.

37. The method of paragraph 35 or 36, wherein the polyphosphate kinase is selected from PPK1 family enzymes and PPK2 family enzymes, and optionally wherein the polyphosphate kinase comprises a Class III polyphosphate kinase 2 from *Deinococcus geothermalis.*

38. The method of any one of paragraph 35-37, wherein the polyphosphate comprises hexametaphosphate.

39. The method according to paragraph 35, wherein the DNA template is a promotor operably linked to a nucleotide sequence encoding a desired PSMB5-targeting RNA, and optionally, a transcriptional terminator.

40. The method according to paragraph 39, wherein the DNA template further comprises a second template comprising a promoter operably linked to the reverse complement of the nucleotide sequence encoding a desired PSMB5-targeting RNA, wherein the two individual RNA molecules anneal to form a dsRNA molecule.

41. The method according to paragraph 35, wherein the DNA template is a promotor operably linked to a nucleotide sequence encoding: (a) a desired PSMB5 RNA, (b) one or more nucleotides of a loop region of an RNA transcript, (c) the reverse compliment of the nucleotide sequence encoding the desired PSMB5-targeting RNA and optionally, a transcriptional terminator.

42. The method according to paragraph 35 wherein the DNA template comprises:

a. a first promoter, b. a nucleotide sequence encoding a desired PSMB5-targeting RNA, c. a second promoter, and d. optionally, one or more transcriptional terminators, wherein the first and second promoters are operably linked to the nucleotide sequence encoding a desired PSMB5-targeting RNA and wherein the bidirectional transcription of the nucleotide sequence encoding the desired PSMB5-targeting RNA results in complementary RNA molecules which anneal to form the dsRNA molecule 43. The method of paragraph 35, wherein the ribonuclease, the polyphosphate kinase, the DNA template, and/or the polymerase is prepared from cells that express the ribonuclease, the polyphosphate kinase, the DNA template, and/or the polymerase.

44. The method of paragraph 35, wherein the reaction mixture of (a) comprises a cell lysate prepared from cells that express the ribonuclease, the polyphosphate kinase, the DNA template, and/or the polymerase.

45. The method of paragraph 35, wherein step (b) comprises eliminating the ribonuclease and native enzymatic activities in the cell lysate via temperature, pH, salt, detergent, alcohol, and/or chemical inhibitors.

46. The method of paragraph 35, wherein step (b) comprises eliminating native enzymatic activity of enzymes in the cell lysate via separation, precipitation, filtration, capture, and/or chromatography.

47. The method of paragraph 35, wherein step (b) comprises eliminating native enzymatic activity of enzymes in the cell lysate via genetic modification, enzyme secretion from a cell, and/or protease targeting.

48. The method of any one of paragraph 45-47, wherein the native enzymatic activities are selected from phosphatases, nucleases, proteases, deaminases, and hydrolases.

49. The method of any one of paragraph 45-48, wherein the polyphosphate kinase, and/or the polymerase can withstand elimination conditions.

50. The method of paragraph 35, wherein the polymerase comprises at least one RNA polymerase.

51. A double-stranded ribonucleic acid (dsRNA) comprising a sequence with at least 80% identity to the sequence of SEQ ID NO: 19.

52. The dsRNA of paragraph 51 comprising a sequence with at least 90% or at least 95% identity to the sequence of SEQ ID NO: 19.

53. The dsRNA of paragraph 51 comprising a sequence of SEQ ID NO: 19.

54. A composition comprising the dsRNA of any one of paragraph 51-53, optionally formulated at a concentration of 0.001 $\mu g/cm^2$ to 10 $\mu g/cm^2$.

55. The method of paragraph 28, wherein the contacting step comprises applying the polynucleotide to the surface of the plant, ground, Coleopteran insect, or diet of a Coleopteran insect at a concentration of at least 0.001 $\mu g/cm^2$.

56. The method of paragraph 55, wherein the contacting step comprises applying the polynucleotide to the surface of the plant, ground, Coleopteran insect, or diet of a Coleopteran insect at a concentration of 0.001 $\mu g/cm^2$ to 10 $\mu g/cm^2$.

57. The method of paragraph 56, wherein the contacting step comprises applying the polynucleotide to the surface of the plant, ground, Coleopteran insect, or diet of a Coleopteran insect at a concentration of 0.001 $\mu g/cm^2$ to 0.1 $\mu g/cm^2$.

58. The method of any one of paragraphs 55-57, wherein percent mortality of Coleopteran insects increase to at least 30% following fewer than 10, fewer than 9, fewer than 8, fewer than 7, fewer than 6, or fewer than 5 days of exposure of the Coleopteran insects to the polynucleotide, relative to a control, optionally under untreated conditions.

59. The method of paragraph 58, wherein percent mortality of Coleopteran insects increase to at least 40% following fewer than 10, fewer than 9, fewer than 8, fewer than 7, or fewer than 6 days of exposure of the Coleopteran insects to the polynucleotide, relative to a control, optionally under untreated conditions.

60. The method of paragraph 59, wherein percent mortality of Coleopteran insects increase to at least 50% following fewer than 10, fewer than 9, fewer than 8, or fewer than 7 days of exposure of the Coleopteran insects to the polynucleotide, relative to a control, optionally under untreated conditions.

61. The method of paragraph 60, wherein percent mortality of Coleopteran insects increase to at least 60% or at least 70% following fewer than 10, fewer than 9, or fewer than 8 days of exposure of the Coleopteran insects to the polynucleotide, relative to a control, optionally under untreated conditions.

62. The method of paragraph 60, wherein percent mortality of Coleopteran insects increase to at least 90% following fewer than 10 days or fewer than 9 days of exposure of the Coleopteran insects to the polynucleotide, relative to a control, optionally under untreated conditions.

63. The method of any one of paragraphs 55-62, wherein leaf disc consumption decrease to less than 20% following fewer than 10, fewer than 9, fewer than 8, fewer than 7, fewer than 6, or fewer than 5 days of exposure of Coleopteran insects to the polynucleotide, relative to a control, optionally under untreated conditions.

64. The method of paragraph 63, wherein leaf disc consumption decrease to less than 10% following fewer than 10% following fewer than 10, fewer than 9, fewer than 8, fewer than 7, fewer than 6, or fewer than 5 days of exposure of Coleopteran insects to the polynucleotide, relative to a control, optionally under untreated conditions.

65. The method of any one of paragraphs 55-64, wherein percent plant defoliation decreases to less than 10% following fewer than 10, fewer than 9, fewer than 8, fewer than 7, fewer than 6, fewer than 5, or fewer than 4 days of exposure of Coleopteran insects to the polynucleotide, relative to a control, optionally under untreated conditions.

66. The method of any one of paragraphs 55-65, wherein percent plant defoliation remains less than 10% following at least 10, at least 15, or at least 20 days following exposure of Coleopteran insects to the polynucleotide, relative to a control, optionally under untreated conditions.

TABLE 5

Sequences, 5'→3

| Description | Length (bp) | Sequence | SEQ ID NO: |
|---|---|---|---|
| DNA | | | |
| PSMB5 DNA | 1010 bp | GTCATTTGTCACTTTTGTCAGTTGTCGGTCAGTGAATTTTC<br>AATTTTGCTTGTAATCATCAGCGAATTAGAAGTTTTGAAT<br>AATTTTTTATAATACAGTACAAAAATGAGTTTAGCAGAG<br>ATCTGTGGAATGCAAGATTTAGATTCATTTAGGACGAACT<br>TCTGTCCCAACGAGTTGGATAGAATGTGCACCAATTTCGA<br>AAATAATCTGAATCTGGAAATGCCTCCTTTTGCAAATCCA<br>GCAGCAAAGGTATCACAATTAACGAGAGATGAAAGCGGT<br>CGAGAAATAAAAATGGCTTTTGATCATGGTACCACAACT<br>CTGGGTTTCATGTATAAAGGTGGTGTTGTTCTTGCTGTAG<br>ACTCCAGAGCTACAGGCGGACAATTTATTGGGTCGCAAA<br>CCATGAAAAAAATTGTGGAAATCAATGATTTCTTATTGGG<br>AACATTGGCTGGAGGTGCGGCAGACTGTGTTTATTGGGA<br>CCGTGTACTGGCCAAACAATGTAGAATGTATGAATTAAG<br>GAACAGGGAGCGTATTTCTGTAGCAGCTGCTTCCAAATTG<br>ATGGCAAACATGGTATACAATTACAAGGGAATGGGACTG<br>TCAATGGGAATGATGTTAGCAGGATGGGATAAAAGAGGT<br>CCACACCTGTACTATGTAGACTCCGAGGGTACCAGAACA<br>CCTGGAAAAGTCTTTAGTGTGGGTTCAGGTTCAATTTATG<br>CATTTGGTGTCTTGGATTCCGGATACAAATGGGATTTGAC<br>GGATGAGGAGGCTTACGATTTGGGTCGCAGGGCGATTTA<br>CCATGCCACACACAGAGATGCCTACTCTGGAGGTATCGT<br>GAGGGTTTATCACATGAAGGAGACTGGTTGGATACATAT<br>TGATAACAATGATTGTAATGATTTACATTATAAGTACCAG<br>GCTGAGAAGGAAGATTTGGAAAATACAATTGCTTAACTG<br>ACAGTTTCATTTCAATCAAGTTGAAGGTTCATTCGTATTT<br>CTTAATAAAAATAAGTTTTTAA | 1 |
| GS2 dsRNA target | 460 bp | AGGTGCGGCAGACTGTGTTTATTGGGACCGTGTACTGGCC<br>AAACAATGTAGAATGTATGAATTAAGGAACAGGGAGCGT<br>ATTTCTGTAGCAGCTGCTTCCAAATTGATGGCAAACATGG<br>TATACAATTACAAGGGAATGGGACTGTCAATGGGAATGA<br>TGTTAGCAGGATGGGATAAAAGAGTAAACTCCGAGGGTA<br>CCAGAACACCTGGAAAAGTCTTTAGTGTGGGTTCAGGTTC<br>AATTTATGCATTTGGTGTCTTGGATTCCGGATACAAATGG<br>GATTTGACGGATGAGGAGGCTTACGATTTGGGTCGCAGG<br>GCGATTTACCATGCCACACACAGAGATGCCTACTCTGGA<br>GGTATCGTGAGGGTTTATCACATGAAGGAGACTGGTTGG<br>ATACATATTGATAACAATGATTGTAATGATTTACATTATA<br>AGTACCAGGCTGAGAAGGAAGATTTG | 2 |
| GS4 (negative control - GFP) | 524 bp | ATGGTGAGCAAGGGCGAGGAGCTGTTCACCGGGGTGGTG<br>CCCATCCTGGTCGAGCTGGACGGCGACGTAAACGGCCAC<br>AAGTTCAGCGTGTCCGGCGAGGGCGAGGGCGATGCCACC<br>TACGGCAAGCTGACCCTGAAGTTCATCTGCACCACCGGC<br>AAGCTGCCCGTGCCCTGGCCCACCCTCGTGACCACCCTGA<br>CCTACGGCGTGCAGTGCTTCAGCCGCTACCCCGACCACAT<br>GAAGCAGCACGACTTCTTCAAGTCCGCCATGCCCGAAGG<br>CTACGTCCAGGAGCGCACCATCTTCTTCAAGGACGACGG<br>CAACTACAAGACCCGCGCCGAGGTGAAGTTCGAGGGCGA<br>CACCCTGGTGAACCGCATCGAGCTGAAGGGCATCGACTT<br>CAAGGAGGACGGCAACATCCTGGGGCACAAGCTGGAGTA | 3 |

TABLE 5 -continued

Sequences, 5'→3

| Description | Length (bp) | Sequence | SEQ ID NO: |
|---|---|---|---|
| | | CAACTACAACAGCCACAACGTCTATATCATGGCCGACAA GCAGAAGAACGGCATCAAGGTGAACTTCAAGATCCGCCA CAACATCGAGGACGG | |
| GS47 dsRNA target | 449 bp | GGTCATTTGTCACTTTTGTCAGTTGTCGGTCAGTGAA TTTTCAATTTTGCTTGTAATCATCAGCGAATTAGAAG TTTTGAATAATTTTTATAATACAGTACAAAAATGA GTTTAGCAGAGATCTGTGGAATGCAAGATTTAGATT CATTTAGGACGAACTTCTGTCCCAACGAGTTGGATA GAATGTGCACCAATTTCGAAAATAATCTGAATCTGG AAATGCCTCCTTTTGCAAATCCAGCAGCAAAGGTAT CACAATTAACGAGAGATGAAAGCGGTCGAGAAATA AAAATGGCTTTTGATCATGGTACCACAACTCTGGGT TTCATGTATAAAGGTGGTGTTGTTCTTGCTGTAGACT CCAGAGCTACAGGCGGACAATTTATTGGGTCGCAAA CCATGAAAAAAATTGTGGAAATCAATGATTTCTTAT TGGGAACATTGGCTGG | 4 |
| GS180 dsRNA target | 478 bp | AGGTGCGGCAGACTGTGTTTATTGGGACCGTGTACT GGCCAAACAATGTAGAATGTATGAATTAAGGAACA GGGAGCGTATTTCTGTAGCAGCTGCTTCCAAATTGA TGGCAAACATGGTATACAATTACAAGGGAATGGGA CTGTCAATGGGAATGATGTTAGCAGGATGGGATAA AAGAGGTCCACACCTGTACTATGTAGACTCCGAGGG TACCAGAACACCTGGAAAAGTCTTTAGTGTGGGTTC AGGTTCAATTTATGCATTTGGTGTCTTGGATTCCGGA TACAAATGGGATTTGACGGATGAGGAGGCTTACGAT TTGGGTCGCAGGGCGATTTACCATGCCACACACAGA GATGCCTACTCTGGAGGTATCGTGAGGGTTTATCAC ATGAAGGAGACTGGTTGGATACATATTGATAACAAT GATTGTAATGATTTACATTATAAGTACCAGGCTGAG AAGGAAGATTTG | 5 |
| GS181 dsRNA target | 561 bp | AGGTGCGGCAGACTGTGTTTATTGGGACCGTGTACT GGCCAAACAATGTAGAATGTATGAATTAAGGAACA GGGAGCGTATTTCTGTAGCAGCTGCTTCCAAATTGA TGGCAAACATGGTATACAATTACAAGGGAATGGGA CTGTCAATGGGAATGATGTTAGCAGGATGGGATAA AAGAGGTCCACACCTGTACTATGTAGACTCCGAGGG TACCAGAACACCTGGAAAAGTCTTTAGTGTGGGTTC AGGTTCAATTTATGCATTTGGTGTCTTGGATTCCGGA TACAAATGGGATTTGACGGATGAGGAGGCTTACGAT TTGGGTCGCAGGGCGATTTACCATGCCACACACAGA GATGCCTACTCTGGAGGTATCGTGAGGGTTTATCAC ATGAAGGAGACTGGTTGGATACATATTGATAACAAT GATTGTAATGATTTACATTATAAGTACCAGGCTGAG AAGGAAGATTTGGAAAATACAATTGCTTAACTGACA GTTTCATTTCAATCAAGTTGAAGGTTCATTCGTATTT CTTAATAAAAATAAGTTTTTAA | 6 |
| GS182 dsRNA target 70% identity to GS2 | 460 bp | ACGTCCCGCTGACTATTATTATAGGGACCGTAAGCT AGACTAACAATGCAGAATGTATGAGGTGAGGAACG GGGATTGTACTTTACCAGCAGCGGCTTGCCAGCGGA TGGTAACCGTGGGATACCATGCCACGTAAATAGGA ATATCGAGGGGAATGAGGTTAGCTGGATAGGCGAA AAGAGTACACCCCGAAGCTAGCAGAATCCCTGAAA AACACTGTATTCTGGTTTCCGGTTAAATCTTTGCTTT TGGTGTCTGGGATCCCAGATAAATATGGAATTTGTC AATCTAAGAAGCGAACCAATACGGCCTCGGGGCCTT CTACCGTGACGGCGACGGAGATGCCTACTCTTGCGG AGTCCTTCGCGCGTATCACATCAAGGACACGGATTG TATCCATATTGATAACAATTTTTGCATTGCTGAAACT TAAAAGTATTAGCCTGGGAAGTCCGATTTG | 7 |
| GS183 dsRNA target 75% identity to GS2 | 460 bp | CGGTTCGACAAACTGAGTTTGTTGGGAGCCTGGACT GGCCAAGCAATGTAGAATCTTTGATTTCAGGATGGG GGAGCGTATTTCCGTAGCAACGGCTTCCAAATTCAT GTCGTATATGGTTGAAACTTACAAGGAAATAAGACT GTCTGTGGGAATGATGTTAACAGGACCAGATGAAA GAGTTACATCGGACGGTATCAGAACAATTTCATAAA ACTTGCGTATAGGTTTAGGTAAACTCTATCCAGTTG ATGTCTTGGAGTCCTGATACAAAGGGTATTTGAAGG AAGCGGACGCTTACGATTTGCTTCGGAGGGCGATGT TCCATCCCACGCCTGGAGATGCCTACTCTCGAGGTC | 8 |

TABLE 5 -continued

| Sequences, 5'→3 | | | |
|---|---|---|---|
| Description | Length (bp) | Sequence | SEQ ID NO: |
| | | ACGTGAGGGTTCATCACATGAAGGGGTGGAGTTCG ATTGATATGAATGATAATTTTTGCAATCGTTTACATT ATAAGGTCCCTGCTGAGGAAGATGTCATA | |
| GS 184 dsRNA target 80% identity to GS2 | 460 bp | AGGTGGGTCCGACTGTCTTTATTGGGTACGTGTACT TGGGAGACCATGTATAATTAAGGAATTAAGGTCCAT GGTGCATATTTCTTGAGCACCTGCTTCATAAGTGAT GGGAATCATGGTATACCGTTCTAAGGGCACGAGACT GTCAAAGGGAATGATGTAAGCCGGATGGGATAAAA GAATAAGCTCCGAAGGTAACAGAACACATTGAAAA GGCTTTAGTGTGGGTAGAGCTTCAACTTATGAATTA AGAGTCATGGATTCCGGATACAAATGGGGTTTGACG GACGAAGAGCGTTACGACTTGGGTCCCTAGGCGCTT TACAAAGCCTCATACAGAGATACCTACTCCGGAGGG ATAAAAGTGGTTTATCAAATGATAGAGACAGGTAG GATTCATGTTGATAACAATGATTGTACTGAATTACT TTATAAGTACCAGGCCGAGGACTAATATTTG | 9 |
| GS 185 dsRNA target 85% identity to GS2 | 460 bp | AGGTGCGGGAGACTATGTGTCCTGGGAACGTGTACT GGCCAAACATCGTAGAATTTACGAAGTATCTAGCAG GGAGCGTAGTTCTGTAGCAGCTGCGTCCAAATTGAT GGCAAACATGGCATTCAATTTCTAAGGAATGGGACT GTTCATGGAAATGATGTTTGCATGATGGGATAAATG AGTAGACGCCGAGGCTACAAGAGCACCTGCAAAAG CATTTTGTGCGGGTTCAGCTTCCAGATATCCATTTCG TGTCTAGGATTCCGGACACAAATGGGATTTGACGGA TTAGGAGACTAACGATTTGGGTCGCAGGGCAATTTA CCATGCCACACGCAGAGATGCCTACTCTGTAGGTAT CGTGAGGATTTACGAGATGAAGTGGCCTGGTTGGAT ACATATTGATAACAATGATTGTAATAATTTACGGTT TAAGTACGAGGCTGAGAAGGGGGATATA | 10 |
| GS 186 dsRNA target 90% identity to GS2 | 460 bp | AGGTACGGCAGTCTGTGTTTATTGCGACCGTGTACT GGCCAAACGATGTAGGAAGTATGAGTTAAGGAACA GGGAGCATAGTTGTGTAGCAGCTGCTTCCAACATGA CGGCAAACATGGTATACCATTACAAGGGAATGGGA CTGTCAAAGGGAATAATGTTAGCAGGATGGCATGAT TGAGAAAACTCCGAGGGTACCAAAACACATGGAAA AGTCTTTAGTGTGGGTTCAGGTTCAATTTATGTATTT GGTGTCTTGGATTCCGGATACAAATGGGATTTGACG GATGAGGAGGCTTACGATTTGAGTCGTTGGGCGGTT TACCATCCCACACACAGAGATGCCTACTCTGGAGGT ATCGAGGGAGTTAACCACATGCAGGAGCCTGGGTG GATACAAATTGATAACAATGATTGGAATGATCTACA TTATAGGGTCCAGGCTGAGGGGGAAGTTTTG | 11 |
| GS187 dsRNA target 95% identity to GS2 | 460 bp | ATTTGCGGCAGGCTGTGTTTATTGGGACCGTGTACT GGCCAAACAATGTAGAATGTATGAATTAAGGAACA GGGAGCGTAGTTCTGTAGCAGCTGCTTCCAAATTGG TGGCAAACATGGTATACAATTACGAGGGAATGGGA CTGTCGATGGGAATGATGTAAGCAGGATGGGATGA AGGAGTAAACTCCGAGGGTACCAGAACACCTGGAA AAGTCTTTAGTGGGGGTTCAGGTTCGACTTATGCAT TTGATGTCTTGGATTCCGGATACAAATGGGATTTGA AGGATGAGGAGGCTTACGATTAGGGTCGCAGGGCG ATTTACCATGCCACACGCAGAGATGCCTACTCTGGA GGAATCTTGAGGGTTTATCACTTGAAGGAAACTGGT TGGATACATATTGATAACAATGATTGGAATGATTTA CATTATAAGTACCAGGCTGAGAAGGAAGATTTG | 12 |
| GS188 dsRNA target Nucleotides (nt) 80-280 of GS2 | 200 bp | ATTTCTGTAGCAGCTGCTTCCAAATTGATGGCAAAC ATGGTATACAATTACAAGGGAATGGGACTGTCAATG GGAATGATGTTAGCAGGATGGGATAAAAGAGTAAA CTCCGAGGGTACCAGAACACCTGGAAAAGTCTTTAG TGTGGGTTCAGGTTCAATTTATGCATTTGGTGTCTTG GATTCCGGATACAAATGGGA | 13 |
| GS189 dsRNA target nt 105-255 of GS2 | 150 bp | TGATGGCAAACATGGTATACAATTACAAGGGAATG GGACTGTCAATGGGAATGATGTTAGCAGGATGGGA TAAAAGAGTAAACTCCGAGGGTACCAGAACACCTG GAAAAGTCTTTAGTGTGGGTTCAGGTTCAATTTATG CATTTGGTG | 14 |

TABLE 5 -continued

| Description | Length (bp) | Sequence | SEQ ID NO: |
|---|---|---|---|
| Sequences, 5'→3 | | | |
| GS190 dsRNA target nt 130-230 of GS2 | 100 bp | CAAGGGAATGGACTGTCAATGGGAATGATGTTAG CAGGATGGGATAAAAGAGTAAACTCCGAGGGTACC AGAACACCTGGAAAAGTCTTTAGTGTGGGT | 15 |
| GS191 dsRNA target nt 155-205 of GS2 | 50 bp/ 74 bp* | ATGATGTTAGCAGGATGGGATAAAAGAGTAAACTC CGAGGGTACCAGAAC/ GGGAGAagatctATGATGTTAGCAGGATGGGATAAAAGAGT AAACTCCGAGGGTACCAGAACggtaccTCTCCC | 16 |
| GS192 dsRNA target nt 167-192 of GS2 | 25 bp/ 49 bp* | GGATGGGATAAAAGAGTAAACTCCG/ GGGAGAagatctGGATGGGATAAAAGAGTAAACTCCGggt accTCTCCC | 17 |
| RNA STRANDS | | | |
| PSMB5 mRNA | 1010 | GUCAUUUGUCACUUUUGUCAGUUGUCGGUCAGUGAAUU UUCAAUUUUGCUUGUAAUCAUCAGCGAAUUAGAAGUUU UGAAUAAUUUUUUAUAAUACAGUACAAAAAUGAGUUU AGCAGAGAUCUGUGGAAUGCAAGAUUUAGAUUCAUUUA GGACGAACUUCUGUCCCAACGAGUUGGAUAGAAUGUGC ACCAAUUUCGAAAAUAAUCUGAAUCUGGAAAUGCCUCC UUUUGCAAAUCCAGCAGCAAAGGUAUCACAAUUAACGA GAGAUGAAAGCGGUCGAGAAAUAAAAAUGGCUUUUGA UCAUGGUACCACAACUCUGGGUUUCAUGUAUAAAGGUG GUGUUGUUCUUGCUGUAGACUCCAGAGCUACAGGCGGA CAAUUUAUUGGGUCGCAAACCAUGAAAAAAAUUGUGGA AAUCAAUGAUUUCUUAUUGGGAACAUUGGCUGGAGGUG CGGCAGACUGUGUUUAUUGGGACCGUGUACUGGCCAAA CAAUGUAGAAUGUAUGAAUUAAGGAACAGGGAGCGUA UUUCUGUAGCAGCUGCUUCCAAAUUGAUGGCAAACAUG GUAUACAAUUACAAGGGAAUGGGACUGUCAAUGGGAAU GAUGUUAGCAGGAUGGGAUAAAAGAGGUCCACACCUGU ACUAUGUAGACUCCGAGGGUACCAGAACACCUGGAAAA GUCUUUAGUGUGGGUUCAGGUUCAAUUUAUGCAUUUGG UGUCUUGGAUUCCGGAUACAAAUGGGAUUUGACGGAUG AGGAGGCUUACGAUUUGGGUCGCAGGGCGAUUUACCAU GCCACACACAGAGAUGCCUACUCUGGAGGUAUCGUGAG GGUUUAUCACAUGAAGGAGACUGGUUGGAUACAUAUUG AUAACAAUGAUUGUAAUGAUUUACAUUAUAAGUACCAG GCUGAGAAGGAAGAUUUGGAAAAUACAAUUGCUUAACU GACAGUUUCAUUUCAAUCAAGUUGAAGGUUCAUUCGUA UUUCUUAAUAAAAAUAAGUUUUUAA | 18 |
| GS2 dsRNA strand | 460 bp | AGGUGCGGCAGACUGUGUUUAUUGGGACCGUGUACUGG CCAAACAAUGUAGAAUGUAUGAAUUAAGGAACAGGGAG CGUAUUUCUGUAGCAGCUGCUUCCAAAUUGAUGGCAAA CAUGGUAUACAAUUACAAGGGAAUGGGACUGUCAAUGG GAAUGAUGUUAGCAGGAUGGGAUAAAAGAGUAAACUCC GAGGGUACCAGAACACCUGGAAAAGUCUUUAGUGUGGG UUCAGGUUCAAUUUAUGCAUUUGGUGUCUUGGAUUCCG GAUACAAAUGGGAUUUGACGGAUGAGGAGGCUUACGAU UUGGGUCGCAGGGCGAUUUACCAUGCCACACACAGAGA UGCCUACUCUGGAGGUAUCGUGAGGGUUUAUCACAUGA AGGAGACUGGUUGGAUACAUAUUGAUAACAAUGAUUG UAAUGAUUUACAUUAUAAGUACCAGGCUGAGAAGGAAG AUUUG | 19 |
| GS4 (negative control) | 524 bp | AUGGUGAGCAAGGGCGAGGAGCUGUUCACCGGGGUGGU GCCCAUCCUGGUCGAGCUGGACGGCGACGUAAACGGCC ACAAGUUCAGCGUGUCCGGCGAGGGCGAGGGCGAUGCC ACCUACGGCAAGCUGACCCUGAAGUUCAUCUGCACCAC CGGCAAGCUGCCCGUGCCCUGGCCCACCCUCGUGACCAC CCUGACCUACGGCGUGCAGUGCUUCAGCCGCUACCCCG ACCACAUGAAGCAGCACGACUUCUUCAAGUCCGCCAUG CCCGAAGGCUACGUCCAGGAGCGCACCAUCUUCUUCAA GGACGACGGCAACUACAAGACCCGCGCCGAGGUGAAGU UCGAGGGCGACACCCUGGUGAACCGCAUCGAGCUGAAG GGCAUCGACUUCAAGGAGGACGGCAACAUCCUGGGGCA CAAGCUGGAGUACAACUACAACAGCCACAACGUCUAUA UCAUGGCCGACAAGCAGAAGAACGGCAUCAAGGUGAAC UUCAAGAUCCGCCACAACAUCGAGGACGG | 20 |

TABLE 5 -continued

| Description | Length (bp) | Sequence | SEQ ID NO: |
|---|---|---|---|
| | | Sequences, 5'→3 | |
| GS47 dsRNA strand | 449 bp | GGUCAUUUGUCACUUUUGUCAGUUGUCGGUCAGU GAAUUUUCAAUUUUGCUUGUAAUCAUCAGCGAAU UAGAAGUUUUGAAUAAUUUUUUAUAAUACAGUAC AAAAAUGAGUUUAGCAGAGAUCUGUGGAAUGCAA GAUUUAGAUUCAUUUAGGACGAACUUCUGUCCCA ACGAGUUGGAUAGAAUGUGCACCAAUUUCGAAAA UAAUCUGAAUCUGGAAAUGCCUCCUUUUGCAAAU CCAGCAGCAAAGGUAUCACAAUUAACGAGAGAUG AAAGCGGUCGAGAAAUAAAAAUGGCUUUUGAUCA UGGUACCACAACUCUGGGUUUCAUGUAUAAAGGU GGUGUUGUUCUUGCUGUAGACUCCAGAGCUACAG GCGGACAAUUUAUUGGGUCGCAAACCAUGAAAAA AAUUGUGGAAAUCAAUGAUUUCUUAUUGGGAACA UUGGCUGG | 21 |
| GS180 dsRNA strand | 478 bp | AGGUGCGGCAGACUGUGUUUAUUGGGACCGUGUA CUGGCCAAACAAUGUAGAAUGUAUGAAUUAAGGA ACAGGGAGCGUAUUUCUGUAGCAGCUGCUUCCAA AUUGAUGGCAAACAUGGUAUACAAUUACAAGGGA AUGGGACUGUCAAUGGGAAUGAUGUUAGCAGGAU GGGAUAAAAGAGGUCCACACCUGUACUAUGUAGA CUCCGAGGGUACCAGAACACCUGGAAAAGUCUUUA GUGUGGGUUCAGGUUCAAUUUAUGCAUUUGGUGU CUUGGAUUCCGGAUACAAAUGGGAUUUGACGGAU GAGGAGGCUUACGAUUUGGGUCGCAGGGCGAUUU ACCAUGCCACACACAGAGAUGCCUACUCUGGAGGU AUCGUGAGGGUUUAUCACAUGAAGGAGACUGGUU GGAUACAUAUUGAUAACAAUGAUUGUAAUGAUUU ACAUUAUAAGUACCAGGCUGAGAAGGAAGAUUUG | 22 |
| GS181 dsRNA strand | 561 bp | AGGUGCGGCAGACUGUGUUUAUUGGGACCGUGUA CUGGCCAAACAAUGUAGAAUGUAUGAAUUAAGGA ACAGGGAGCGUAUUUCUGUAGCAGCUGCUUCCAA AUUGAUGGCAAACAUGGUAUACAAUUACAAGGGA AUGGGACUGUCAAUGGGAAUGAUGUUAGCAGGAU GGGAUAAAAGAGGUCCACACCUGUACUAUGUAGA CUCCGAGGGUACCAGAACACCUGGAAAAGUCUUUA GUGUGGGUUCAGGUUCAAUUUAUGCAUUUGGUGU CUUGGAUUCCGGAUACAAAUGGGAUUUGACGGAU GAGGAGGCUUACGAUUUGGGUCGCAGGGCGAUUU ACCAUGCCACACACAGAGAUGCCUACUCUGGAGGU AUCGUGAGGGUUUAUCACAUGAAGGAGACUGGUU GGAUACAUAUUGAUAACAAUGAUUGUAAUGAUUU ACAUUAUAAGUACCAGGCUGAGAAGGAAGAUUUG GAAAAUACAAUUGCUUAACUGACAGUUUCAUUUC AAUCAAGUUGAAGGUUCAUUCGUAUUUCUUAAUA AAAAUAAGUUUUUAA | 23 |
| GS182 dsRNA strand 70% identity to GS2 | 460 bp | ACGUCCCGCUGACUAUUAUUAUAGGGACCGUAAGC UAGACUAACAAUGCAGAAUGUAUGAGGUGAGGAA CGGGGAUUGUACUUUACCAGCAGCGGCUUGCCAGC GGAUGGUAACCGUGGGAUACCAUGCCACGUAAAU AGGAAUAUCGAGGGGAAUGAGGUUAGCUGGAUAG GCGAAAAGAGUACACCCCGAAGCUAGCAGAAUCCC UGAAAAACACUGUAUUCUGGUUUCCGGUUAAAUC UUUGCUUUUGGUGUCUGGGAUCCCAGAUAAAUAU GGAAUUUGUCAAUCUAAGAAGCGAACCAAUACGG CCUCGGGGCCUUCUACCGUGACGGCGACGGAGAUG CCUACUCUUGCGGAGUCCUUCGCGCGUAUCACAUC AAGGACACGGAUUGUAUCCAUAUUGAUAACAAUU UUUGCAUUGCUGAAACUUAAAAGUAUUAGCCUGG GAAGUCCGAUUUG | 24 |
| GS183 dsRNA strand 75% identity to GS2 | 460 bp | CGGUUCGACAAACUGAGUUUGUUGGGAGCCUGGA CUGGCCAAGCAAUGUAGAAUCUUUGAUUUCAGGA UGGGGGAGCGUAUUUCCGUAGCAACGGCUUCCAA AUUCAUGUCGUAUAUGGUUGAAACUUACAAGGAA AUAAGACUGUCUGUGGGAAUGAUGUUAACAGGAC CAGAUGAAAGAGUUACAUCGGACGGUAUCAGAAC AAUUUCAUAAAACUUGCGUAUAGGUUUAGGUAAA CUCUAUCCAGUUGAUGUCUUGGAGUCCUGAUACA AAGGGUAUUUGAAGGAAGCGGACGCUUACGAUUU GCUUCGGAGGGCGAUGUUCCAUCCCACGCCUGGAG AUGCCUACUCUCGAGGUCACGUGAGGGUUCAUCAC | 25 |

TABLE 5 -continued

| Description | Length (bp) | Sequence | SEQ ID NO: |
|---|---|---|---|
| Sequences, 5'→3 | | | |
| | | AUGAAGGGGUGGAGUUCGAUUGAUAUGAAUGAUA<br>AUUUUUGCAAUCGUUUACAUUAUAAGGUCCCUGC<br>UGAGGAAGAUGUCAUA | |
| GS184 dsRNA strand 80% identity to GS2 | 460 bp | AGGUGGGUCCGACUGUCUUUAUUGGGUACGUGUA<br>CUUGGGAGACCAUGUAUAAUUAAGGAAUUAAGGU<br>CCAUGGUGCAUAUUUCUUGAGCACCUGCUUCAUAA<br>GUGAUGGGAAUCAUGGUAUACCGUUCUAAGGGCA<br>CGAGACUGUCAAAGGGAAUGAUGUAAGCCGGAUG<br>GGAUAAAAGAAUAAGCUCCGAAGGUAACAGAACA<br>CAUUGAAAAGGCUUUAGUGUGGGUAGAGCUUCAA<br>CUUAUGAAUUAAGAGUCAUGGAUUCCGGAUACAA<br>AUGGGGUUUGACGGACGAAGAGCGUUACGACUUG<br>GGUCCCUAGGCGCUUUACAAAGCCUCAUACAGAGA<br>UACCUACUCCGGAGGGAUAAAAGUGGUUUAUCAA<br>AUGAUAGAGACAGGUAGGAUUCAUGUUGAUAACA<br>AUGAUUGUACUGAAUUACUUUAUAAGUACCAGGC<br>CGAGGACUAAUAUUUG | 26 |
| GS185 dsRNA strand 85% identity to GS2 | 460 bp | AGGUGCGGGAGACUAUGUGUCCUGGGAACGUGUA<br>CUGGCCAAACAUCGUAGAAUUUACGAAGUAUCUA<br>GCAGGGAGCGUAGUUCUGUAGCAGCUGCGUCCAA<br>AUUGAUGGCAAACAUGGCAUUCAAUUUCUAAGGA<br>AUGGGACUGUUCAUGGAAAUGAUGUUUGCAUGAU<br>GGGAUAAAUGAGUAGACGCCGAGGCUACAAGAGC<br>ACCUGCAAAAGCAUUUUGUGCGGGUUCAGCUUCCA<br>GAUAUCCAUUUCGUGUCUAGGAUUCCGGACACAA<br>AUGGGAUUUGACGGAUUAGGAGACUAACGAUUUG<br>GGUCGCAGGGCAAUUUACCAUGCCACACGCAGAGA<br>UGCCUACUCUGUAGGUAUCGUGAGGAUUUACGAG<br>AUGAAGUGGCCUGGUUGGAUACAUAUUGAUAACA<br>AUGAUUGUAAUAAUUUACGGUUUAAGUACGAGGC<br>UGAGAAGGGGGAUAUA | 27 |
| GS186 dsRNA strand 90% identity to GS2 | 460 bp | AGGUACGGCAGUCUGUGUUUAUUGCGACCGUGUA<br>CUGGCCAAACGAUGUAGGAAGUAUGAGUUAAGGA<br>ACAGGGAGCAUAGUUGUGUAGCAGCUGCUUCCAA<br>CAUGACGGCAAACAUGGUAUACCAUUACAAGGGA<br>AUGGGACUGUCAAAGGGAAUAAUGUUAGCAGGAU<br>GGCAUGAUUGAGAAAACUCCGAGGGUACCAAAAC<br>ACAUGGAAAAGUCUUUAGUGUGGGUUCAGGUUCA<br>AUUUAUGUAUUUGGUGUCUUGGAUUCCGGAUACA<br>AAUGGGAUUUGACGGAUGAGGAGGCUUACGAUUU<br>GAGUCGUUGGGCGGUUUACCAUCCCACACACAGAG<br>AUGCCUACUCUGGAGGUAUCGAGGGAGUUAACCA<br>CAUGCAGGAGCCUGGGUGGAUACAAAUUGAUAAC<br>AAUGAUUGGAAUGAUCUACAUUAUAGGGUCCAGG<br>CUGAGGGGGAAGUUUUG | 28 |
| GS187 dsRNA strand 95% identity to GS2 | 460 bp | AUUUGCGGCAGGCUGUGUUUAUUGGGACCGUGUA<br>CUGGCCAAACAAUGUAGAAUGUAUGAAUUAAGGA<br>ACAGGGAGCGUAGUUCUGUAGCAGCUGCUUCCAA<br>AUUGGUGGCAAACAUGGUAUACAAUUACGAGGGA<br>AUGGGACUGUCGAUGGGAAUGAUGUAAGCAGGAU<br>GGGAUGAAGGAGUAAACUCCGAGGGUACCAGAAC<br>ACCUGGAAAAGUCUUUAGUGGGGGUUCAGGUUCG<br>ACUUAUGCAUUUGAUGUCUUGGAUUCCGGAUACA<br>AAUGGGAUUUGAAGGAUGAGGAGGCUUACGAUUA<br>GGGUCGCAGGGCGAUUUACCAUGCCACACGCAGAG<br>AUGCCUACUCUGGAGGAAUCUUGAGGGUUUAUCA<br>CUUGAAGGAAACUGGUUGGAUACAUAUUGAUAAC<br>AAUGAUUGGAAUGAUUUACAUUAUAAGUACCAGG<br>CUGAGAAGGAAGAUUUG | 29 |
| GS188 dsRNA strand Nucleotides (nt) 80-280 of GS2 | 200 bp | AUUUCUGUAGCAGCUGCUUCCAAAUUGAUGGCAA<br>ACAUGGUAUACAAUUACAAGGGAAUGGGACUGUC<br>AAUGGGAAUGAUGUUAGCAGGAUGGGAUAAAAGA<br>GUAAACUCCGAGGGUACCAGAACACCUGGAAAAG<br>UCUUUAGUGUGGGUUCAGGUUCAAUUUAUGCAUU<br>UGGUGUCUUGGAUUCCGGAUACAAAUGGGA | 30 |

TABLE 5 -continued

| Description | Length (bp) | Sequence | SEQ ID NO: |
|---|---|---|---|
| Sequences, 5'→3 | | | |
| GS189 dsRNA strand nt 105-255 of GS2 | 150 bp | UGAUGGCAAACAUGGUAUACAAUUACAAGGGAAU GGGACUGUCAAUGGGAAUGAUGUUAGCAGGAUGG GAUAAAAGAGUAAACUCCGAGGGUACCAGAACAC CUGGAAAAGUCUUUAGUGUGGGUUCAGGUUCAAU UUAUGCAUUUGGUG | 31 |
| GS190 dsRNA strand nt 130-230 of GS2 | 100 bp | CAAGGGAAUGGGACUGUCAAUGGGAAUGAUGUUA GCAGGAUGGGAUAAAAGAGUAAACUCCGAGGGUA CCAGAACACCUGGAAAAGUCUUUAGUGUGGGU | 32 |
| GS191 dsRNA strand nt 155-205 of GS2 | 50 bp | AUGAUGUUAGCAGGAUGGGAUAAAAGAGUAAACU CCGAGGGUACCAGAAC | 33 |
| GS192 dsRNA strand nt 167-192 of GS2 | 25 bp | GGAUGGGAUAAAAGAGUAAACUCCG | 34 |
| REVERS COMPLEMENT RNA STRANDS | | | |
| PSMB5 mRNA reverse complement | 1010 bp | UUAAAAACUUAUUUUUAUUAAGAAAUACGAAUGAACCU UCAACUUGAUUGAAAUGAAACUGUCAGUUAAGCAAUUG UAUUUUCCAAAUCUUCCUUCUCAGCCUGGUACUUAUAA UGUAAAUCAUUACAAUCAUUGUUAUCAAUAUGUAUCCA ACCAGUCUCCUUCAUGUGAUAAACCCUCACGAUACCUC CAGAGUAGGCAUCUCUGUGUGUGGCAUGGUAAAUCGCC CUGCGACCCAAAUCGUAAGCCUCCUCAUCCGUCAAAUC CCAUUUGUAUCCGGAAUCCAAGACACCAAAUGCAUAAA UUGAACCUGAACCCACACUAAAGACUUUUCCAGGUGUU CUGGUACCCUCGGAGUCUACAUAGUACAGGUGUGGACC UCUUUUAUCCCAUCCUGCUAACAUCAUUCCCAUUGACA GUCCCAUUCCCUUGUAAUUGUAUACCAUGUUUGCCAUC AAUUUGGAAGCAGCUGCUACAGAAAUACGCUCCCUGUU CCUUAAUUCAUACAUUCUACAUUGUUUGGCCAGUACAC GGUCCCAAUAAACACAGUCUGCCGCACCUCCAGCCAAU GUUCCCAAUAAGAAAUCAUUGAUUUCCACAAUUUUUUU CAUGGUUUGCGACCCAAUAAAUUGUCCGCCUGUAGCUC UGGAGUCUACAGCAAGAACAACACCACCUUUAUACAUG AAACCCAGAGUUGUGGUACCAUGAUCAAAAGCCAUUUU UAUUUCUCGACCGCUUUCAUCUCUCGUUAAUUGUGAUA CCUUUGCUGCUGGAUUUGCAAAAGGAGGCAUUUCCAGA UUCAGAUUAUUUUCGAAAUUGGUGCACAUUCUAUCCAA CUCGUUGGGACAGAAGUUCGUCCUAAAUGAAUCUAAAU CUUGCAUUCCACAGAUCUCUGCUAAACUCAUUUUUGUA CUGUAUUAUAAAAAAUUAUUCAAAACUUCUAAUUCGCU GAUGAUUACAAGCAAAAUUGAAAAUUCACUGACCGACA ACUGACAAAAGUGACAAAUGAC | 35 |
| GS2 reverse complement | 460 bp | CAAAUCUUCCUUCUCAGCCUGGUACUUAUAAUGUAAAU CAUUACAAUCAUUGUUAUCAAUAUGUAUCCAACCAGUC UCCUUCAUGUGAUAAACCCUCACGAUACCUCCAGAGUA GGCAUCUCUGUGUGUGGCAUGGUAAAUCGCCCUGCGAC CCAAAUCGUAAGCCUCCUCAUCCGUCAAAUCCCAUUUG UAUCCGGAAUCCAAGACACCAAAUGCAUAAAUUGAACC UGAACCCACACUAAAGACUUUUCCAGGUGUUCUGGUAC CCUCGGAGUUUACUCUUUUAUCCCAUCCUGCUAACAUC AUUCCCAUUGACAGUCCCAUUCCCUUGUAAUUGUAUAC CAUGUUUGCCAUCAAUUUGGAAGCAGCUGCUACAGAAA UACGCUCCCUGUUCCUUAAUUCAUACAUUCUACAUUGU UUGGCCAGUACACGGUCCCAAUAAACACAGUCUGCCGC ACCU | 36 |
| GS4 (negative control) reverse complement | 524 bp | CCGUCCUCGAUGUUGUGGCGGAUCUUGAAGUUCACCUU GAUGCCGUUCUUCUGCUUGUCGGCCAUGAUAUAGACGU UGUGGCUGUUGUAGUUGUACUCCAGCUUGUGCCCCAGG AUGUUGCCGUCCUCCUUGAAGUCGAUGCCCUUCAGCUC GAUGCGGUUCACCAGGGUGUCGCCCUCGAACUUCACCU CGGCGCGGGUCUUGUAGUUGCCGUCGUCCUUGAAGAAG AUGGUGCGCUCCUGGACGUAGCCUUCGGGCAUGGCGGA CUUGAAGAAGUCGUGCUGCUUCAUGUGGUCGGGGUAGC GGCUGAAGCACUGCACGCCGUAGGUCAGGGUGGUCACG | 37 |

TABLE 5 -continued

| Sequences, 5'→3 | | | |
|---|---|---|---|
| Description | Length (bp) | Sequence | SEQ ID NO: |
| | | AGGGUGGGCCAGGGCACGGGCAGCUUGCCGGUGGUGCA GAUGAACUUCAGGGUCAGCUUGCCGUAGGUGGCAUCGC CCUCGCCCUCGCCGGACACGCUGAACUUGUGGCCGUUU ACGUCGCCGUCCAGCUCGACCAGGAUGGGCACCACCCCG GUGAACAGCUCCUCGCCCUUGCUCACCAU | |
| GS47 dsRNA target | 4449 bp | CCAGCCAAUGUUCCCAAUAAGAAAUCAUUGAUUUCCAC AAUUUUUUUCAUGGUUUGCGACCCAAUAAAUUGUCCGC CUGUAGCUCUGGAGUCUACAGCAAGAACAACACCACCU UUAUACAUGAAACCCAGAGUUGUGGUACCAUGAUCAAA AGCCAUUUUUAUUUCUCGACCGCUUUCAUCUCUCGUUA AUUGUGAUACCUUUGCUGCUGGAUUUGCAAAAGGAGGC AUUUCCAGAUUCAGAUUAUUUUCGAAAUUGGUGCACAU UCUAUCCAACUCGUUGGGACAGAAGUUCGUCCUAAAUG AAUCUAAAUCUUGCAUUCCACAGAUCUCUGCUAAACUC AUUUUUGUACUGUAUUAUAAAAAAUUAUUCAAAACUUC UAAUUCGCUGAUGAUUACAAGCAAAAUUGAAAAUUCAC UGACCGACAACUGACAAAAGUGACAAAUGACC | 38 |
| GS180 dsRNA target | 478 bp | CAAAUCUUCCUUCUCAGCCUGGUACUUAUAAUGUAAAU CAUUACAAUCAUUGUUAUCAAUAUGUAUCCAACCAGUC UCCUUCAUGUGAUAAACCCUCACGAUACCUCCAGAGUA GGCAUCUCUGUGUGUGGCAUGGUAAAUCGCCCUGCGAC CCAAAUCGUAAGCCUCCUCAUCCGUCAAAUCCCAUUUG UAUCCGGAAUCCAAGACACCAAAUGCAUAAAUUGAACC UGAACCCACACUAAAGACUUUUCCAGGUGUUCUGGUAC CCUCGGAGUCUACAUAGUACAGGUGUGGACCUCUUUUA UCCCAUCCUGCUAACAUCAUUCCCAUUGACAGUCCCAU UCCCUUGUAAUUGUAUACCAUGUUUGCCAUCAAUUUGG AAGCAGCUGCUACAGAAAUACGCUCCCUGUUCCUUAAU UCAUACAUUCUACAUUGUUUGGCCAGUACACGGUCCCA AUAAACACAGUCUGCCGCACCU | 39 |
| GS181 dsRNA target | 561 bp | UUAAAAACUUAUUUUUAUUAAGAAAUACGAAUGAACCU UCAACUUGAUUGAAAUGAAACUGUCAGUUAAGCAAUUG UAUUUUCCAAAUCUUCCUUCUCAGCCUGGUACUUAUAA UGUAAAUCAUUACAAUCAUUGUUAUCAAUAUGUAUCCA ACCAGUCUCCUUCAUGUGAUAAACCCUCACGAUACCUC CAGAGUAGGCAUCUCUGUGUGUGGCAUGGUAAAUCGCC CUGCGACCCAAAUCGUAAGCCUCCUCAUCCGUCAAAUC CCAUUUGUAUCCGGAAUCCAAGACACCAAAUGCAUAAA UUGAACCUGAACCCACACUAAAGACUUUUCCAGGUGUU CUGGUACCCUCGGAGUCUACAUAGUACAGGUGUGGACC UCUUUUAUCCCAUCCUGCUAACAUCAUUCCCAUUGACA GUCCCAUUCCCUUGUAAUUGUAUACCAUGUUUGCCAUC AAUUUGGAAGCAGCUGCUACAGAAAUACGCUCCCUGUU CCUUAAUUCAUACAUUCUACAUUGUUUGGCCAGUACAC GGUCCCAAUAAACACAGUCUGCCGCACCU | 40 |
| GS182 reverse complement 70% identity to GS2 | 460 bp | CAAAUCGGACUUCCCAGGCUAAUACUUUUAAGUUUCAG CAAUGCAAAAAUUGUUAUCAAUAUGGAUACAAUCCGUG UCCUUGAUGUGAUACGCGCGAAGGACUCCGCAAGAGUA GGCAUCUCCGUCGCCGUCACGGUAGAAGGCCCCGAGGC CGUAUUGGUUCGCUUCUUAGAUUGACAAAUUCCAUAUU UAUCUGGGAUCCCAGACACCAAAAGCAAAGAUUUAACC GGAAACCAGAAUACAGUGUUUUUCAGGGAUUCUGCUAG CUUCGGGGUGUACUCUUUUCGCCUAUCCAGCUAACCUC AUUCCCCUCGAUAUUCCUAUUUACGUGGCAUGGUAUCC CACGGUUACCAUCCGCUGGCAAGCCGCUGCUGGUAAAG UACAAUCCCCGUUCCUCACCUCAUACAUUCUGCAUUGU UAGUCUAGCUUACGGUCCCUAUAAUAAUAGUCAGCGGG ACGU | 41 |
| GS183 reverse complement 75% identity to GS2 | 460 bp | UAUGACAUCUUCCUCAGCAGGGACCUUAUAAUGUAAAC GAUUGCAAAAAUUAUCAUUCAUAUCAAUCGAACUCCAC CCCUUCAUGUGAUGAACCCUCACGUGACCUCGAGAGUA GGCAUCUCCAGGCGUGGGAUGGAACAUCGCCCUCCGAA GCAAAUCGUAAGCGUCCGCUUCCUUCAAAUACCCUUUG UAUCAGGACUCCAAGACAUCAACUGGAUAGAGUUUACC UAAACCUAUACGCAAGUUUUAUGAAAUUGUUCUGAUAC CGUCCGAUGUAACUCUUUCAUCUGGUCCUGUUAACAUC AUUCCCACAGACAGUCUUAUUUCCUUGUAAGUUUCAAC CAUAUACGACAUGAAUUUGGAAGCCGUUGCUACGGAAA UACGCUCCCCCAUCCUGAAAUCAAAGAUUCUACAUUGC | 42 |

TABLE 5 -continued

| Description | Length (bp) | Sequence | SEQ ID NO: |
|---|---|---|---|
| | | UUGGCCAGUCCAGGCUCCCAACAAACUCAGUUUGUCGA ACCG | |
| GS184 reverse complement 80% identity to GS2 | 460 bp | CAAAUAUUAGUCCUCGGCCUGGUACUUAUAAAGUAAUU CAGUACAAUCAUUGUUAUCAACAUGAAUCCUACCUGUC UCUAUCAUUUGAUAAACCACUUUUAUCCCUCCGGAGUA GGUAUCUCUGUAUGAGGCUUUGUAAAGCGCCUAGGGAC CCAAGUCGUAACGCUCUUCGUCCGUCAAACCCCAUUUG UAUCCGGAAUCCAUGACUCUUAAUUCAUAAGUUGAAGC UCUACCCACACUAAAGCCUUUUCAAUGUGUUCUGUUAC CUUCGGAGCUUAUUCUUUUAUCCCAUCCGGCUUACAUC AUUCCCUUUGACAGUCUCGUGCCCUUAGAACGGUAUAC CAUGAUUCCCAUCACUUAUGAAGCAGGUGCUCAAGAAA UAUGCACCAUGGACCUUAAUUCCUUAAUUAUACAUGGU CUCCCAAGUACACGUACCCAAUAAAGACAGUCGGACCC ACCU | 43 |
| GS185 reverse complement 85% identity to GS2 | 460 bp | UAUAUCCCCCUUCUCAGCCUCGUACUUAAACCGUAAAU UAUUACAAUCAUUGUUAUCAAUAUGUAUCCAACCAGGC CACUUCAUCUCGUAAAUCCUCACGAUACCUACAGAGUA GGCAUCUCUGCGUGUGGCAUGGUAAAUUGCCCUGCGAC CCAAAUCGUUAGUCUCCUAAUCCGUCAAAUCCCAUUUG UGUCCGGAAUCCUAGACACGAAAUGGAUAUCUGGAAGC UGAACCCGCACAAAAUGCUUUUGCAGGUGCUCUUGUAG CCUCGGCGUCUACUCAUUUAUCCCAUCAUGCAAACAUC AUUUCCAUGAACAGUCCCAUUCCUUAGAAAUUGAAUGC CAUGUUUGCCAUCAAUUUGGACGCAGCUGCUACAGAAC UACGCUCCCUGCUAGAUACUUCGUAAAUUCUACGAUGU UUGGCCAGUACACGUUCCCAGGACACAUAGUCUCCCGC ACCU | 44 |
| GS186 reverse complement 90% identity to GS2 | 460 bp | CAAAACUUCCCCCUCAGCCUGGACCCUAUAAUGUAGAU CAUUCCAAUCAUUGUUAUCAAUUUGUAUCCACCCAGGC UCCUGCAUGUGGUUAACUCCCUCGAUACCUCCAGAGUA GGCAUCUCUGUGUGUGGGAUGGUAAACCGCCCAACGAC UCAAAUCGUAAGCCUCCUCAUCCGUCAAAUCCCAUUUG UAUCCGGAAUCCAAGACACCAAAUACAUAAAUUGAACC UGAACCCACACUAAAGACUUUUCCAUGUGUUUUGGUAC CCUCGGAGUUUUCUCAAUCAUGCCAUCCUGCUAACAUU AUUCCCUUUGACAGUCCCAUUCCCUUGUAAUGGUAUAC CAUGUUUGCCGUCAUGUUGGAAGCAGCUGCUACACAAC UAUGCUCCCUGUUCCUUAACUCAUACUUCCUACAUCGU UUGGCCAGUACACGGUCGCAAUAAACACAGACUGCCGU ACCU | 45 |
| GS187 reverse complement 95% identity to GS2 | 460 bp | CAAAUCUUCCUUCUCAGCCUGGUACUUAUAAUGUAAAU CAUUCCAAUCAUUGUUAUCAAUAUGUAUCCAACCAGUU UCCUUCAAGUGAUAAACCCUCAAGAUUCCUCCAGAGUA GGCAUCUCUGCGUGUGGCAUGGUAAAUCGCCCUGCGAC CCUAAUCGUAAGCCUCCUCAUCCUUCAAAUCCCAUUUG UAUCCGGAAUCCAAGACAUCAAAUGCAUAAGUCGAACC UGAACCCCCACUAAAGACUUUUCCAGGUGUUCUGGUAC CCUCGGAGUUUACUCCUUCAUCCCAUCCUGCUUACAUC AUUCCCAUCGACAGUCCCAUUCCCUCGUAAUUGUAUAC CAUGUUUGCCACCAAUUUGGAAGCAGCUGCUACAGAAC UACGCUCCCUGUUCCUUAAUUCAUACAUUCUACAUUGU UUGGCCAGUACACGGUCCCAAUAAACACAGCCUGCCGC AAAU | 46 |
| GS188 reverse complement Nucleotides (nt) 80-280 of GS2 | 200 bp | UCCCAUUUGUAUCCGGAAUCCAAGACACCAAAUGCAUA AAUUGAACCUGAACCCACACUAAAGACUUUUCCAGGUG UUCUGGUACCCUCGGAGUUUACUCUUUUAUCCCAUCCU GCUAACAUCAUUCCCAUUGACAGUCCCAUUCCCUUGUA AUUGUAUACCAUGUUUGCCAUCAAUUUGGAAGCAGCUG CUACAGAAAU | 47 |
| GS189 reverse complement nt 105-255 of GS2 | 150 bp | CACCAAAUGCAUAAAUUGAACCUGAACCCACACUAAAG ACUUUUCCAGGUGUUCUGGUACCCUCGGAGUUUACUCU UUUAUCCCAUCCUGCUAACAUCAUUCCCAUUGACAGUC CCAUUCCCUUGUAAUUGUAUACCAUGUUUGCCAUCA | 48 |

TABLE 5 -continued

| Sequences, 5'→3 | | | |
|---|---|---|---|
| Description | Length (bp) | Sequence | SEQ ID NO: |
| GS190 reverse complement nt 130-230 of GS2 | 100 bp | ACCCACACUAAAGACUUUUCCAGGUGUUCUGGUACCCU CGGAGUUUACUCUUUUAUCCCAUCCUGCUAACAUCAUU CCCAUUGACAGUCCCAUUCCCUUG | 49 |
| GS191 reverse complement nt 155-205 of GS2 | 50 bp | GUUCUGGUACCCUCGGAGUUUACUCUUUUAUCCCAUCC UGCUAACAUCAU | 50 |
| GS192 reverse complement nt 167-192 of GS2 | 25 bp | CGGAGUUUACUCUUUUAUCCCAUCC | 51 |

*Both sequences are 24 bp longer than the actual target sequences due to part of the T7 promoter and a restriction site.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A double-stranded RNA (dsRNA) that inhibits expression of the *Leptinotarsa decemlineata* proteasome beta 5 (PSMB5) gene, wherein a first strand of the dsRNA comprises an RNA sequence that is at least 100 nucleotides in length and is 85% to 100% complementary to the RNA encoded by SEQ ID NO: 2.

2. The dsRNA of claim 1, wherein a second strand of the dsRNA is complementary to the first strand.

3. The dsRNA of claim 1, wherein the RNA sequence comprises the RNA sequence of SEQ ID NO: 19.

4. The dsRNA of claim 1, wherein the first strand of the dsRNA comprises an RNA sequence 95% to 100% complementary to the RNA encoded by SEQ ID NO: 2.

5. The dsRNA of claim 1, wherein the RNA sequence has a length of 100 to 460 nucleotides.

6. The dsRNA of claim 1, wherein the first strand of the dsRNA comprises 18 to 21 contiguous nucleotides 90% to 100% complementary to the RNA encoded by SEQ ID NO: 2.

7. The dsRNA of claim 1, wherein the first strand comprises an RNA sequence that has 85% to 100% identity to the RNA sequence of SEQ ID NO: 36.

8. The dsRNA of claim 7, wherein the first strand comprises at least 18 to 21 contiguous nucleotides that have at least 90% to 100% identity to the RNA sequence of SEQ ID NO: 36.

9. A composition comprising the dsRNA of claim 1.

10. The composition of claim 9, wherein the composition further comprises at least one additive selected from the group consisting of: adjuvants, attractants, growth-regulating substances, insect feed, pheromones, proteins, carbohydrates, polymers, organic compounds, biologics, and pesticidal agents.

11. A deoxyribonucleic acid (DNA) encoding the RNA of claim 1.

12. A method for controlling Coleopteran insect infestation, the method comprising delivering to a plant, ground, a Coleopteran insect, or a diet of a Coleopteran insect the dsRNA of claim 1.

13. A method for controlling Coleopteran insect infestation, the method comprising delivering to a plant, ground, a Coleopteran insect, or a diet of a Coleopteran insect the composition of claim 9.

14. The method of claim 12, wherein the dsRNA is delivered to a leaf, stem, seed, root, or soil of the plant.

15. The method of claim 12, wherein the plant is selected from the group consisting of Solanaceae plants, Brassicaceae plants, Poaceae plants, Cucurbitaceae plants, Fobaceae plants, Apiaceae plants, Amaranthaceae plants, and Malvaceae plants.

16. The method of claim 12, wherein the dsRNA is delivered in an amount sufficient to cause stunting, mortality, decreased feeding, or inhibited reproduction of a Coleopteran insect.

17. The method of claim 12, wherein the Coleopteran insect is of a species selected from the group consisting of: *Leptinotarsa* spp., *Phyllotreta* spp., *Cerotoma* spp., *Diabrotica* spp., *tribolium* spp., *Anthonomus* spp., and *Alticini* spp.

18. The method of claim 12, wherein the delivering step comprises applying the dsRNA to the surface of the plant, to the ground, to the Coleopteran insect, or to the diet of a Coleopteran insect.

19. A plant comprising the dsRNA of claim 1.

20. The plant of claim 19, wherein the plant is a Solanaceae plant, Brassicaceae plant, Poaceae plant, Cucurbitaceae plant, Fobaceae plant, Apiaceae plant, Amaranthaceae plant, or Malvaceae plant.

21. The composition of claim 9, wherein the composition is formulated as a liquid, a solution, a suspension, an emulsion, an emulsifiable concentrate, a concentrate solution, a low concentrate solution, an ultra-low volume concentrate solution, a water soluble concentrate solution, a bait, an invert emulsion, a flowable, an aerosol, a smoke, a fog, a flowable, a homogenous mixture, a non-homogenous mixture, a solid, a dust, a powder, a granule, a pellet, a capsule, a fumigant, an encapsulated formulation, or a micro-encapsulation formulation.

22. The composition of claim 9, wherein the composition is delivered as a spray, fog, seed treatment, drench, drip irrigation, in furrow, insect diet, or bait.

23. The dsRNA of claim 1, wherein the first strand comprises an RNA sequence that has 100% identity to the RNA sequence of any one of SEQ ID NOs: 19, 27-32, 36, 39, or 44-49.

* * * * *